(12) United States Patent  
Dehkordi et al.

(10) Patent No.: US 12,257,393 B2  
(45) Date of Patent: Mar. 25, 2025

(54) METHODS, SYSTEMS, APPARATUSES, AND DEVICES FOR FACILITATING STRESS-ADAPTIVE VIRTUAL EXERIENCE STATIONS

(71) Applicant: Brelyon, Inc., San Mateo, CA (US)

(72) Inventors: Barmak Heshmat Dehkordi, San Mateo, CA (US); Alok Ajay Mehta, San Mateo, CA (US); Christopher Barsi, Lee, NH (US); Albert Redo Sanchez, San Mateo, CA (US); Ramesh Raskar, Cambridge, MA (US)

(73) Assignee: BRELYON, INC., San Mateo, CA (US)

( * ) Notice: Subject to any disclaimer, the term of this patent is extended or adjusted under 35 U.S.C. 154(b) by 229 days.

(21) Appl. No.: 18/164,108

(22) Filed: Feb. 3, 2023

(65) Prior Publication Data

US 2023/0191077 A1  Jun. 22, 2023

Related U.S. Application Data

(63) Continuation-in-part of application No. 17/586,623, filed on Jan. 27, 2022, now Pat. No. 11,908,443.
(Continued)

(51) Int. Cl.
| | |
|---|---|
| *A61F 11/06* | (2006.01) |
| *A61H 23/02* | (2006.01) |
| *A61M 21/02* | (2006.01) |
| *A61N 5/06* | (2006.01) |
| *G06F 3/01* | (2006.01) |
| *G06T 19/00* | (2011.01) |
| *H04N 13/111* | (2018.01) |

(Continued)

(52) U.S. Cl.  
CPC ......... *A61M 21/02* (2013.01); *A61H 23/0245* (2013.01); *A61N 5/0618* (2013.01); *G06F 3/011* (2013.01); *G06T 19/006* (2013.01); *H04N 13/111* (2018.05); *H04N 13/122* (2018.05); *H04N 13/254* (2018.05); *H04N 13/383* (2018.05); *A61M 2021/0022* (2013.01); *A61M 2021/0038* (2013.01); *A61N 2005/0659* (2013.01); *A61N 2005/0661* (2013.01); *A61N 2005/0662* (2013.01); *G06T 2210/62* (2013.01); *G06T 2219/024* (2013.01); *H04N 2213/002* (2013.01)

(58) Field of Classification Search  
CPC .......... A61M 21/02; A61M 2021/0038; A61M 2021/0022; H04N 13/383; H04N 13/254; H04N 13/122; H04N 13/111; G06T 2219/024; G06T 2210/62; G06T 19/006; G06F 3/011; A61N 5/0618; A61N 2005/0662; A61N 2005/0661; A61N 2005/0659; A61H 23/0245  
USPC ................................................. 381/71.6, 301  
See application file for complete search history.

(56) References Cited

U.S. PATENT DOCUMENTS

| | | |
|---|---|---|
| 10,768,442 B1 | 9/2020 | Dehkordi |
| 11,196,976 B2 | 12/2021 | Heshmat Dehkordi |
| (Continued) | | |

*Primary Examiner* — Ammar T Hamid  
(74) *Attorney, Agent, or Firm* — Hsuanyeh Law Group PC

(57) ABSTRACT

A system for facilitating stress-adaptive virtual experience station includes a virtual display system and camera system coupled to a kinematic rig. An array of transducers coupled to the station interact with a user based on a feedback signal, configured for user health treatments, audio effects, or computational imaging techniques.

35 Claims, 54 Drawing Sheets

Related U.S. Application Data

(60) Provisional application No. 63/241,972, filed on Sep. 8, 2021.

(51) Int. Cl.
| | | |
|---|---|---|
| *H04N 13/122* | (2018.01) | |
| *H04N 13/254* | (2018.01) | |
| *H04N 13/383* | (2018.01) | |
| A61M 21/00 | (2006.01) | |
| H04R 5/02 | (2006.01) | |

(56) References Cited

U.S. PATENT DOCUMENTS

| | | |
|---|---|---|
| 2020/0150453 A1 | 5/2020 | Dehkordi |
| 2021/0103160 A1 | 4/2021 | Dehkordi |
| 2021/0356760 A1 | 11/2021 | Dehkordi |
| 2022/0057647 A1 | 2/2022 | Khorasaninejad et al. |
| 2024/0048622 A1* | 2/2024 | Berliner ............... G06K 7/1417 |

* cited by examiner

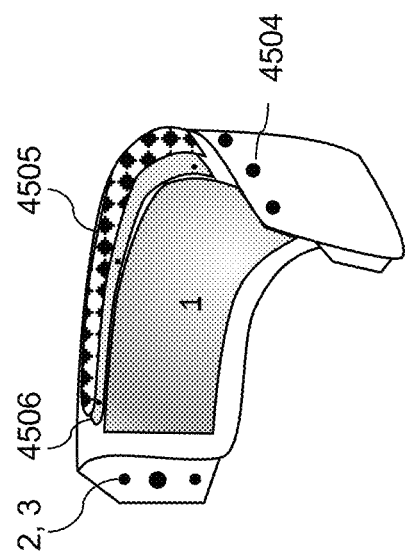
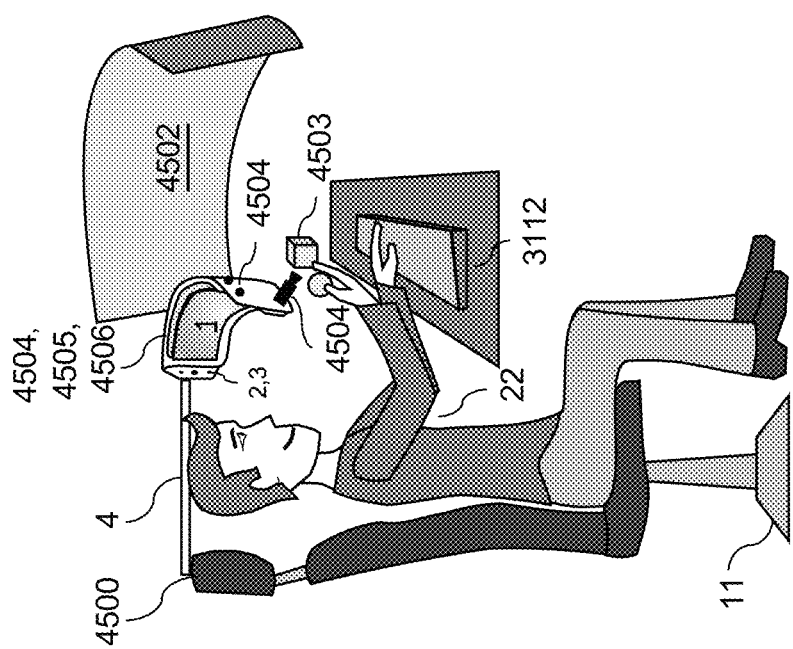

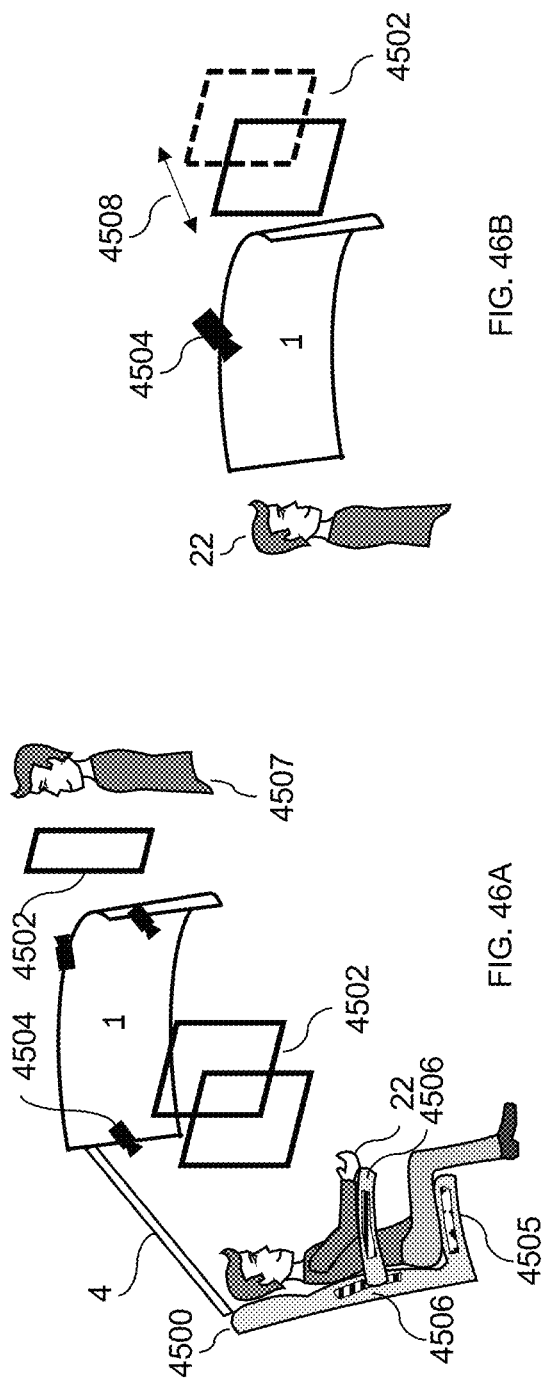
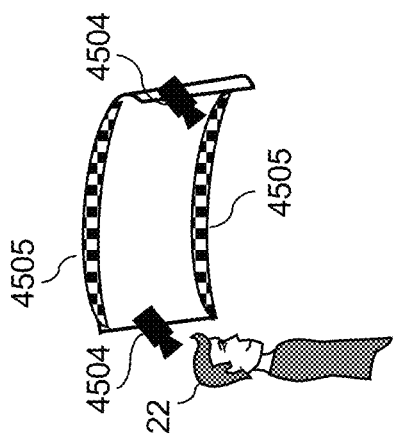
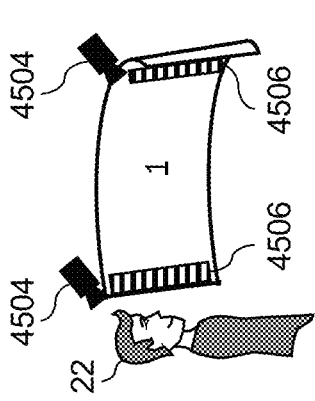
FIG. 46A
FIG. 46B
FIG. 46C
FIG. 46D

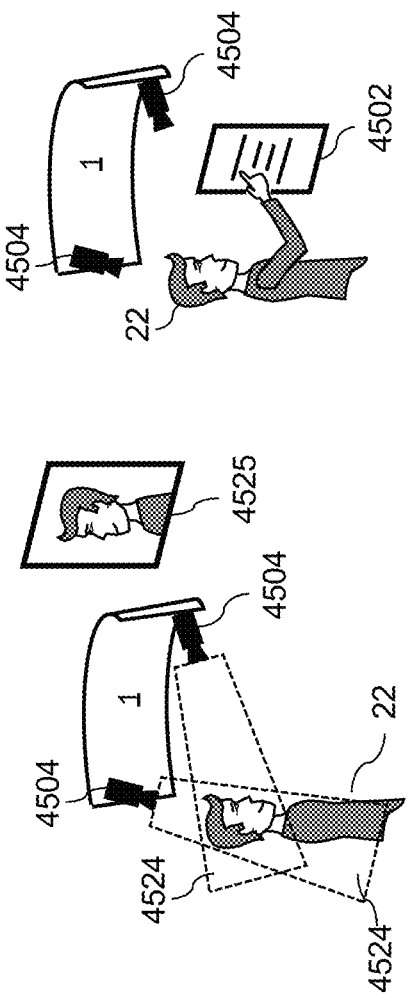
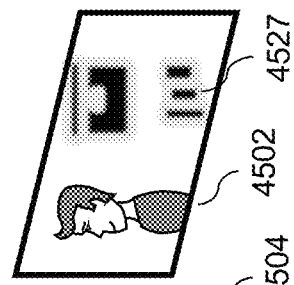
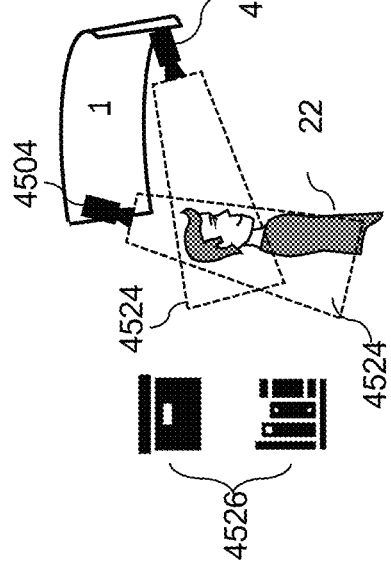
FIG. 48A
FIG. 48B
FIG. 48C

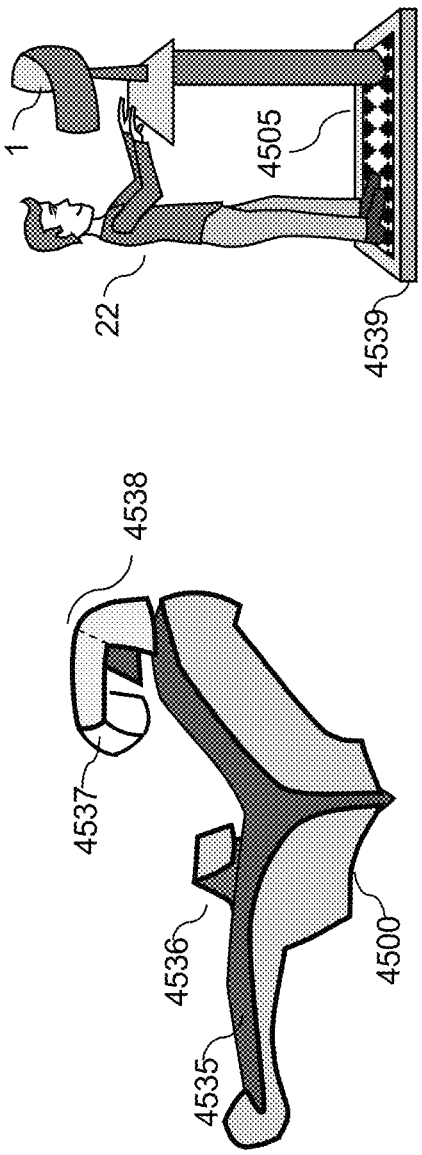
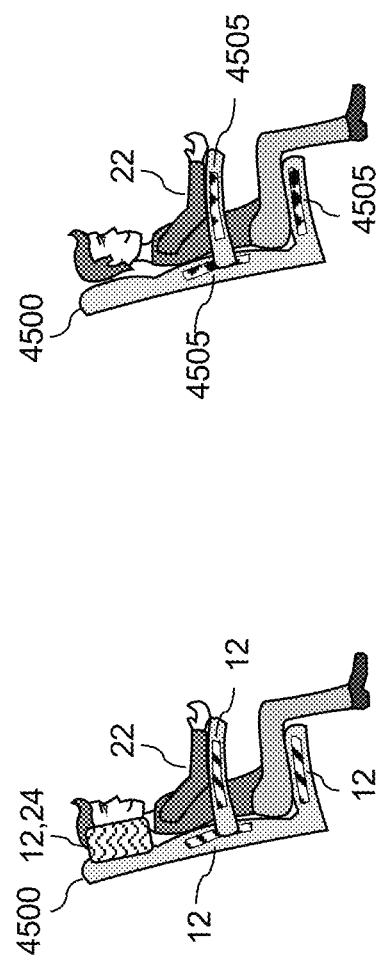
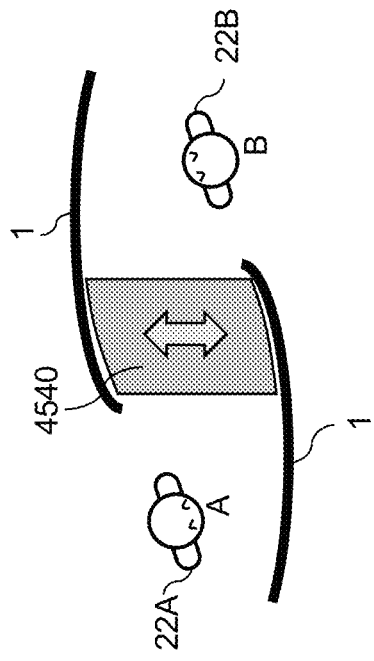
FIG. 51A
FIG. 51B
FIG. 51C
FIG. 51D
FIG. 51E

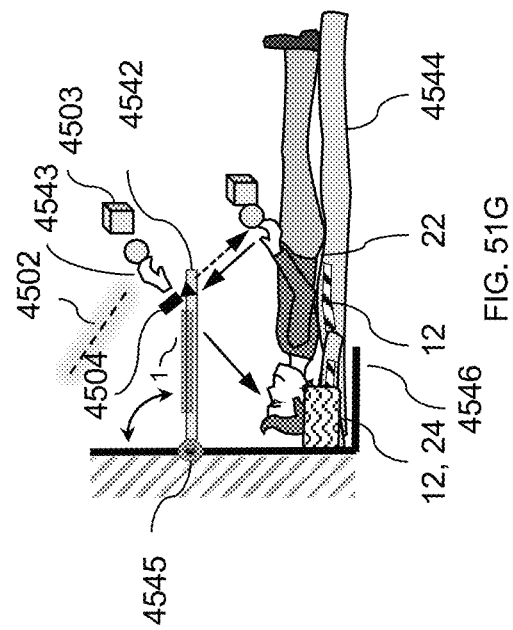
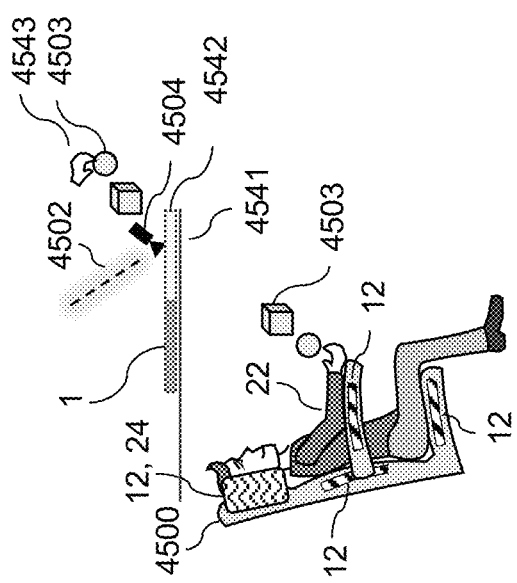

METHODS, SYSTEMS, APPARATUSES, AND DEVICES FOR FACILITATING STRESS-ADAPTIVE VIRTUAL EXERIENCE STATIONS

This is a continuation-in-part of U.S. patent application Ser. No. 17/586,623, filed on Jan. 27, 2022, and titled, "Methods, Systems, Apparatuses, and Devices for Facilitating Stress Adaption in a Workstation," which claims a priority to the U.S. provisional patent application No. 63/241,972 filed on Sep. 8, 2021, each of which are incorporated herein by reference in its entirety.

FIELD OF THE INVENTION

Generally, the present disclosure relates to the field of chairs and seats. More specifically, the present disclosure relates to methods, systems, apparatuses, and devices for facilitating stress adaption in a workstation.

BACKGROUND OF THE INVENTION

The field of chairs and seats is technologically important to several industries, business organizations, and/or individuals.

Currently, there is a dramatic shift to telework, where there is a distinct need for efficient use of space and real estate without any reduction in capabilities or functionality compared to conventional office workstation environments. As companies normalize and standardize to the telework environment, current telework workspace solutions are using size-restricted, modularized solutions that limit their overall functionality in terms of visual real estate offered and that lack the ability to manage the telework environment acoustic noise load. To support fundamental, telework activities such as teleconferencing, these workstations typically consist of a desk, computer, monitor or monitor array, stress-adaptive chair, webcam, acoustic speaker system, and microphone.

Conventional workstations, in general, have a footprint defined in terms of the minimum desk size required to adequately perform specific job functions. In these workstations, the desk size is directly correlated to the size of the single computer monitor or monitor array that is being deployed. For knowledge-based workers who typically use multiple monitor arrays, space restrictions in telework workstations limit the amount of accessible visual real estate at their disposal and a correspondingly decrease their production efficiency.

Additionally, acoustic noise sources in the telework environment can be significantly stronger in specific frequency ranges that make them more distracting than the noise typically found in conventional office spaces, necessitating an adaptive mechanism or system to manage the noise loads.

Therefore, there is a need for improved methods, systems, apparatuses, and devices for facilitating stress adaption in a workstation that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter, nor is this summary intended to be used to limit the claimed subject matter's scope.

Disclosed herein is a system for facilitating stress adaption in a workstation, in accordance with some embodiments. Accordingly, the system may include one or more microphones disposed on the workstation. Further, the one or more microphones may be configured for generating one or more first sound signals of one or more first sounds associated with an environment of the workstation. Further, the system may include a processing device communicatively coupled with the one or more microphones. Further, the processing device may be configured for analyzing the one or more first sound signals. Further, the processing device may be configured for determining one or more first sound characteristics of the one or more first sounds based on the analyzing of the one or more first sound signals. Further, the processing device may be configured for determining one or more second sound characteristics of one or more second sounds based on the determining of the one or more first sound characteristics. Further, the processing device may be configured for generating one or more second sound signals for the one or more second sounds based on the determining of the one or more second sound characteristics of the one or more second sounds. Further, the system may include one or more acoustic devices disposed on the workstation. Further, the one or more acoustic devices may be communicatively coupled with the processing device. Further, the one or more acoustic devices may be configured for emitting the one or more second sounds based on the one or more second sound signals. Further, the one or more second sounds destructively interfere with the one or more first sounds.

Further, the system may include the workstation may include a headrest, a seatback, a seat, a display chassis, and a wheelbase. Further, one or more of the one or more microphones and the one or more acoustic devices may be integrated into the headrest.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

FIG. 45A shows a virtual experience station with a display system and various transducers.

FIG. 45B is a close-up view of the virtual display that is depicted in FIG. 45A.

FIGS. 46A through 46D are a set of embodiments depicting various aspects of the virtual experience station of FIG. 45A.

FIGS. 48A through 48C illustrate various applications of the virtual experience station camera system for use in virtual reality or teleconferencing.

FIGS. 51A through 51G depict various alternative embodiments of the virtual experience station, including different configurations of a chair setup, a standing station, and a multi-user experience.

DETAIL DESCRIPTIONS OF THE INVENTION

Figure 1:
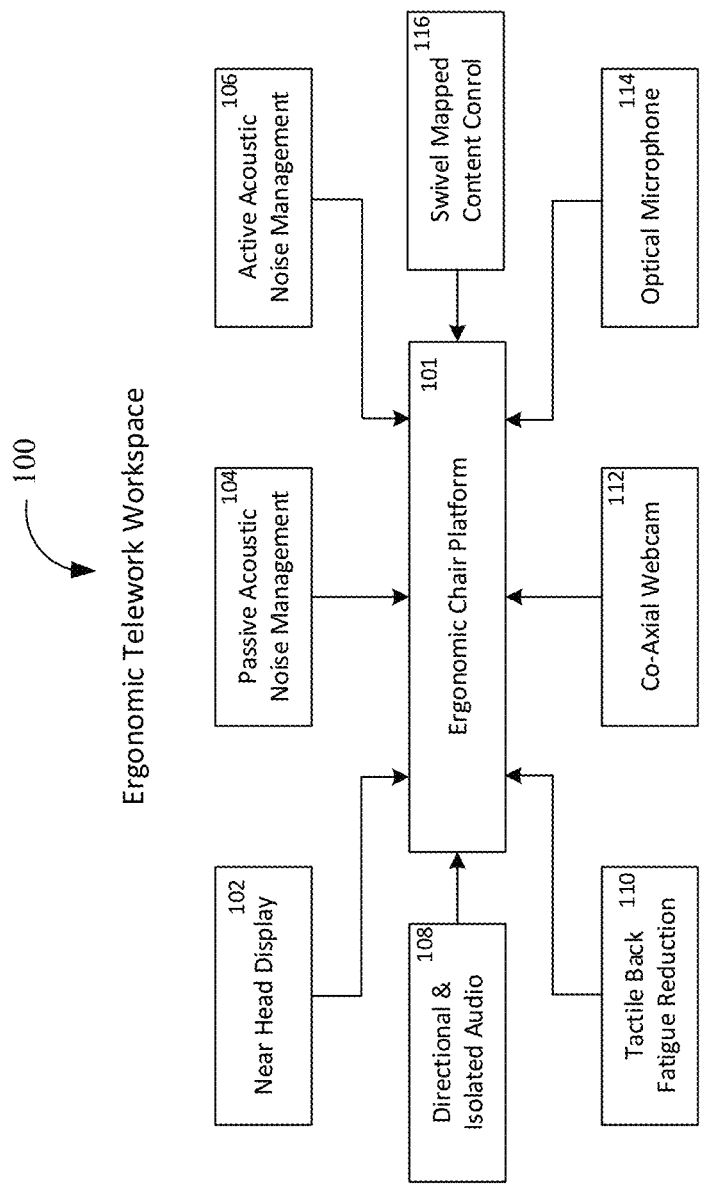
FIG. 1 is a block diagram representation of eight different technologies integrated into a chair to realize a stress-adaptive, acoustic noise managed, telework workstation, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and such embodiments are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods, systems, apparatuses, and devices for facilitating stress adaption in a workstation, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g., a mail server, a web server, a real-time communication server, an FTP server, a virtual server, a proxy server, a DNS server, etc.), a quantum computer, and so on. Further, one or more client devices and/or the server computer may be configured for executing a software application such as, for example, but not limited to, an operating system (e.g., Windows, Mac OS, Unix, Linux, Android, etc.) in order to provide a user interface (e.g., GUI, touch-screen based interface, voice-based interface, gesture-based interface, etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding, or decoding. Further, the server computer may include a communication device configured for communicating with one or more external devices. The one or more external devices may include, for example, but are not limited to, a client device, a third party database, a public database, a private database, etc. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, etc.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker, or a representative thereof. Further, the user as defined herein may refer to a human, an animal, or an artificially intelligent being in any state of existence, unless stated otherwise, elsewhere in the present disclosure. Further, in some embodiments, the one or more users may be required to successfully perform authentication in order for the control input to be effective. In general, a user or the one or more users may perform authentication based on the possession of human-readable secret data (e.g., username, password, passphrase, PIN, secret question, secret answer, etc.) and/or possession of a machine-readable secret data (e.g., encryption key, decryption key, bar codes, etc.) and/or or possession of one or more embodied characteristics unique to the user (e.g., biometric variables such as, but not limited to, fingerprint, palm-print, voice characteristics, behavioral characteristics, facial features, iris pattern, heart rate variability, evoked potentials, brain waves, etc.) and/or possession of a unique device (e.g., a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g., transmitting and/or receiving) with one or more sensor devices and/or one or more actuators in order to perform authentication. For example, the one or more steps may include receiving or using the communication device, the secret human readable data coming from an input device such as, for example, a keyboard, a keypad, a touch-screen, a microphone, a camera and so on. Likewise, the one or more steps may include receiving or using the communication device, the one or more embodied characteristics coming from one or more biometric sensors.

Further, one or more steps of the method may be automatically initiated, maintained and/or terminated based on one or more predefined conditions. For instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g., the server computer, a client device, etc.) corresponding to the performance of the one or more steps, physical state and/or physiological state and/or psychological state of the user, physical state (e.g., motion, direction of motion, orientation, speed, velocity, acceleration, trajectory, etc.) of the device corresponding to the performance of the one or more steps, and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g., a real-time clock), a location sensor (e.g., a GPS receiver, a GLONASS receiver, an indoor location sensor, etc.), a biometric sensor (e.g., a fingerprint sensor), or a usage sensor, etc., associated with the device corresponding to performance of the or more steps.

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving or using the communication device, the one or more predefined conditions coming from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g., initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview

The present disclosure describes methods, systems, apparatuses, and devices for facilitating stress adaption in a workstation. Further, the disclosed system may be configured for facilitating acoustic noise management in a workstation. Further, the disclosed system may be configured for facilitating a stress-adaptive telework station using a concentric light field display, acoustic noise management systems, and high-frequency stress transmission systems. Further, the workstation may include a chair. Further, the workstation may be configured to be utilized by a user. Further, the system may include at least one microphone, a processing device, and at least one active acoustic system. Further, the at least one microphone may be disposed on at least one portion of the workstation proximal to a head of the user. Further, the at least one microphone may be configured for generating a sound profile of one or more first sounds associated with an environment of the workstation. Further, the sound profile may be characterized by at least one sound characteristic of the one or more first sounds. Further, the processing device may be communicatively coupled with the at least one microphone. Further, the processing device may be configured for analyzing the sound profile. Further, the processing device may be configured for generating at least one signal based on the analyzing. Further, the at least one active acoustic system may be communicatively coupled with the processing device. Further, the at least one active acoustic system may be configured for generating one or more second sounds based on the at least one signal.

Further, in some embodiments, the disclosed system may be configured for facilitating acoustic noise management in the workstation. Further, the workstation may include a chair. Further, the workstation may be configured to be utilized by a user. Further, the workstation may include a concentric light field near-head display disposed on the workstation proximal to a face of the user. Further, the system may include at least one optical microphone, at least one microphone, and a processing device. Further, the at least one optical microphone may be disposed on the concentric light field near-head display. Further, the at least one optical microphone may be configured for generating at least one first signal based on a change of at least one light characteristic of light associated with at least one portion of the face. Further, the at least one microphone may be disposed on at least one portion of the workstation proximal to a head of the user. Further, the at least one microphone may be configured for generating at least one second signal based on one or more environment sounds associated with the workstation. Further, the processing device may be communicatively coupled with the at least one optical microphone and the at least one microphone. Further, the processing device may be configured for analyzing the at least one second signal based on the at least one first signal. Further, the processing device may be configured for extracting the one or more user sounds from the one or more environment sounds based on the analyzing.

Further, in some embodiments, the system may be configured for facilitating display management in the workstation. Further, the system may include at least one sensor, a processing device, and a concentric light field near-head display. Further, the at least one sensor may be disposed on the workstation. Further, the at least one sensor may be configured for generating sensor data based on at least one movement of the workstation. Further, the processing device may be communicatively coupled with the at least one sensor. Further, the processing device may be configured for analyzing the sensor data. Further, the processing device may be configured for generating at least one command based on the analyzing. Further, the concentric light field near-head display may be communicatively coupled with the processing device. Further, the concentric light field near-head display may be configured for displaying at least one content on the concentric light field near-head display. Further, the concentric light field near-head display may be configured for modifying the at least one content based on the at least one command.

Further, the disclosed system may be configured for facilitating a stress-adaptive telework station using the concentric light-field display, acoustic noise management systems, and high-frequency stress transmission systems.

Further, the disclosed system may be associated with an office desk workspace or gaming stations, where a concentric near-head display and/or passive and/or active acoustic management systems and/or teleconference capabilities and/or muscle stress and strain reduction tactile systems are incorporated into a complete stress-adaptive workstation platform to support telework or entertainment activities. Further, the disclosed system integrates all the key modular components with acoustic noise management capability in a space-efficient telework workstation. Further, the disclosed system configured for facilitating the stress-adaptive telework station using the concentric light field display, acoustic noise management systems, and high-frequency stress transmission systems may overcome the limitations derived from the relationship between desk size and supportable visual real estate (field of view and display size perception) in order to not impact user productivity compared to standard office workstations.

Further, the disclosed system may be associated with stress-adaptive, space-efficient, fully functional telework workstations described in four main sections: incorporation of a concentric near-head display; incorporation of passive and/or active noise management systems into a stress-adaptive chair; supplementing workstation and display chassis with teleconferencing capabilities, and integration of tactile muscle stress and strain reduction arrays into a seat back support and a seat.

Further, the term "arbitrarily engineered" refer to "of being any shape, size, material, features, type or kind, orientation, location, quantity, components, and arrangements of components with single or an array of components that would allow the methods and the systems or that specific component to fulfill the objectives and intents of the methods and the systems or that specific component with in the methods and the systems."

In this disclosure, ergonomic features refer to the aspects of a workstation designed for efficiency and comfort in a working environment. These features include, but are not limited to, design aspects such as seat height, seat width and depth, a distance between monitor and user, backrest lumbar support and recline positioning, swivel positioning, armrests, headrest, materials, temperature control, and mobility.

In this disclosure, stress-adaptive features refer to the aspects of a workstation designed to activate stress-relieving features such as high-frequency vibrations induced at sub 300 Hz, or reclining or changing shape depending on a desired trigger, such as input from acoustic sensors, the posture of the user, a timer, or combination of any of these triggers.

In this disclosure, the display of the concentric near-head display refers to an emissive display which can be based on any technology, such as, but not limited to Liquid Crystal Display ("LCD"), Thin-film Transistor ("TFT"), Light Emitting Diode ("LED"), Organic Light Emitting Diode ("OLED") arrays, Active Matrix Organic Light Emitting Diode ("AMOLED"), micro-LED, polymer light emitting diode (POLED), MOLED, spatial light modulators (SLMs), projection or angular projection arrays on flat-screen or angle-dependent diffusive screen, or any other display technology and/or mirrors and/or half mirrors and/or switchable mirrors or liquid crystal sheets arranged and assembled in such a way as to exit bundles of light with divergence apex at different depths or one depth from the core plane, or waveguide-based displays. Other sources can be generic light sources, such as one or several LEDs, backlights, or laser beams, configured for use, for example, in projection-based display systems. In some display systems, light sources can be coupled with masks or patterned elements to make the light source segmented and addressable.

A concentric near-head display is also a virtual display system, is a display system that produces images which can produce three-dimensional perception. Such images may rely on either or both monocular depth cues and vergence depth cues. Virtual images may be stereoscopic, autostereoscopic, or (auto)multi-scopic. A virtual display system may be a free-standing question, like a computer monitor or a television. It may be part of a mobile phone, tablet, headset, smart watch, or any portable device. It may be for a single user or multiple users in any application. The display content or virtual images is the set of images that the viewer sees when using the display system. In some embodiments, the virtual display system produces an eyebox whose volume is big enough to encompass both eyes of a viewer simultaneously. In this case, a pixel from a display source can be seen by both eyes. In another embodiment, the virtual display system produces a left eyebox and a right eyebox, configured for simultaneous viewing by a left and a right eye.

Virtual display systems can incorporate any hardware in displays, including liquid crystals or other polarization-dependent elements to impact properties of the display; any type of mirror or lens to redirect the light path, influence the size in any dimension, modify the focal depth, or correct for aberrations and distortions; any surface coatings, active elements; spectral or spatial filters to assist in image quality; optical cavities; or any type of element or coating to serve as a shield layer or antireflection layer to reduce unwanted, stray, or ambient light from reaching a viewer. In the embodiments disclosed herein, virtual display systems are optical virtual display systems, but virtual display systems can be of any modality, including radio-frequency or acoustic display systems, configured for consumption by a person's human auditory system. In all embodiments in this disclosure, the displays can be curved.

In some embodiments, a field evolving cavity is included as a component in the virtual display system. A "field evolving cavity" (also "FE cavity" or "FEC") is an optical cavity in which light folds back can fold back on itself. An FEC can be a component in a virtual display system and assists in providing depth cues for three-dimensional (3D) perception for a user. In some embodiments, a depth cue is a monocular depth cue.

A "lightfield" is a mathematical model of light propagation that relies on the geometric ray approximation. Some lightfield models incorporate wave-based effects like diffraction. A lightfield display is three-dimensional display that is designed to produce 3D effects for a user using lightfield modeling. A concentric near-head or other virtual display system may be a light field display in which for any two pixels of the display at a fixed radius from the viewer, the chief ray of the first pixel's light cone intersects with that of the second pixel's light cone. In some embodiments, the concentric near-head display or virtual display system is a holographic display, which relies on the wave nature of light to produce imaging based on a wavefront of the light. A concentric near-head display produces an image that is focusable to the eye at all points.

A virtual display system, including a concentric near-head display produces image content, virtual images, of display content that trigger depth cues in a viewer, who consequently perceives the display content at a variable depth, or perceives different parts of the display content at various depths relative to each other, or perceives display content that appears at a different depth than the physical display system. In some embodiments, parallax effects are produced. In some embodiments, 3D effects are triggered stereoscopically, by sending different images to each eye. In some embodiments, 3D effects are triggered using "monocular depth" cues, wherein each eye focuses or accommodate to the appropriate focal plane or depth to see the display content clearly. Each depth at which content is located is called a virtual layer, a virtual depth, or a focal plane. The virtual depth of a virtual image may be dynamically adjustable via electric, electrooptic, or nonlinear control in the display system; a user or sensor input; or a pre-programmed routine.

The virtual images may further appear in a region displaced laterally from the physical display system, for example, to extend the field of view.

In some embodiments, the properties of interest of the display content include resolution, refresh rate, brightness, field of view, viewable zone, monocular depth or accommodation, vergence, eye box or headbox, etc.

The terms "virtual stack," "multilayer images," "multilayer display images," or "overlayed images" refer to information grouped in virtual layers organized in a stacked fashion. A display system that can produce multilayer images may be called a multilayer virtual display system. For example, a multilayer virtual display system is one in which display content is shown in such a way that a viewer must accommodate his eyes to different depths to see the content. Multilayer displays comprise transparent displays in some embodiments.

Further, passive acoustic noise management refers to any passive material-based physical paneling measures that prevent or reduce the ambient acoustic noise signals that are impingent on the user's workstation environment. The passive acoustic noise reduction approaches generally consist of single-layer foam, composite multilayer foam structure, or acoustic metamaterial structure-based paneling material that is integrated into the ergonomic chair design to reduce ambient noise without any moving parts or electronics. The geometrical layout of these passive panels can be arbitrarily designed to balance the trade-off between ergonomics and acoustic noise management capabilities. The result of the noise management scheme is an isolated acoustic region surrounding the user that has significantly lower ambient noise levels.

Further, the term "acoustic foam" refers to any passive acoustic noise management material which can be based on any single or combination of, but not limited to, melamine foam, convoluted foam, polyurethane foam, and Polyester Film.

Further, the term "tactile acoustic transducer" refers to any acoustic, ultrasonic, piezoelectric, Hall effect, capacitance variation, resistance variation, or induction variation mechanism where the transducer can be used to deliver acoustic frequency vibrations for hearing through conduction, or for massaging purposes, or as stress sensors.

Furthermore, the term "acoustic metamaterial structure" refers to composite, multilayer acoustic foam structures with 3D-structured surface topologies designed to tailor the frequency-dependent reflection, transmission, and absorption properties of the effective material.

Further, "active design" or "active components" or generally the adjective "active" refers to a design or a component that can vary with an electrical signal or the acoustic signals that are perceived by the user as a function of the ambient acoustic signal spectral content and workstation specific acoustic scattering map.

Further, the term "active acoustic noise management" refers to an electroacoustic or electromechanical system that cancels the primary (unwanted) noise based on the principle of superposition; specifically, an anti-noise signal of equal amplitude and opposite phase is generated and combined with the primary noise, thus resulting in the cancellation of both noises.

Further, the term "optical microphone" refers to a microphone that uses an optical remote-pickup technology that senses the user's cheek, forehead, or chin as a membrane and that detects skin vibrations induced from the speaking process. This provides an independent and reliable reference audio signal in any environment. Unlike conventional microphones, which only pick up airborne sound energy, the optical microphone picks up skin vibration speech energy by reflecting light from the face of the speaker to the optical microphone's sensor. The wave vibration power in air is much weaker than that in body tissues, which corresponds to the voice volume in the same tissue position being higher than the background noise. This is because skin/soft tissues vibrate mainly because of sound bouncing in the inner body vocal cords and not as a response to external acoustical signals/noise. Sound waves from outside the body create minimal vibrations inside the body soft tissues (0.001 less effect than from the inner voice). Integrating optical microphones of this type into the chassis of the concentric near-head display in close proximity to the user's face provides high levels of sensitivity with a large received signal-to-noise ratio (SNR) audio signal that is remotely sensed.

Further, the terms "directional audio" and "isolated audio" refer to active acoustic systems which can be based on any technology such as but not limited to Parabolic Speakers, Flat Panel Speakers, Ultra-Sonic Speakers, or Phased Speaker Arrays for acoustic signal beam steering.

Further, an "imaging system" refers to any apparatus that acquires an image that is a matrix of information about light intensity, or, temporal, spectral, polarization or entanglement or other properties used in any application or framework, such as cellphone cameras, industrial cameras, photography or videography cameras, microscopes, telescopes, spectrometers, time-of-flight cameras, ultrafast cameras, thermal cameras, or any other type of imaging system.

Further, a "webcam" refers to any imaging system hardware that feeds or streams an image or video in real-time to or through a computer to a computer network, such as the internet. The webcam in this embodiment is designed to operate with the optical axis co-axially aligned with the user's face.

Further, a "tactile acoustic signal actuation" refers to any audio signal that is felt through touch and is heard through bone conduction or tissue conduction. Tactile acoustic transducers can produce a wide range of tactile and audible frequencies that can be coupled to surfaces and propagated to different spatial locations along the coupled surface.

Further, a "high-frequency stress transmission system" refers to the revitalizing of the lower or mid-back muscle areas via the acoustic transducer nodes embedded in the chair back and/or seat cushion that can provide traveling or spot-based tactile perturbation for soothing of tired or tense muscles in the area. Embedded heaters and/or coolers surrounding the acoustic transducer nodes provide an additional level of back muscle stress and strain reduction via targeted thermal transfer.

Further, "chair swivel mapped content control capability" refers to the ability to prescribe content displayed in the concentric near-head display as a function of the chair rotational position. In some embodiments, this is incorporated into a modularized workspace solution that is representative of the chair embodiment of the Ultra Reality display and acoustic/telecommunication hardware components such as webcam integration and chair swivel, content-specific mapping technique. Further, a movement of critical components relative to a chair's rotational swivel position is tracked.

FIG. 1 is a block diagram of an ergonomic telework workspace 100 overviewing eight different technologies that when collectively integrated into an ergonomic chair platform 101, provide a stress-adaptive telework workstation, in accordance with some embodiments. Accordingly, eight different technologies may include a near display 102, passive acoustic noise management 104, an active acoustic noise management 106, a directional and isolated audio 108, a tactile back fatigue reduction 110, a co-axial webcam 112, an optical microphone 114, and a swivel mapped content control 116.

Figure 2:
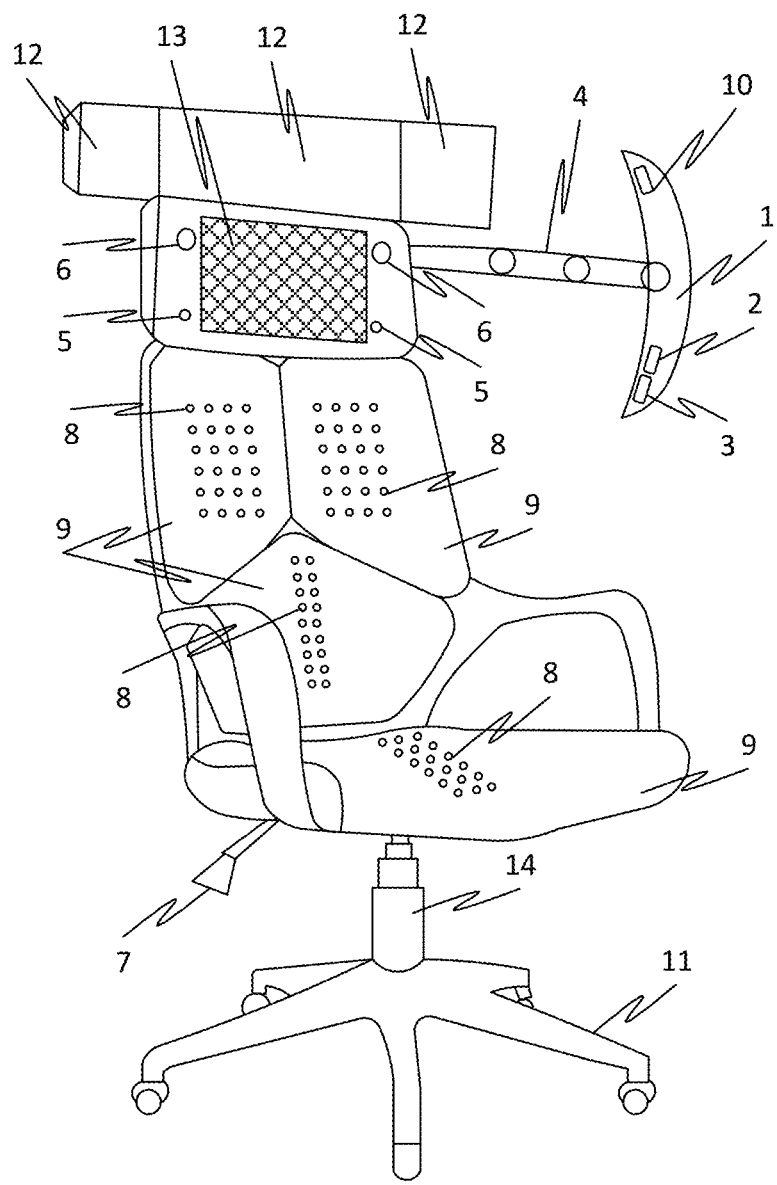
FIG. 2 is a schematic rendering of a stress-adaptive telework workstation using concentric near-head light field display and acoustic noise management systems, in accordance with some embodiments.

FIG. 2 depicts an embodiment of an ergonomic workstation, where 1 is a concentric light-field near-head display, 2 and 3 are, respectively, a directional audio system and optical microphone arrays integrated into the display chassis, 4 is a robotic and telescopic monitor arm mount, 5 and 6 represent, respectively, an active noise cancellation speaker and an error canceling microphone integrated into the headrest, 7 is a seat tilt control mechanism, 8 is a tactile transducer array coupled into a mesh under tensile stress integrated into the seat back and cushion to reduce the induce high-frequency (<100 Hz) acoustic vibrations to the user body via stress transmission, 9 corresponds to an internal heater and/or cooling element locations embedded in the seat back and cushion, 10 is a co-axial webcam integrated into the display chassis. Here co-axial refers to a setting where the camera isn't directly looking at the user, but rather the camera is looking at the reflection of a user from the reflective surfaces inside the near-head display. In such a manner, the user sees a virtual image in the near-head light field display but the webcam sees directly the user's face through the reflection. 11 is a low-friction and high-load wheelbase, 12 represents a passive acoustic noise reduction paneling, 13 is a head hammock for ergonomic user head positioning purposes, and 14 is a telescopic seat height adjustment and swivel content control interface.

Figure 3:
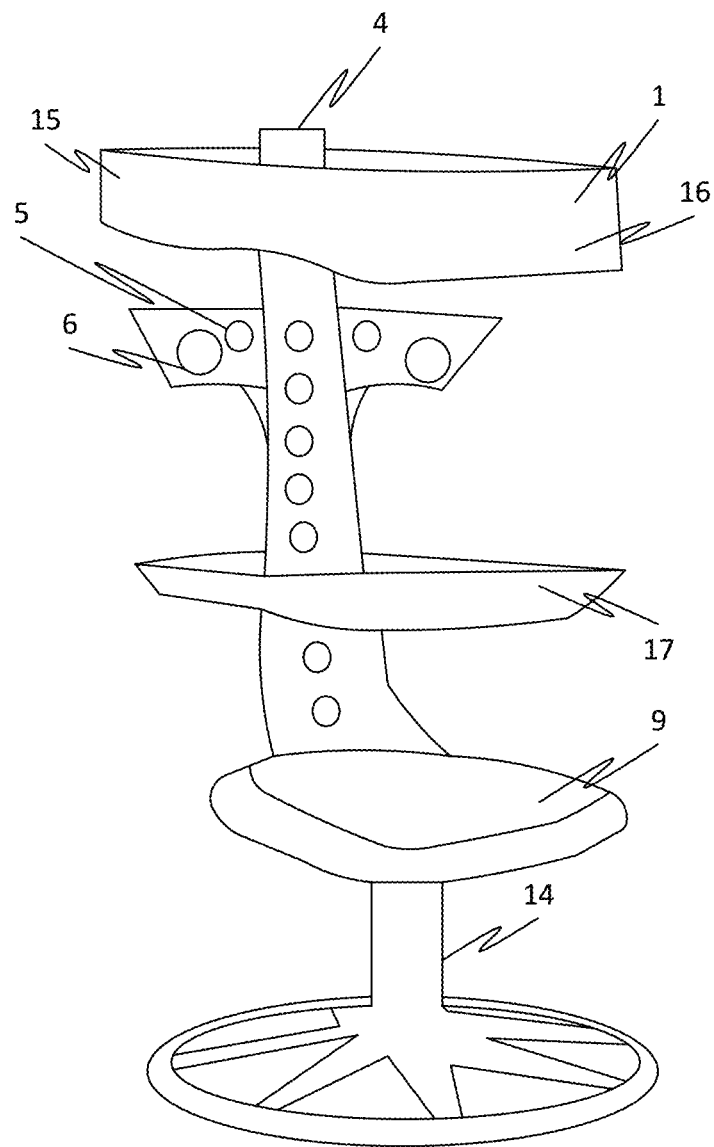
FIG. 3 is a schematic rendering of the stress-adaptive and surround acoustic noise managed, telework space, in accordance with some embodiments.
Figure 4:
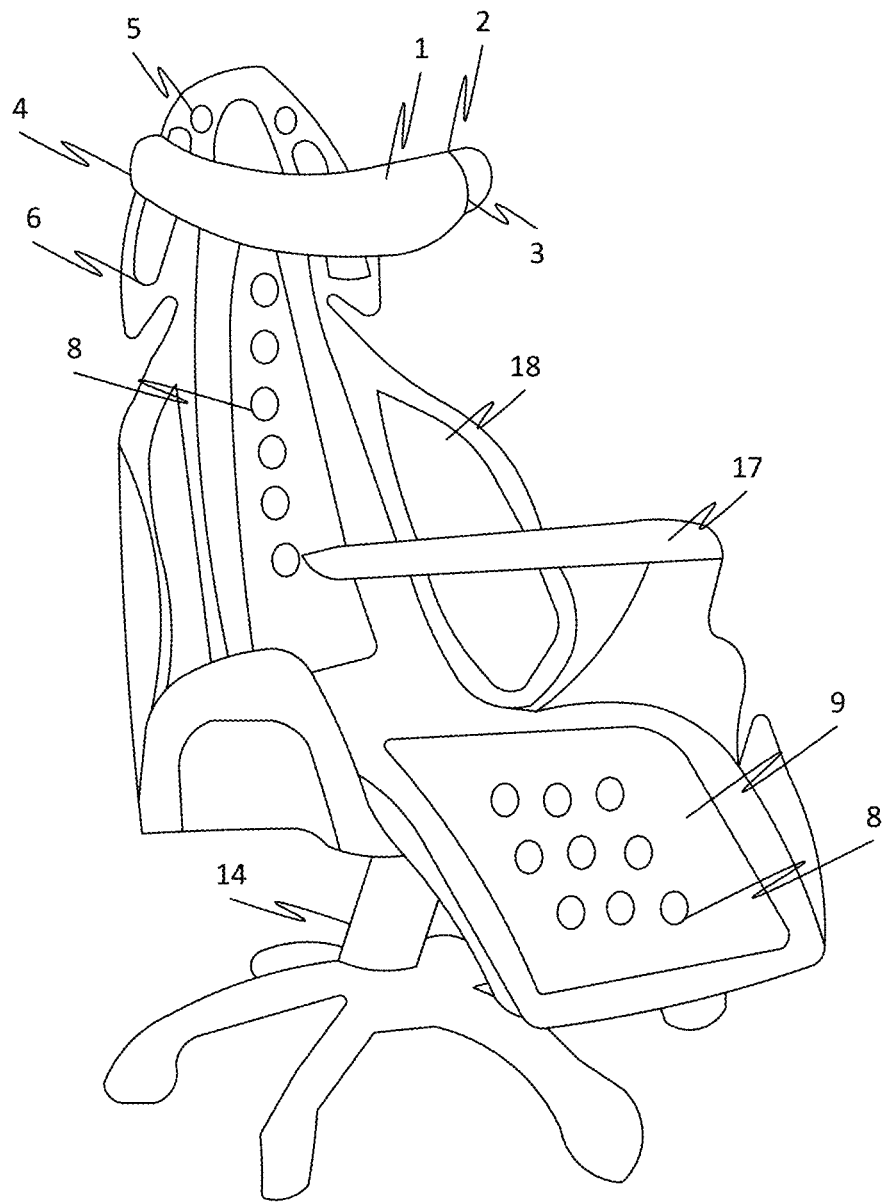
FIG. 4 is a schematic rendering of the stress-adaptive and surround acoustic noise managed, telework space, in accordance with some embodiments.
Figure 5:
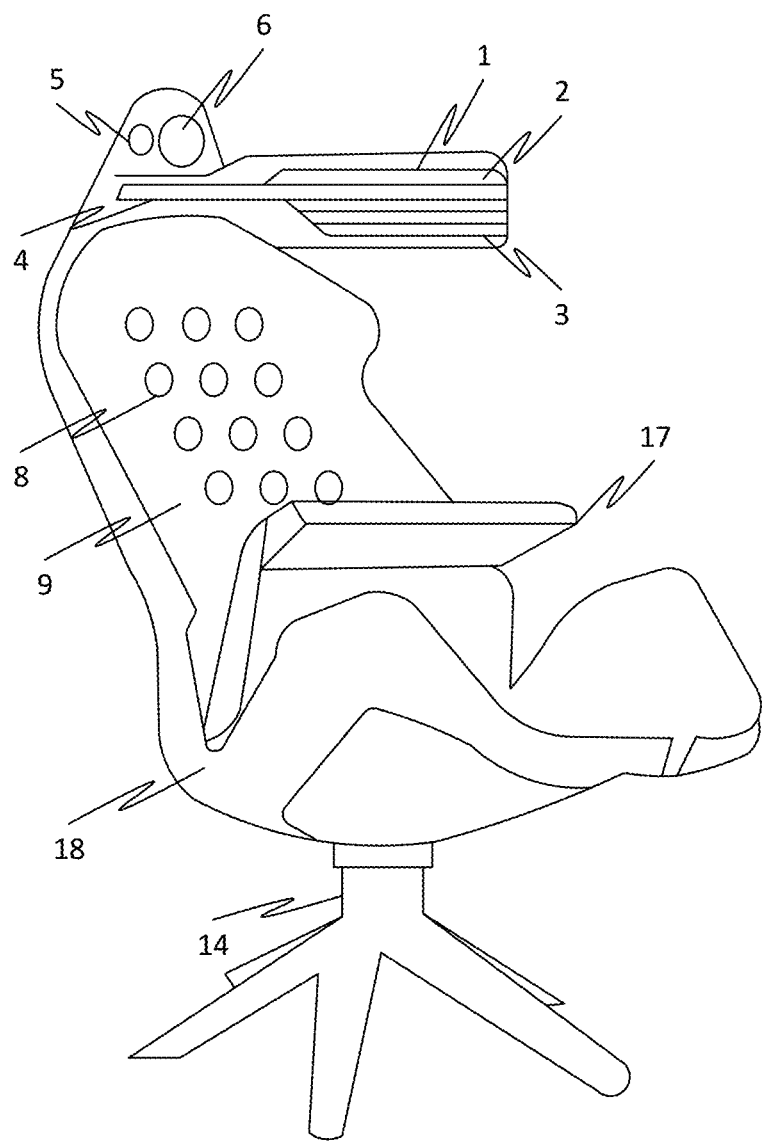
FIG. 5 is a schematic rendering of the stress-adaptive and surround acoustic noise managed, telework space, in accordance with some embodiments.

FIG. 3, FIG. 4, and FIG. 5 represent other embodiments of a complete stress-adaptive immersive station (such as the ergonomic workstation) to support telework and gaming activities, where 15 is a passive acoustical ring paneling, 16 is a vertically adjustable display immersion portal where the ring has the display inside the ring and can be moved up and down via a telescopic structure in 16, and 17 corresponds to two half-ring armrests with a keyboard embedded inside. The half rings swing to the side for the user to sit and can be closed once the user is sitting in the station for FIG. 3. For FIG. 4 and FIG. 5, this is just an adjustable panel that the keyboard can rest on. Further, a panel indicated by 18 represents the workstation temperature management modules with heating and cooling elements integrated beneath the panel surface.

Figure 6:
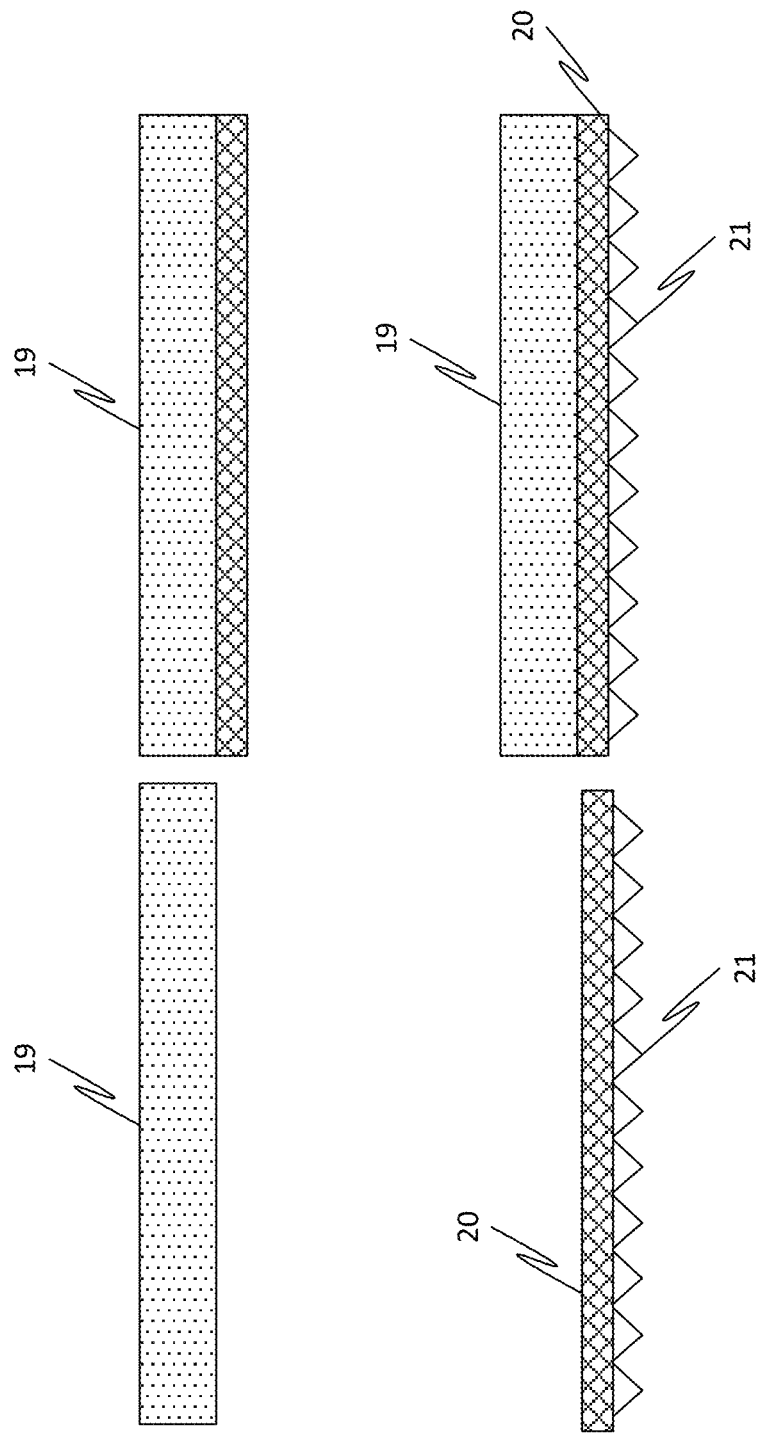
FIG. 6 provides renderings of different classes for passive noise absorption panels that can be integrated into the workstation, in accordance with some embodiments.

FIG. 6 depicts the four different variants for the passive acoustic noise reduction approaches integrated into the stress-adaptive workstations described here. 19 represents a single layer acoustic melamine foam, 20 is a composite multilayer melamine foam structure, and 21 is the acoustic metamaterial structure-based paneling with surface structuring to minimize acoustic reflection and enhance absorption. The geometrical layout of these passive panels can be arbitrarily engineered to balance the trade-off between stress-adaptive and acoustic noise management capabilities. The result of the noise management scheme is an isolated acoustic region surrounding the user which has significantly lower ambient noise levels.

Further, a passive acoustic noise reduction approach generally consists of single-layer foam, composite multilayer foam structure, or acoustic metamaterial structure-based paneling material that is integrated into the ergonomic chair design to reduce ambient noise without any moving parts or electronics involved. The geometrical layout of these passive panels can be arbitrarily designed to balance the trade-off between ergonomics and acoustic noise management capabilities.

The geometrical layout of the passive acoustic paneling described in FIG. 6 is integrated into the ergonomic chair embodiments described in FIG. 1, FIG. 2, FIG. 3, FIG. 4, and FIG. 5, using either a U-shaped or V-shaped passive acoustic management embodiment, surrounding the user and positioned in the head-rest, such that it looks like a head hammock, 13, to provide maximal acoustic noise dampening while maintaining a high level of ergonomic comfort for the user.

Figure 7:
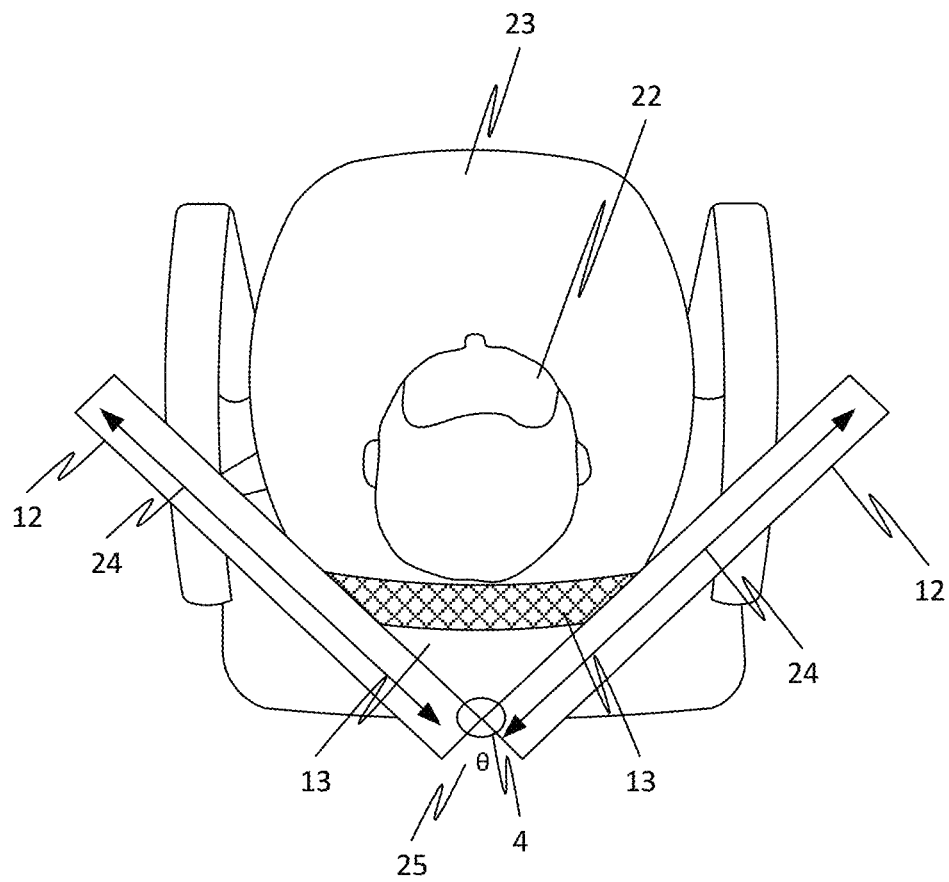
FIG. 7 is a top view of the V-Mount for integration of passive noise cancellation panels into the workstation, in accordance with some embodiments.

FIG. 7 depicts the top-down perspective view of a user, 22, sitting in the stress-adaptive station 23, with the passive acoustic management embodiment geometrically laid out in a U-shape with a length of acoustic foam, 24, and angular subtense, θ, 25 between the two acoustic foam panels.

For a fixed length of acoustic foam, the amount of acoustic signal power absorption experienced by the user is a function of the angular subtense, θ, between the two acoustic foam panels for a fixed acoustic source and receiver distance.

Figure 8:
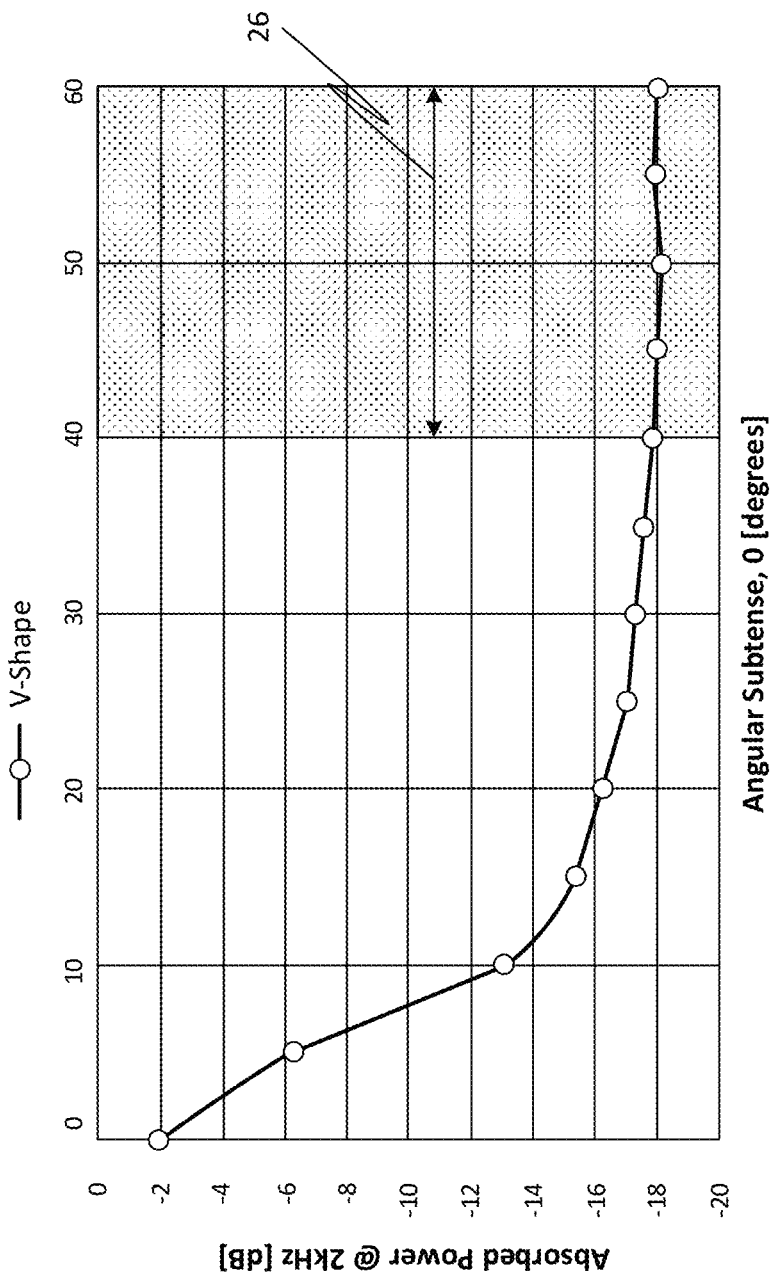
FIG. 8 is a diagram showing the acoustic noise damping characteristics as a function of angle positioning for the V-Mount, in accordance with some embodiments.

FIG. 8 depicts the angular-dependent acoustic signal power absorption, for a signal frequency of 2 kHz, that is characteristic of the V-shaped embodiment described here, showing a stabilized operational range 26, once the angular subtense between the two foam panels exceeds 40°. Free-space signal attenuation measurements of the acoustic signal indicate or are equivalent to ~6 dB for every doubling of the distance between the acoustic source and receiver, which, within the operational range of angular subtense, corresponds to effectively extending the physical source-to-receiver distance to a ~5 times virtual distance to the acoustic noise source for the given amount of acoustic power absorption.

Figure 9:
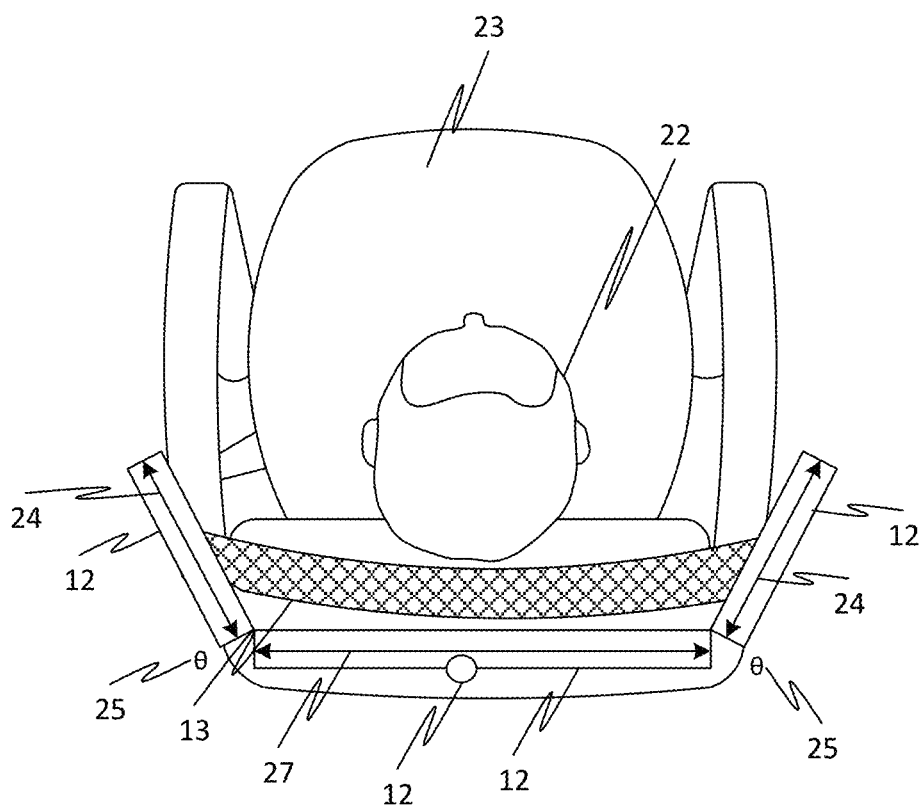
FIG. 9 is a top view of the U-Mount embodiment for integration of passive noise cancellation panels into the workstation, in accordance with some embodiments.

The top-down perspective view of the U-shaped chair embodiment is depicted in FIG. 9, showing the user with head positioning defined by the headrest resembling a hammock apparatus and surrounded by the U-shaped passive acoustical management paneling. The hammock mesh is almost invisible to the sound. Therefore, while the head is surrounded by an acoustic dampening structure and is very close to acoustic surfaces, the acoustic dampening structure is not directly impacting the performance of those surfaces.

Figure 10:
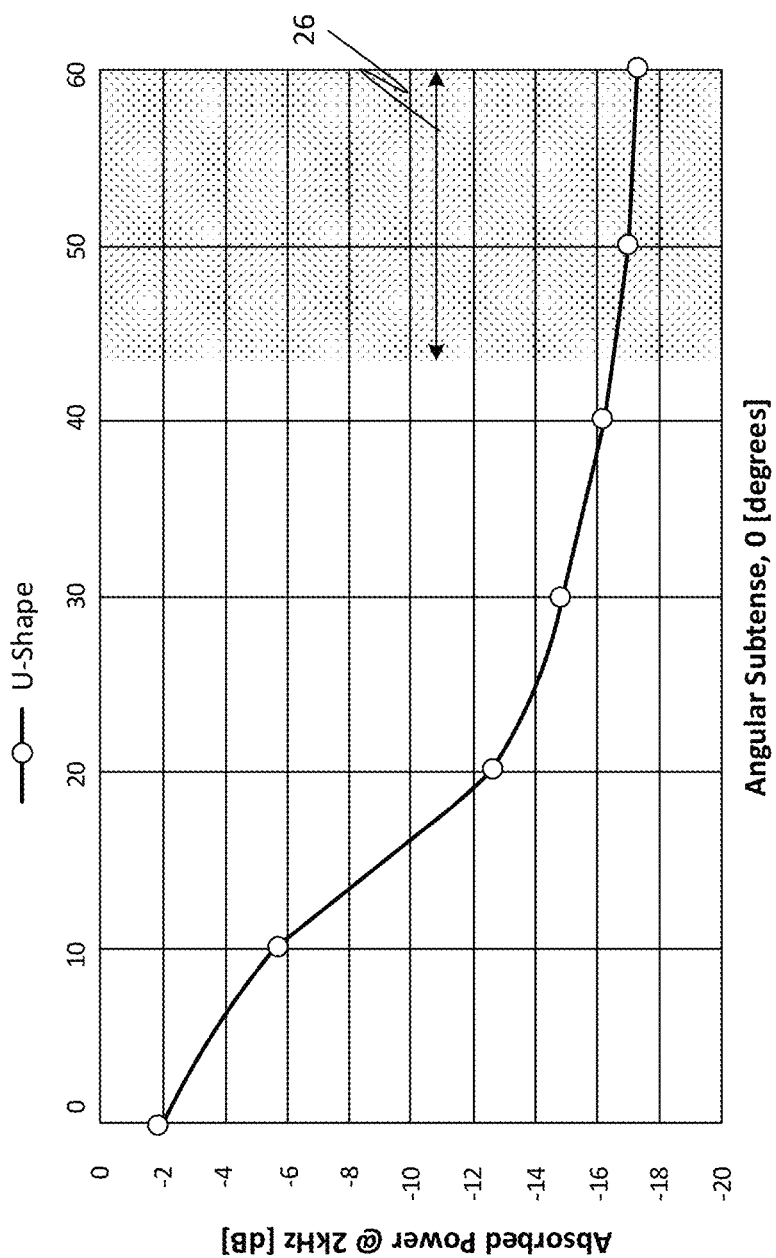
FIG. 10 is a diagram showing the acoustic noise damping characteristics as a function of angle positioning for the U-Mount, in accordance with some embodiments.

As described for the V-Shape embodiment, FIG. 10 depicts the angular dependent acoustic signal power absorption, for a signal frequency of 2 kHz, that is characteristic of the U-shaped embodiment described here, showing a stabilized operational range 26, once the angular subtense between the two foam panels exceeds 45° for a fixed length of acoustic foam, 27, that is directly behind the user and head hammock. Using the free-space signal attenuation measurement indicating ~6 dB for every doubling of the distance between the acoustic source and receiver, within the operational range of angular subtense, there is again an effective extension of the source-to-receiver distance of ~5 times. This means that since there is −15 dB reduction at 45° of the U-shaped side pads; this structure may attenuate the sound as if the source of the sound was almost ((15/6)×2=5) further away. For example, if a vacuum cleaner were making noise 1 meter right in front of the user sitting in this station, the noise from the vacuum cleaner to the user would sound as if the noise is 5 meters away.

An optical microphone is integrated at multiple positions within the concentric near-head light field display chassis to provide three functions: acoustic signal input for the calibration sub-system to characterize the user's acoustic environment, a teleconferencing microphone, and the error and input microphone inputs for the active noise cancellation sub-system.

Figure 11:
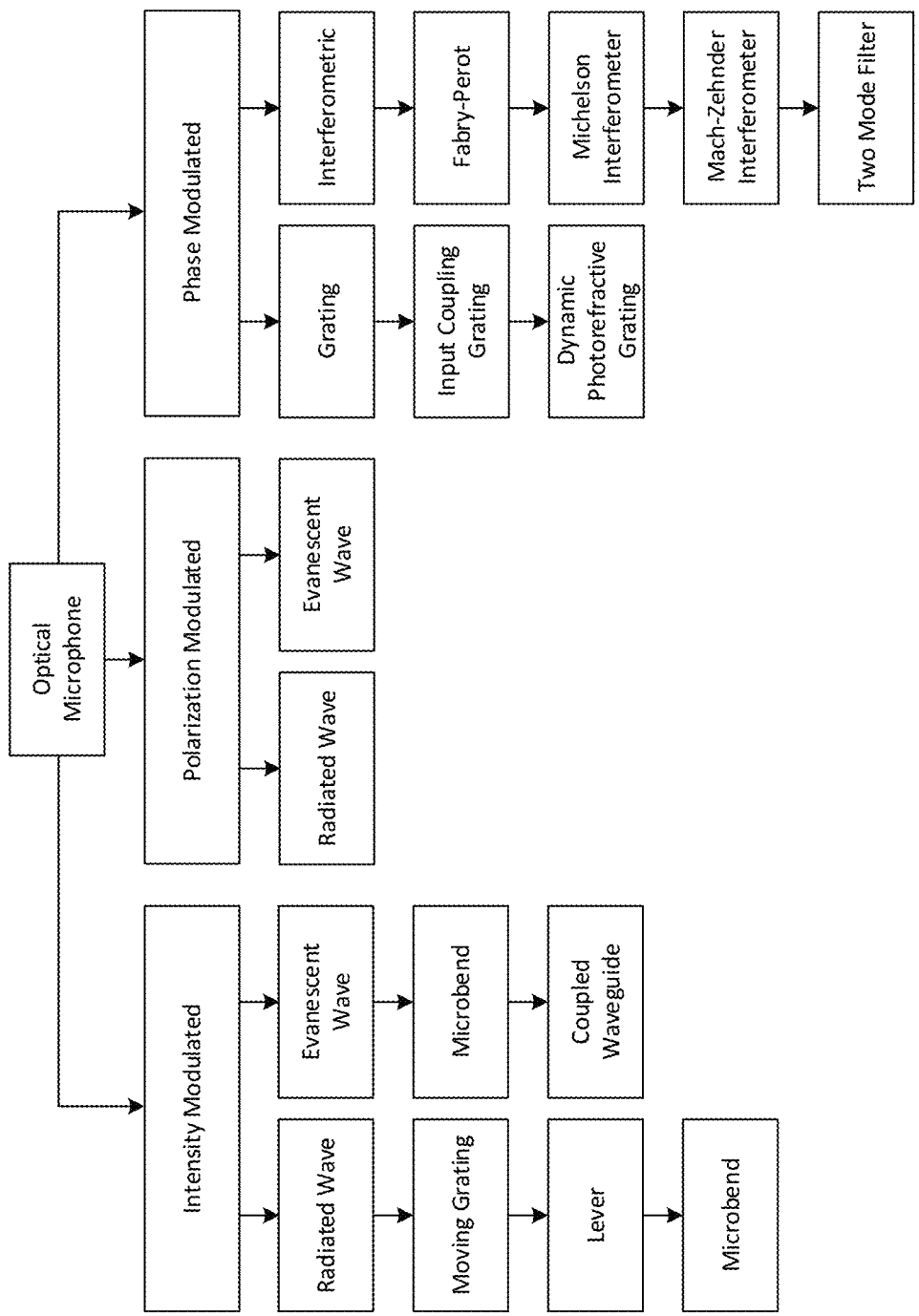
FIG. 11 is a block diagram depicting the different categories of optical microphone technology that are compatible with the workstation, in accordance with some embodiments.

The optical microphone described in this disclosure is representative of a type of microphone which uses an optical remote-pickup technology that senses the user's cheek or other membrane to detect skin vibrations induced during the speaking process. This provides an independent and reliable reference audio signal in any environment. Unlike conventional microphones, which only pick up airborne sound energy, the optical microphone picks up skin vibration speech energy by reflecting light from the cheek, forehead, or chin of the speaker to the optical microphone's sensor. There are multiple embodiments of the optical microphone that can provide this remote sensing functionality and can be described in terms of the modulation mechanism being adopted as shown in FIG. 11. The optical microphone described within this disclosure is representative, but not limited to, the type of intensity-modulated radiative wave of optical microphone referenced in FIG. 11.

Figure 12:
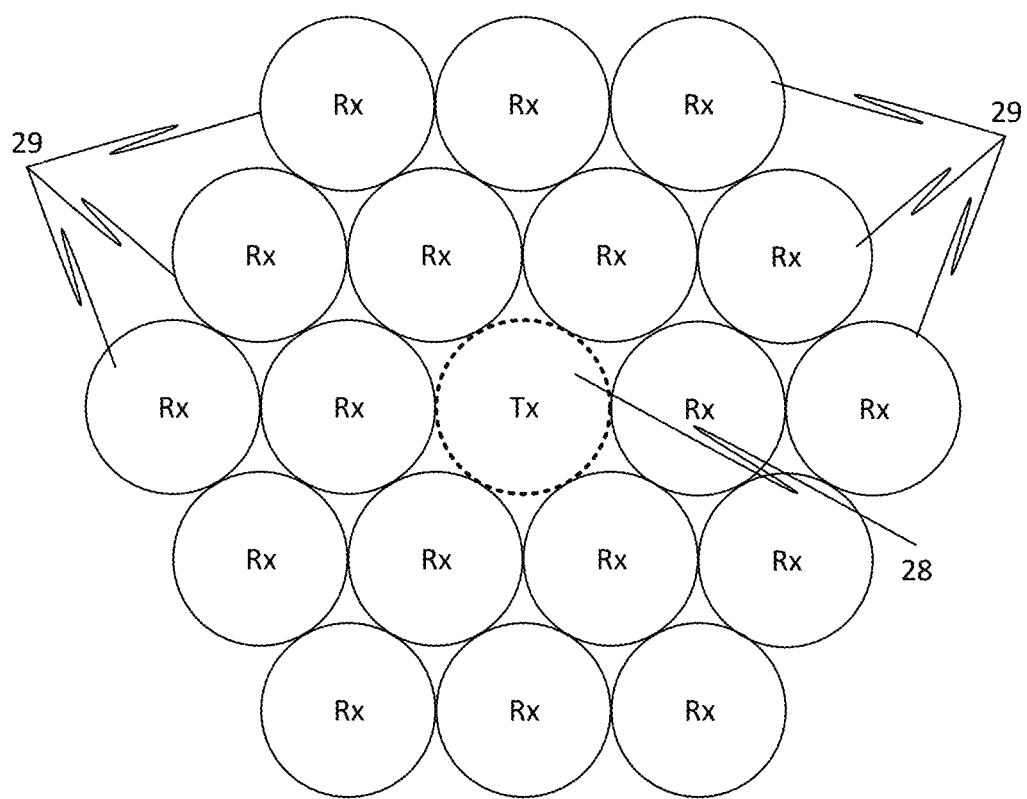
FIG. 12 is a diagram showing the cross-section of the optical fiber bundle used for transmission and receiving of the optical signals in the remote sensing configuration, in accordance with some embodiments.
Figure 13:
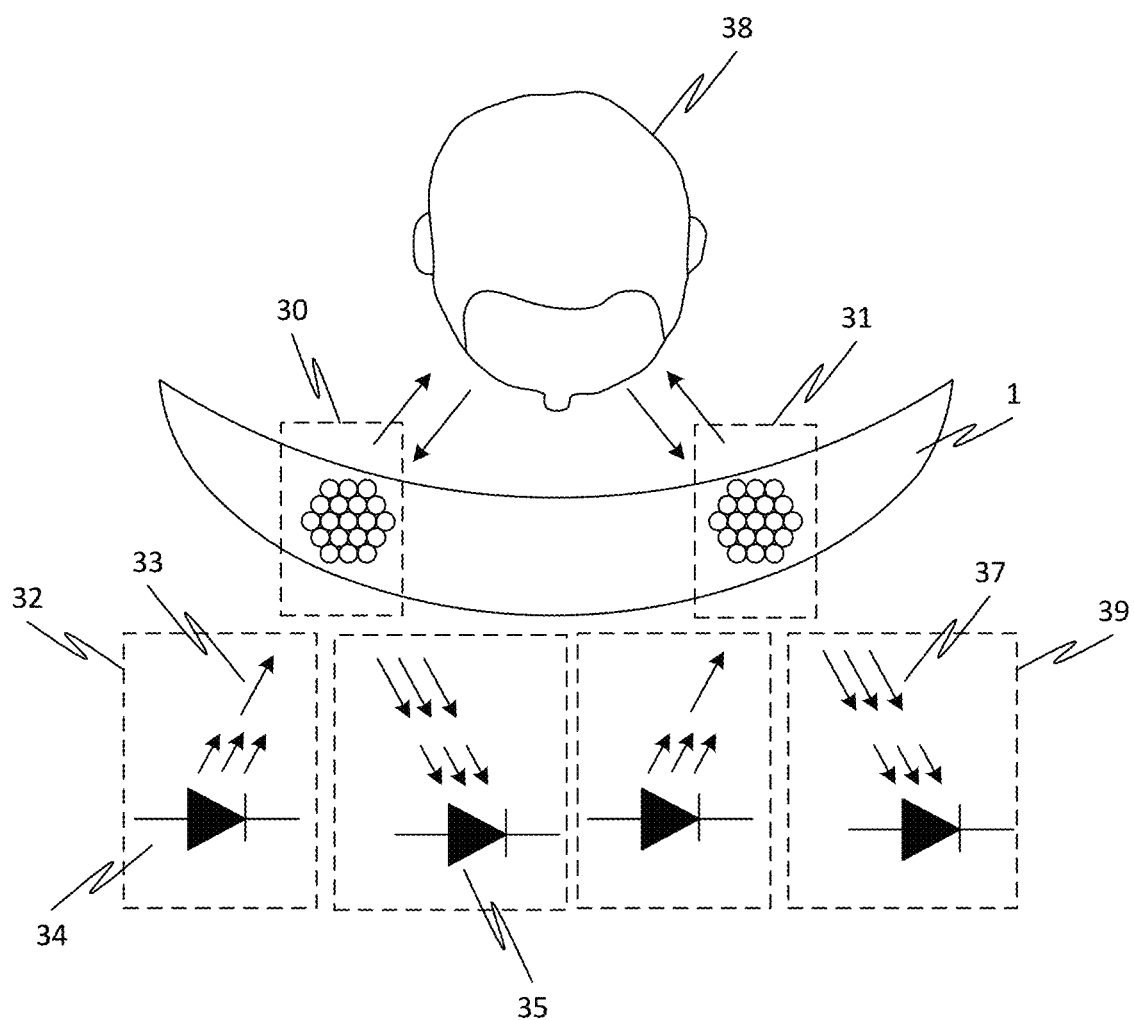
FIG. 13 is a system diagram of the optical microphone that is integrated into the stress-adaptive workstation embedded in the headrest and concentric near-head light field display chassis depicting the optical transmission and reception subsystems, in accordance with some embodiments.
Figure 14:
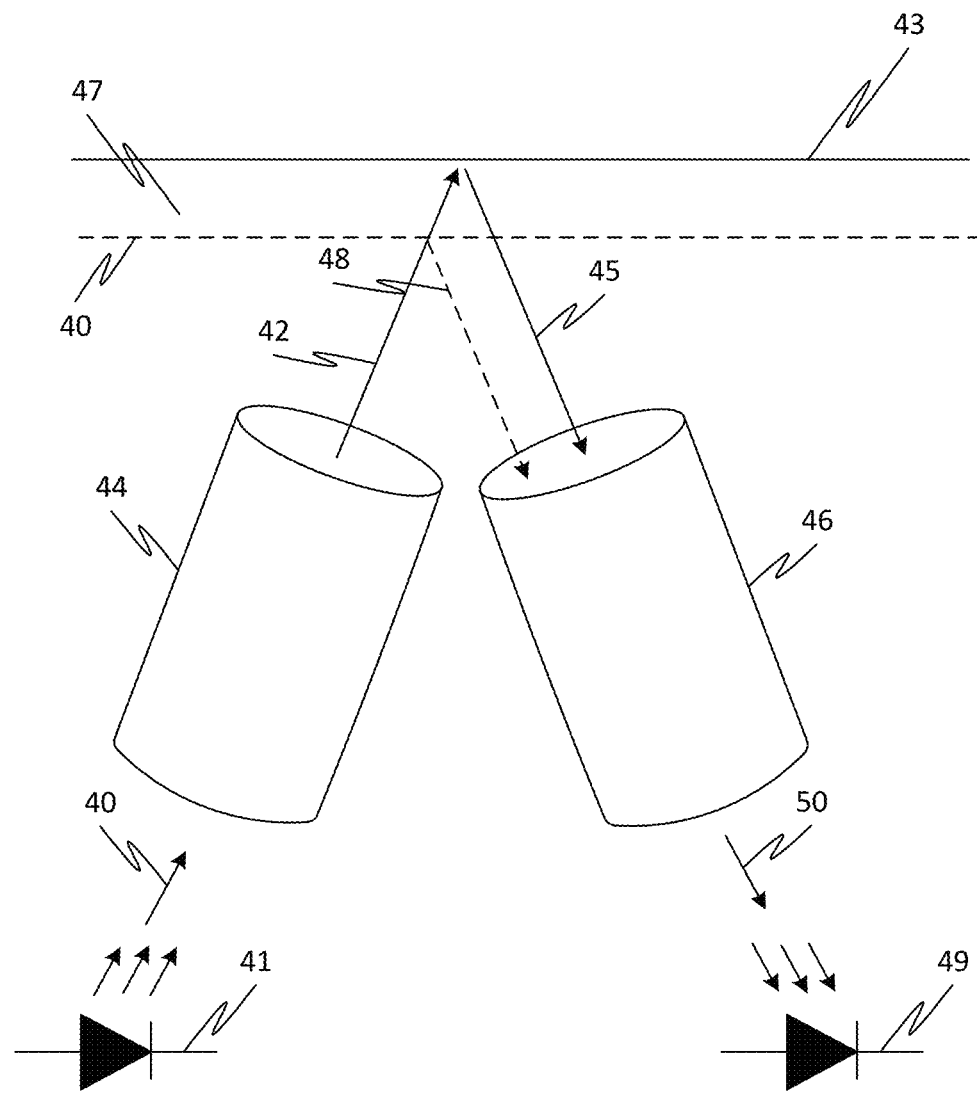
FIG. 14 is a system diagram depicting the principal operation of the optical microphone where deflection of the skin surface corresponds to different amounts of light coupled into the receiving fiber elements, in accordance with some embodiments.
Figure 15:
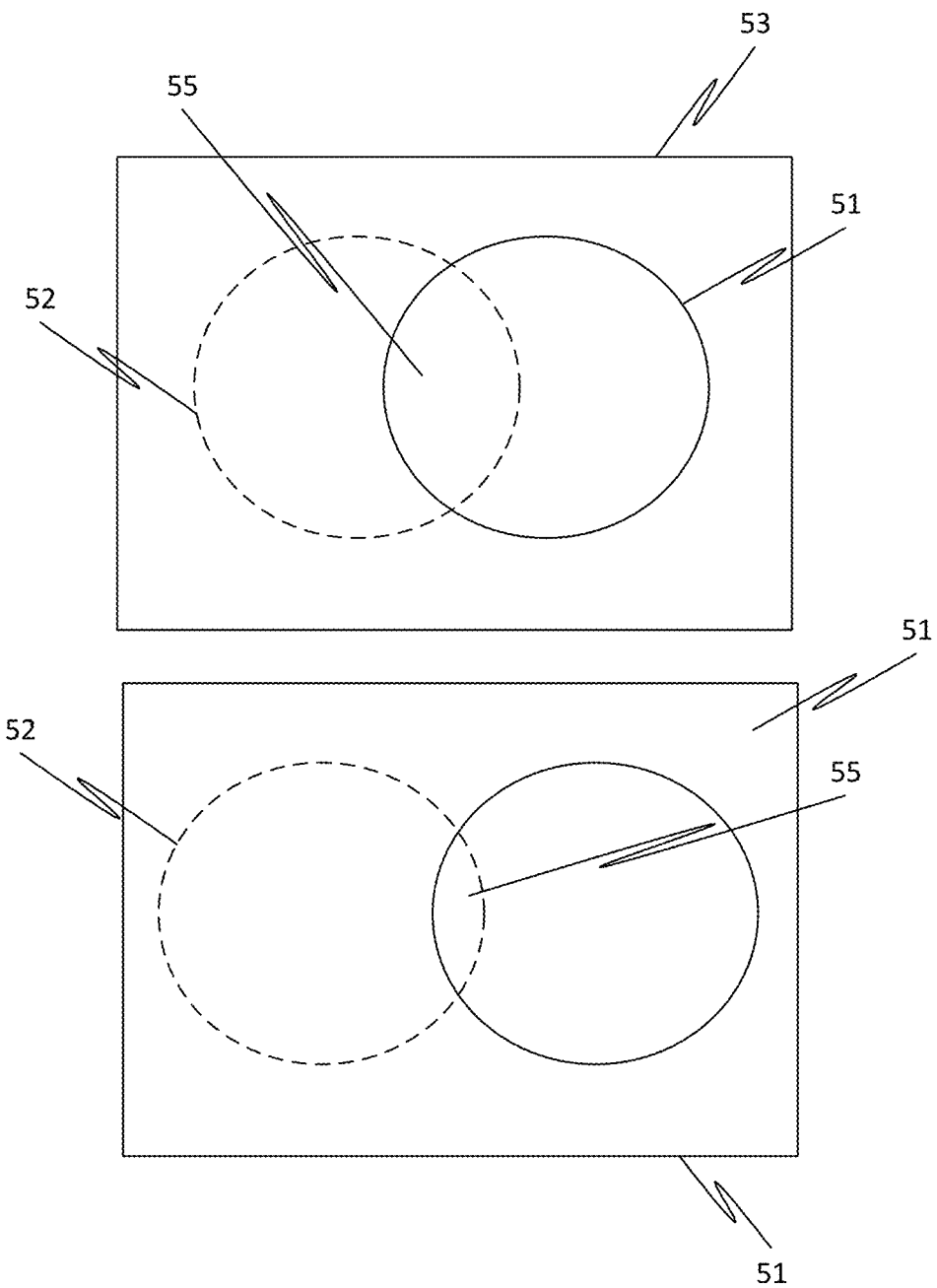
FIG. 15 is a diagram detailing the inter-fiber beam overlap area whose area is indicative of the amount of membrane deflection in the remote sensing system, in accordance with some embodiments.
Figure 16:
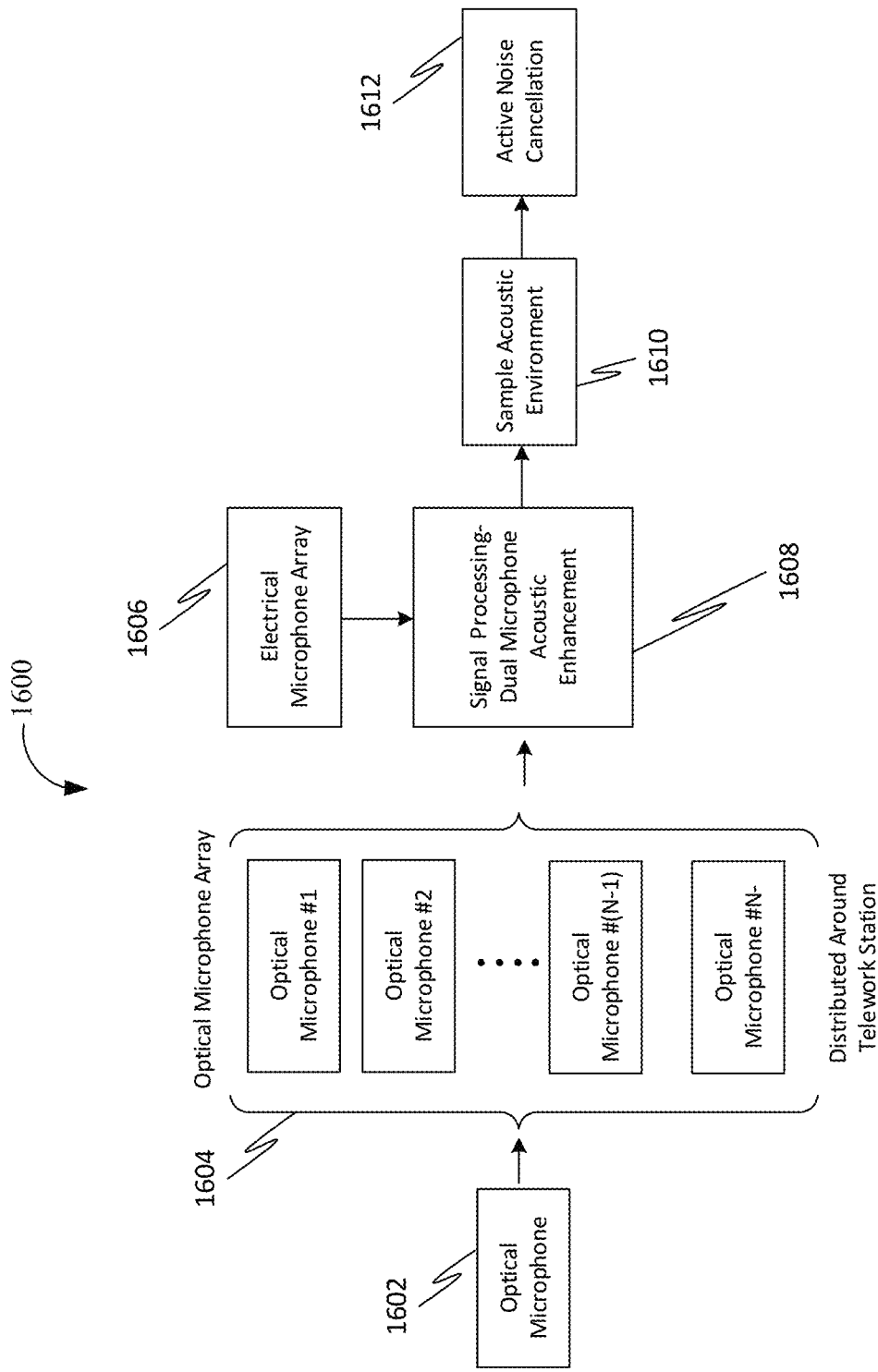
FIG. 16 is a block diagram of the extension from a single optical microphone into an array format to characterize the acoustic environment and support active noise cancellation sub-systems, in accordance with some embodiments.

The wave vibration power in air is much weaker than that in body tissues, which corresponds to the voice volume in the same tissue position being higher than the background noise. This is because skin/soft tissues vibrate mainly because of sound bouncing in the inner body vocal cords and not as a response to external acoustical signals/noise. Sound waves from outside the body create minimal vibrations inside the body soft tissues (0.001 fewer effects than from the inner voice). Integrating optical microphones of this type into the chassis of the concentric near-head display in close proximity to the user's face provides high levels of sensitivity with a large received signal-to-noise ratio (SNR) audio signal that is remotely sensed. FIG. 12 depicts the cross-sectional view of the optical fiber array integrated into the concentric near-head light field display chassis, where 28 represents the central transmitting optical fiber and 29 corresponds to the surrounding optical fibers in the array used for receiving of the reflected optical signals from the user. The optical fiber array is depicted in FIG. 12 is integrated into the concentric near-head display in different locations to facilitate different functionalities. FIG. 13 depicts this integration along with the transmission and receiving sub-systems that are used to launch and receive the user-modulated optical signals that are returned. FIG. 13 represents the two different optical microphone locations within the concentric near-head light field display to provide inputs for calibration, telecommunications, and active acoustic noise cancellation sub-systems. 34 depicts an optical source, 33 is an injection of light, and 32 is a sub-section that couples into the transmitting fiber of the fiber array. When the fiber-coupled source signal is modulated and reflected from the skin of the user's 38 forehead, chin, or cheek areas, the returning optical signals 37, are coupled into the receiver fibers in the fiber bundle and then optically detected, by a receiver photodiode 35 in the receiver block 39. Functionally, when a beam of light is incident on the human skin of the user, the beam of light will either be specularly reflected by the epidermis surface or refracted and transmitted into the skin. Surface specular reflection is roughly 5% and is a function of the angle of incidence. The diagram is shown in FIG. 14 describes the optical microphone functional concept, where light 40, from a light-emitting diode (LED) 41, is directed along a path 42 onto a reflective diaphragm 43, via a transmission fiber optic cable 44. The diaphragm reflects part of a light 45, into a receiver fiber optic cable 46. During a speech, the diaphragm is moved by sound signals that modulate the skin surface 47, causing the reflected light beam to be deflected 48, with the result that more or less light is coupled into the receiver fiber optic fiber element 46. At the end of the receiver fiber optic element (or cable) 46, a photodiode 49 converts the light intensity 50 variations into electrical signals. The circuitry has an audio frequency bandpass filter to filter out the lower frequency noise from the movements of the user. FIG. 15 provides a beam view perspective of the receiving optical fiber 51 relatives to a transmitting fiber 52, where the neutral 53 and deflected positions 54, depict the different amount of light coupled back through the receiver fibers and into the detector depending on the amount of membrane deflection. 55 represents the inter-fiber beam overlap area whose area is indicative of the amount of membrane deflection. Since the received light comes mostly from specular reflection of the skin, if the user moves his/her face or head or body, the directionality of the specular reflection may change notably, and the received signal may be significantly impacted. This, in some cases, can cause the SNR to go below a detectable range or induce high-frequency variations that have footprints in the lower audio range. For this reason, the optical microphone works in tandem with the embedded acoustic microphones in the system, and the final detection is done via a differential mechanism considering both the acoustic and optical inputs. The optical input, however, acts as a localized reference to help only pick up the user's voice. In some embodiments, instead of having an incoherent light sent and received through fibers; the light can be coherent laser light and receiver optics can be IR cameras capturing the interference patterns on the user's face to extract the acoustic vibrations. In such embodiments, more computational processing is needed to extract the acoustic signal, but the results may be more robust. Because of the compact size of the fiber-optic-array-based approach, the optical microphone can be distributed throughout the concentric near-head light field display chassis and stress-adaptive chair platform to provide an increased level of functionality. FIG. 16 shows this extension from a single element to an array format 1604, where combined observations using co-located electrical microphone arrays 1606 make it possible to now sample and characterize the acoustic environment that the user may be operating within under lower signal to noise conditions. Additionally, by characterizing the effective acoustic channel that the user may be operating within, active noise canceling methodologies can now be implemented to support telework teleconferencing activities.

FIG. 16 shows a system block diagram 1600 for facilitating, in accordance with some embodiments. Accordingly, the system 1600 may include an optical microphone 1602, an optical microphone array 1604, and an electrical microphone array 1606 communicatively coupled to a device 1608 configured for signal processing for dual microphone acoustic enhancement. Further, the device 1608 may be communicatively coupled to a device 1610 configured for sampling acoustic environment. Further, the device 1610 may be communicatively coupled to a device 1612 configured for performing active noise cancellation.

Figure 17:
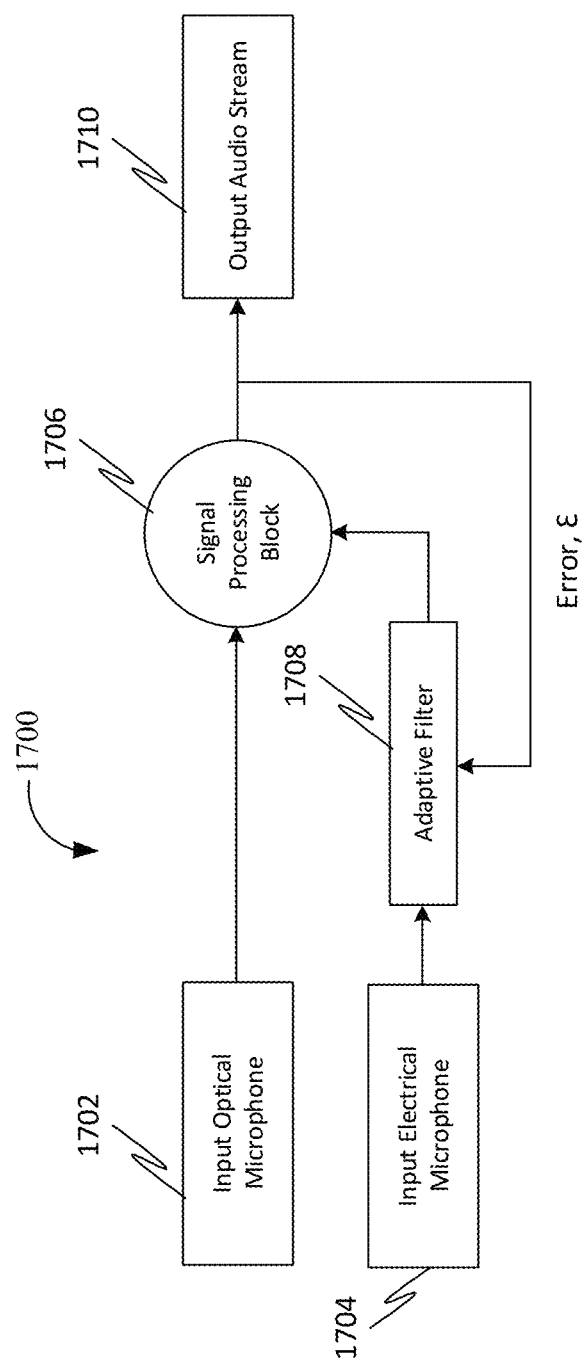
FIG. 17 is a block diagram representing the process for acoustic enhancement using dual microphone inputs with adaptive filtering and digital signal processing sub-functions, in accordance with some embodiments.

FIG. 17 shows a system 1700, in accordance with some embodiments. Accordingly, the system 1700 may include an input optical microphone 1702, an input electrical microphone 1704 communicatively coupled to a device 1706 configured for signal processing. Further, the input electrical microphone 1704 may be associated with an adaptive filter 1708. Further, the device 1706 may be configured for generating an output audio stream 1710.

A functional block diagram for the dual microphone acoustic enhancement block referenced from FIG. 16 is provided in FIG. 17 where the signal processing block can be implemented using a low-power audio codec processor to render adaptive algorithms such as, but not limited to, least mean square (LMS), normalized least mean square (NLMS), and blind source separation (BSS). The acoustic environment that the user may operate within is characterized using an impulse response (IR) based approach, leveraging the presence of the multiple microphones integrated into the concentric near-head light field display chassis and ergonomic stress-adaptive chair platform.

Figure 18:
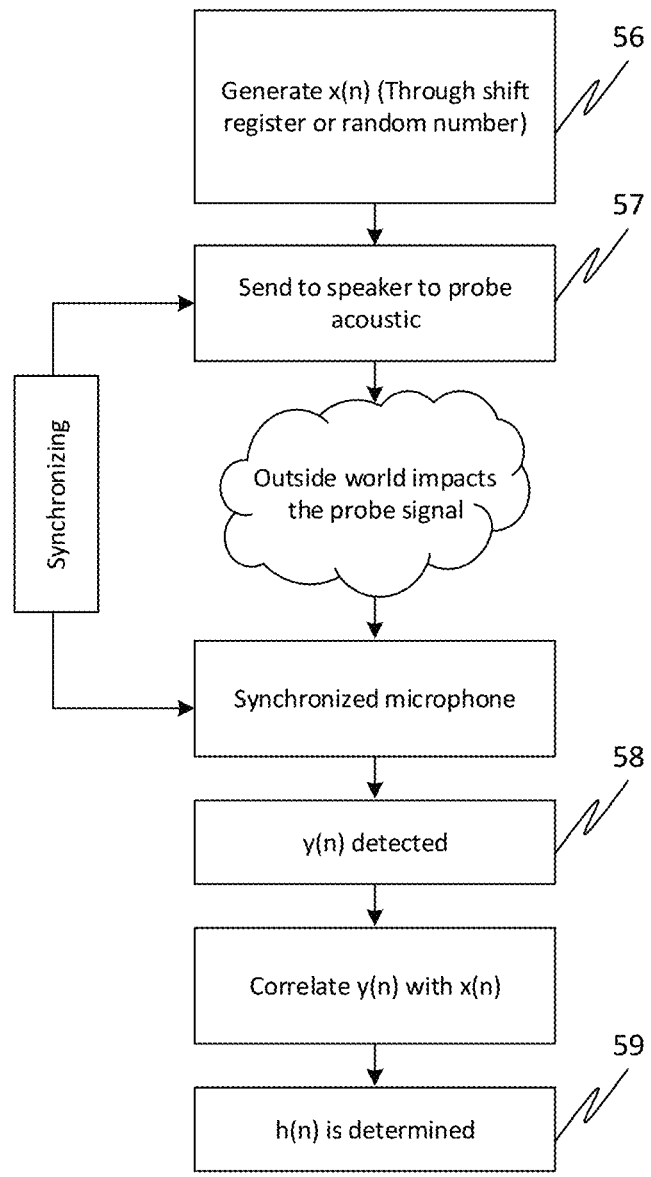
FIG. 18 is a block diagram representing the process invoked to determine the characteristic impulse response of the user's acoustic environment while using the workstation, in accordance with some embodiments.

FIG. 18 provides a block diagram depiction of the process used to discern the sampled versions of the impulse response, h(n) 59, based on the sampled version of the time-dependent acoustic source, x(n) 56, and signal sampled by the user as the receiver, y(n) 58. The correlation function, $R_{yx}$, between the signals x(t) and received by user y(t) is written as:

$$R_{yx}(\tau) = R_{xx}(\tau) * h(\tau). \quad (1)$$

where $R_{xx}$ is the auto-correlation of the signal x(t). When the autocorrelation of the input signal is proportional to the impulse of Dirac distribution, we have:

$$R_{xx}(\tau) = \sigma_x^2 \delta(\tau) \quad (2)$$

$$R_{yx}(\tau) = h(\tau) \sigma_x^2 \quad (3)$$

where $\sigma_x^2$ is the energy of the signal x(t). Consequently, the IR, h($\tau$), is obtained by a simple calculation of the correlation between the input-output signals.

In practice, the signals whose autocorrelation function approaches a Dirac distribution are the pseudo-random binary sequences (PRBSs). The signal of excitation x(n) is built starting from a periodic sequence PRBS of values 0 and 1 generated by an m-stage feedback register or a random generator. By suitably choosing the configuration of the shift register, one can generate a maximum length PRBS sequence of period $L = 2^m - 1$. This sequence of 0s and is 1s then converted into a set of ±V-volts rectangle pulses (rectangular function). The sampled version of the excitation signal, x(n), obtained is periodic with a period of $T = L/F_s$.

The sampled output signal, y(n), is in absence of additive noise of the same period as x(n). The sampled correlation function $R_{yx}(k)$, being of the same period as x(n) and y(n), can be calculated on an average of several periods L:

$$R_{yx}(k) = \left(\frac{1}{pL}\right) \sum_{n=1}^{pL} y(n) x(n-k) \quad (4)$$

where p indicates the number of periods L. The estimate of the impulse response is obtained by the following formula:

$$\frac{R_{yx}(k)}{\sigma_x^2} = h(n) \quad (5)$$

where k=1, . . . , N, and N is the estimated number of points. The estimate of $\sigma_x^2$ is given by:

$$\sigma_x^2 = \left(\frac{1}{pL}\right) \sum_{n=1}^{pL} x(n)^2 \quad (6)$$

The parameters in this method are the length L of the sequence, the number p of periods, and the size N of the identified IR.

Figure 19:
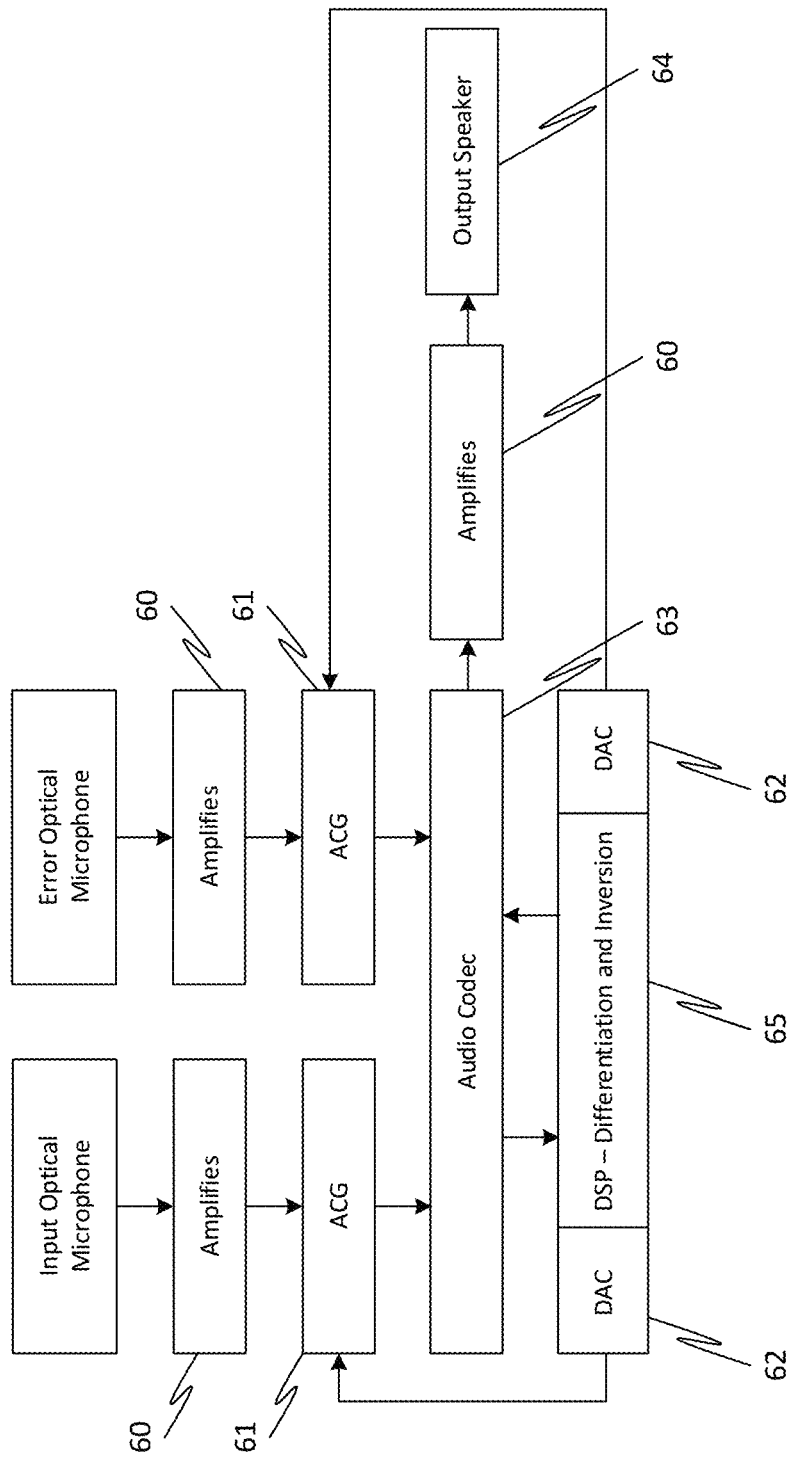
FIG. 19 is a block diagram representing the active noise cancellation scheme incorporated into the workstation, in accordance with some embodiments.

With the sampled version of the impulse response, h(n), characteristic of the user's acoustic environment, and using one of the optical microphone elements that is closer to the user as an error microphone, active control of the surrounding acoustic noise levels is performed using a signal-processing methodology that reduces the effective frequency-specific sound amplitude to improve the signal-to-noise ratio (SNR) so that unwanted noise is less perceptible. Active noise canceling (ANC) is based on coherent acoustics that accurately replicates the original sound field in all forms of the active noise canceling. Further, ANC uses amplifiers and microphones inside the workstation environment, along with digital signal processing (DSP) to cancel the noise. The sound can be described as a pressure wave consisting of an amplitude and a phase. A block diagram representation of the ANC method incorporated into the workstation described here is provided in FIG. 19. Both the input and error optical microphone outputs are fed into linear amplifiers 60, which are operated under an automatic gain control (AGC) configuration to ensure the linearity of the amplification process 61. This signal is conditioned via a digital-to-analog converter element 62, as a precursor to being processed by the DSP 65. The DSP processes the inverted version of the noise signals that are de-convolved with the error microphone signal prior to coding via an audio codec 63, to be sent to an output speaker 64.

The active noise-canceling system is incorporated within the chassis of the concentric near-head display, as well as within the ergonomic stress-adaptive chair platform. The embedded speaker device emits a wave with equal amplitude, but a phase of 180° (inverted phase, also known as anti-phase) of the original wave. The recombination process of the two waves is based on a physical principle called destructive interference. The ANC is achieved by using mixed-signal circuits or DSP, with a control algorithm to analyze the sound's waveform, to generate an amplified anti-phase wave to a transducer.

Figure 20:
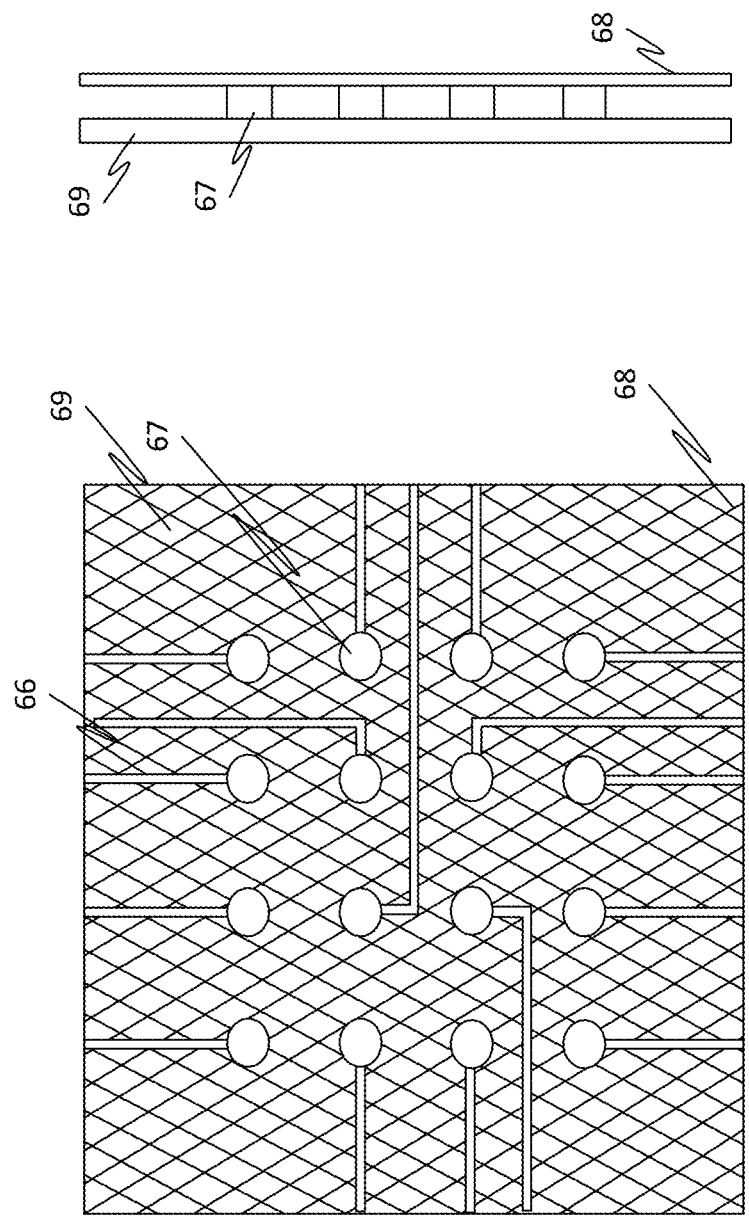
FIG. 20 is a depiction of the tactile high frequency massaging functionality for stress-adaptive strain relief and ergonomic adjustments using embedding of tactile acoustic transducer elements into the chair stress-transmission structure, in accordance with some embodiments.
Figure 21:
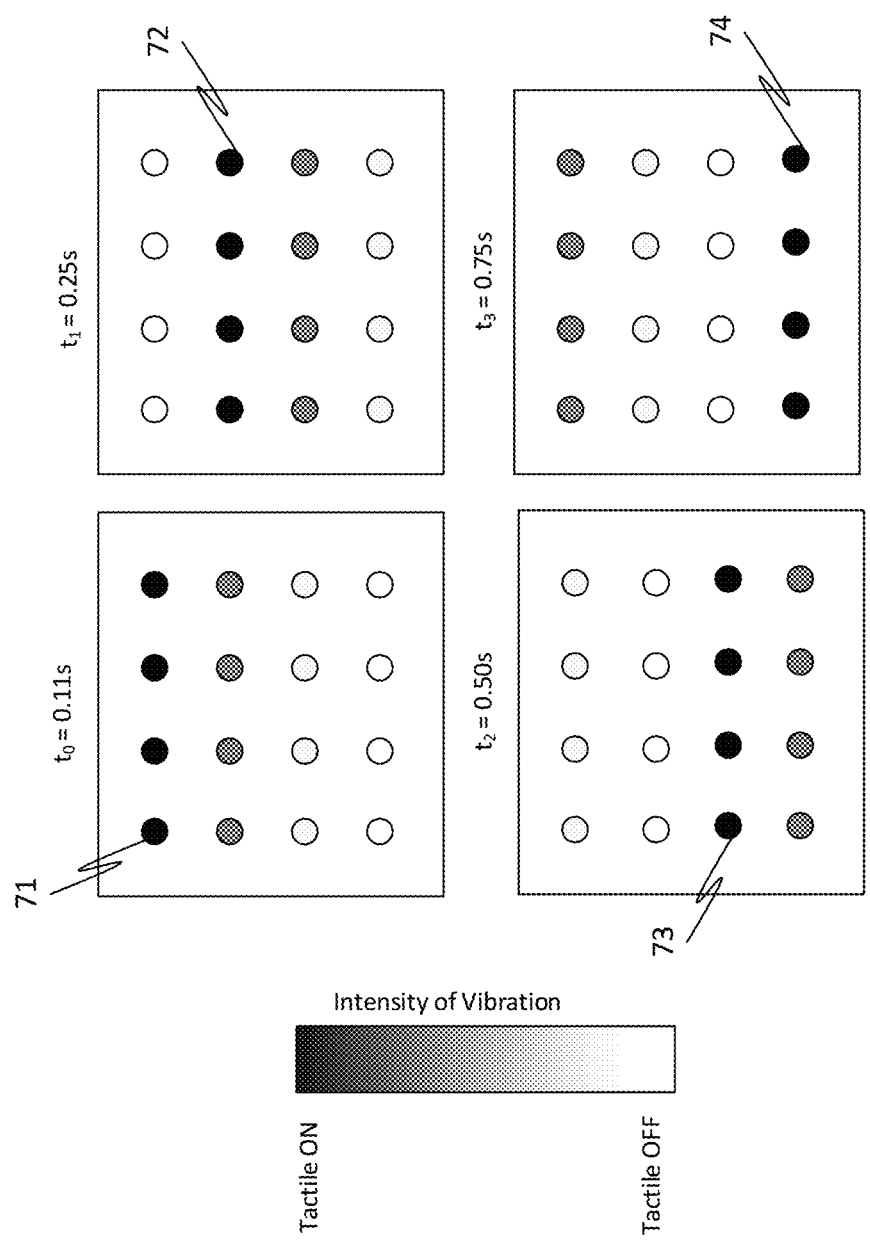
FIG. 21 is a schematic of the tactile-based stress-adaptive and strain reduction array operation to demonstrate ability to address individual elements of the actuator array and transmit vibrations through the mesh, in accordance with some embodiments.

The stress-adaptive workstation described here uses audio signals that are felt through touch and are heard through bone or tissue conduction to both provide low-frequency audio and to provide tactile high-frequency massaging functionality via embedding of tactile acoustic transducer elements into the chair platform. These frequencies (50-300 Hz) are high compared to massaging vibrators that operate in sub 50 Hz and are low compared to 2 KHz audible frequencies. These tactile acoustic transducers 67, are driven by the current coming from the driving circuit 66, shown in FIG. 20, where the array can produce a wide range of tactile and audible frequencies that can be coupled to a mesh of strings or fibers, 68, and that transmit that vibration to different spatial locations along the coupled surface, 68. In some embodiments, some of the transducers (or the tactile acoustic transducers) 67, might be used as tactile sensors to record the level and spatial profile of the stress that is given to the mesh at a certain position of the user to adaptively vibrate the areas that need relaxation or more blood flow. In some embodiments, the mesh that is coupled to the transducer array is an optical fiber which also helps in the sensing of the tensile stress between the nodes via the variations of the properties of the light passing through the fibers. In some embodiments, the mesh might be made with nylon material. The mesh is generally under tensile stress between the nodes. The mesh also helps to dampen the potential acoustic leakage of the vibrations in higher frequencies. The tactile transducers 67 don't need to be in a matrix-like array and can be distributed through the chair in such a manner to emphasize a certain ergonomic position depending on the application of the stress-adaptive station. Revitalizing of the lower and mid-back muscle areas via the acoustic transducer nodes embedded in the chair back and/or seat cushion can provide traveling or spot-based tactile perturbation for soothing tired or tense muscles in the area. Embedded heaters and/or coolers surrounding the acoustic transducer nodes provide an additional level of back muscle stress and strain reduction via targeted thermal transfer and mechanical wave transfer. The user feels as if some part of the mesh is stiffening and some parts are more flexible because of this adaptive change in the node frequencies which may overall adaptively reduce the stress. The ability to temporally sequence the activation of each independent transducer node in the array is enabled by the ability to independently activate each individual transducer element using the serial wiring 66 driving approach, where 69 is the circuit backplane insulating layer. This operation of a linear time-dependent 4×4 transducer array is provided in FIG. 21 where the strength of the tactile actuation has an intensity variation represented in grayscale. Each row of the array can be addressed as indexed by 71 for the top row, 72 for the second row, 73 for the third row, and 74 for the bottom row.

Figure 22:
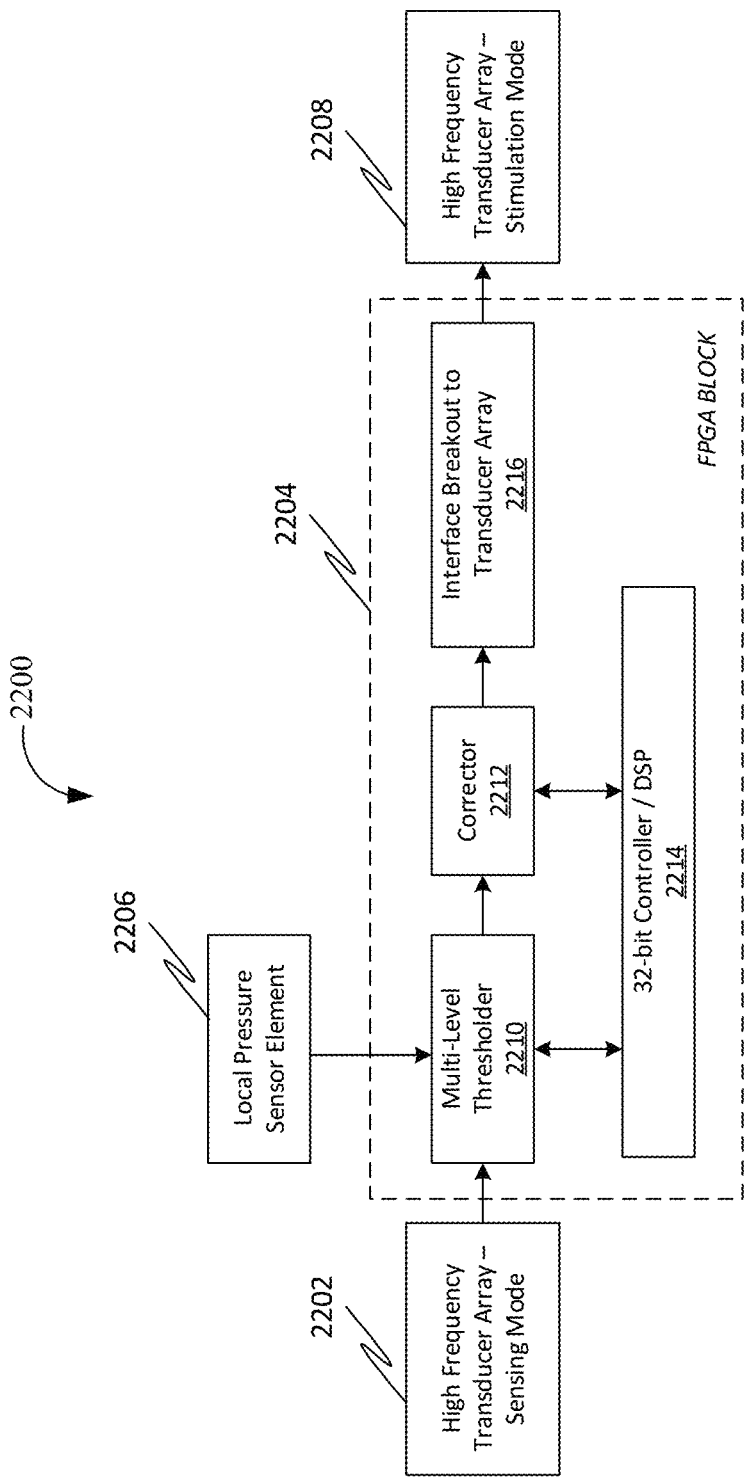
FIG. 22 is a block diagram representation of this process where the high-frequency transducer array is operated in a sensing mode as a precursor to operating in a stimulated mode of operation, in accordance with some embodiments.

FIG. 22 illustrates a system 2200 for facilitating high-frequency transducer applications, in accordance with some embodiments. Accordingly, the system 2200 may include a high-frequency transducer array 2202 in a sensing mode, a field programmable gate array (FPGA) block 2204, a local pressure element 2206, and a high-frequency transducer array 2208 in a stimulation mode. Further, the FPGA block 2204 may include a multi-level thresholder 2210, a corrector 2212, a 32-bit controller 2214, and an interface breakout to transducer array 2216.

Figure 23:
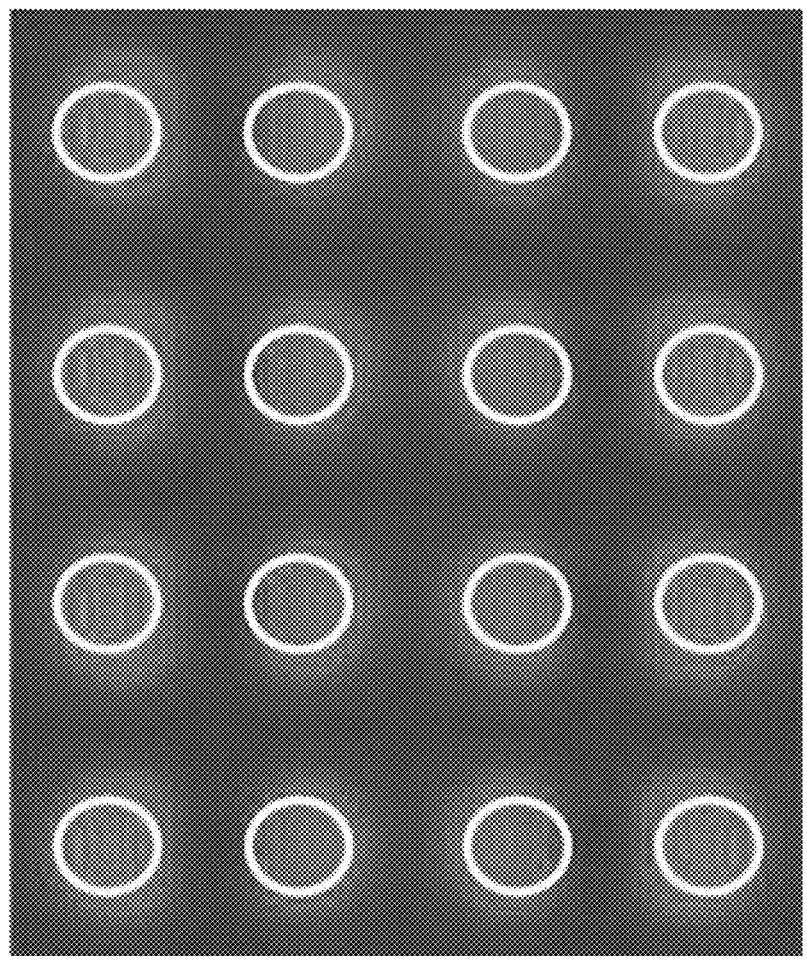
FIG. 23 is a diagram showing the pressure map generated from the transducer array and associated resistive-based pressure sensing mechanism, in accordance with some embodiments.

Resistive-based pressure sensing contact pattern areas surrounding the individual high-frequency transducer array elements provide heat map characterization of the pressure contact areas between the user and chair supports that are used to selectively target and stimulate areas of fatigue and stress. FIG. 22 depicts a block diagram representation of this process where the high-frequency transducer array is initially operated in a sensing mode where the local pressure sensor elements are calibrated using a multi-level thresholding approach to create a user-specific pressure map on the chair support areas. The 32-bit controller and DSP use the calibration pressure map to determine which individual transducer array elements need to be activated with the highest level of stimulation where stimulation strength is directly proportional to the pressure level. An example of this heat map is depicted in FIG. 23 where the pressure contour map is superimposed on the geometrical layout of the individual transducer array elements. These values are output to the interface breakout for the transducer array to operate the high-frequency transducer array in a targeted, stimulation mode.

Figure 24:
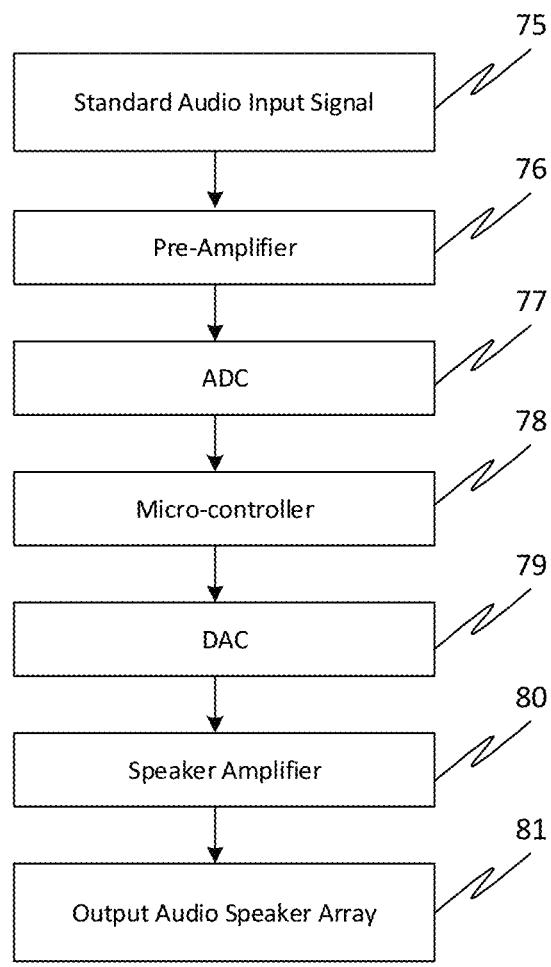
FIG. 24 is a block diagram depiction of the directional audio system integrated into the chassis of the concentric near-head light field display, in accordance with some embodiments.

The acoustic audio system integrated into the chassis of the concentric near-head display is composed of a phased array of speakers that are fed from a single source of audio frequency sound but each speaker transmits the sound delayed by an amount which is determined by the distance between a particular speaker and a selected region in space, so that sound from each speaker constructively adds at the selected region in space. A sufficiently large number of speakers are employed so that when a sound reaches a region in space at the same moment in time the audio volume may be increased substantially over sound in regions where there is no constructive interference. FIG. 24 provides a block diagram representation of the directional audio system integrated into the chassis of the concentric near-head light field display using an underlying beam forming mechanism to tailor the acoustic experience of the user. A standard audio input signal 75, is conditioned prior to input into a micro-controller 78, using a pre-amplifier 76, to correctly bias an analogue to digital converter (ADC) 77. The micro-controller 78 sets the path delays, and corresponding phase shift between speaker elements, before reconverting to the analogue domain using a digital to analogue converter (DAC) 79, passing through a pre-amplifier 80, to serve as the input to the output audio speaker element 81.

This technique allows audio frequency sound to be heard in only selected regions within the room or other auditory space. Multiple regions with multiple soundtracks can be created by simultaneously playing variously delayed soundtracks over each of the speakers in the array. The sound may be either audio frequency sound, subsonic sound, or ultrasonic sound. The audio frequency sound falls within the range of 15 Hz to 20 kHz, the range generally of human hearing, with subsonic frequencies being those below 15 Hz, and ultrasonic frequencies being those above 20 kHz.

The beamforming technique used here is based on the principle of phased arrays and superposition, which states that the in-phase portions of two coincident waveforms may strengthen each other in constructive interference, while the out-of-phase portions may cancel each other out in destructive interference. An array of several speakers can produce a steerable beam of sound that is markedly more directional than the beam of a single speaker.

Figure 25:
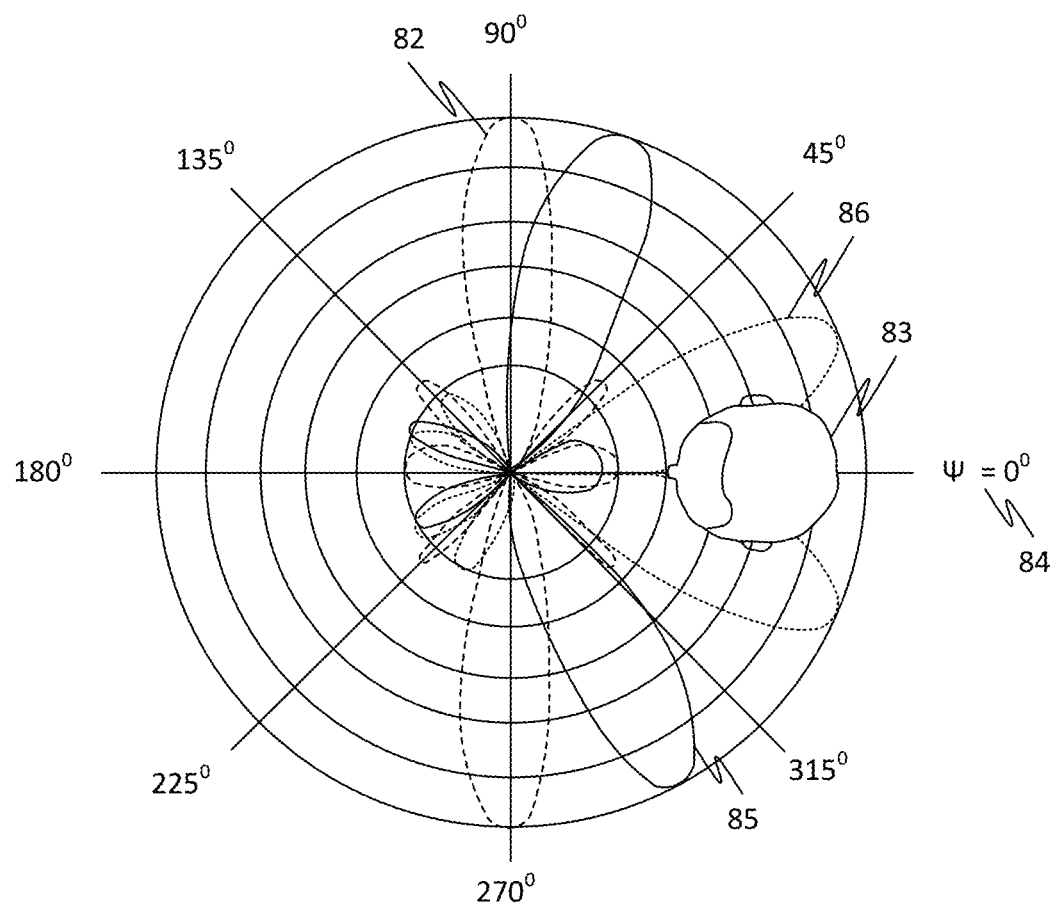
FIG. 25 shows the acoustic beamforming pattern with respect to the user position under different beamforming conditions, in accordance with some embodiments.

The beamforming strategy employed in this disclosure is to focus sound by delaying each loudspeaker relative to neighbors of each loudspeaker, such that each loudspeaker compensates for the phase differences between loudspeakers and creates constructive interference in the desired direction. A delay and sum beamformer (DSB) type are leveraged here due to the simplicity of the DSB and the DSB is also commonly regarded as a baseline for beamforming performance. In the DSB, the source signal is passed to each loudspeaker, and the vector of filter weights is given by:

$$q(\omega)=[e^{j\omega\tau_1},e^{j\omega\tau_2},\ldots,e^{j\omega\tau_L}]^T \qquad (7)$$

where $\tau_1, \tau_2, \ldots, \tau_L$ are the time delays applied to the sources, calculated by $$\tau_l = \frac{r_{max} - r_l}{c}; l = 1, 2, \ldots, L \qquad (8)$$

where $r_{max}=\max\{r_l\}$, $r_l$ is the distance between the $l^{th}$ loudspeaker and the reference point, and c is the speed of the sound wave. For the 5-element array used in this system with no time delays assigned to any of the individual speakers, FIG. 25 provides the acoustic beamforming angular characteristics showing the beamforming lobes 82, in a polar plot representation 84, that are not optimized for the user experience 83. By assigning integer values of phase delays (π/2) to each of the speaker elements, a more user-experience-optimized acoustic environment can be defined 85. Full optimization of the filter weights for the stress-adaptive workstation areas described here results in a beamforming pattern that has acoustic nodes that spatially overlap with the end-user 86. The optimization is done in such a way as to maximize the signal to the user while minimizing the leakage of the sound outside of the chair considering the U or V-shaped dampening systems behind the user's head. In some embodiments, an ultrasound carrier might be used to create a subwavelength localized sound for higher frequencies (above 500 Hz) and the lower frequencies are conducted to the user's body via the transducer array. This may create a high level of isolation of the sound leaking from inside of the system to outside of the system. However, the frequency performance might not be as good as the phased-array approach.

Figure 26:
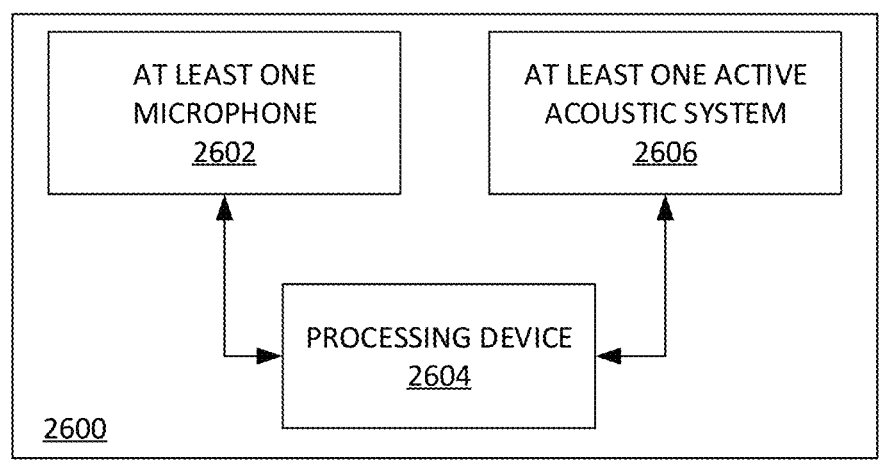
FIG. 26 is a block diagram of a system for facilitating acoustic noise management in a workstation, in accordance with some embodiments.

FIG. 26 is a block diagram of a system 2600 for facilitating acoustic noise management in a workstation, in accordance with some embodiments. Further, the workstation may include a chair. Further, the workstation may be configured to be utilized by a user. Further, the system 2600 may include at least one microphone 2602, a processing device 2604, and at least one active acoustic system 2606.

Further, the at least one microphone 2602 may be disposed on at least one portion of the workstation proximal to a head of the user. Further, the at least one portion may include a headrest of the workstation. Further, the at least one microphone 2602 may be configured for generating a sound profile of one or more first sounds associated with an environment of the workstation. Further, the sound profile may be characterized by at least one sound characteristic of the one or more first sounds. Further, the at least one sound characteristic may include a frequency, an amplitude, a spectrum, a duration, an envelope, a location, etc. Further, the sound profile may include at least one spectral content of the one or more first sounds.

Further, the processing device 2604 may be communicatively coupled with the at least one microphone 2602. Further, the processing device 2604 may be configured for analyzing the sound profile. Further, the processing device 2604 may be configured for generating at least one signal based on the analyzing.

Further, the at least one active acoustic system 2606 may be communicatively coupled with the processing device 2604. Further, the at least one active acoustic system 2606 may be configured for generating one or more second sounds based on the at least one signal. Further, the one or more seconds sounds may include the at least one sound characteristic. Further, the at least one active acoustic system 2606 may include at least one speaker. Further, the at least one speaker may be disposed on the workstation.

Figure 27:
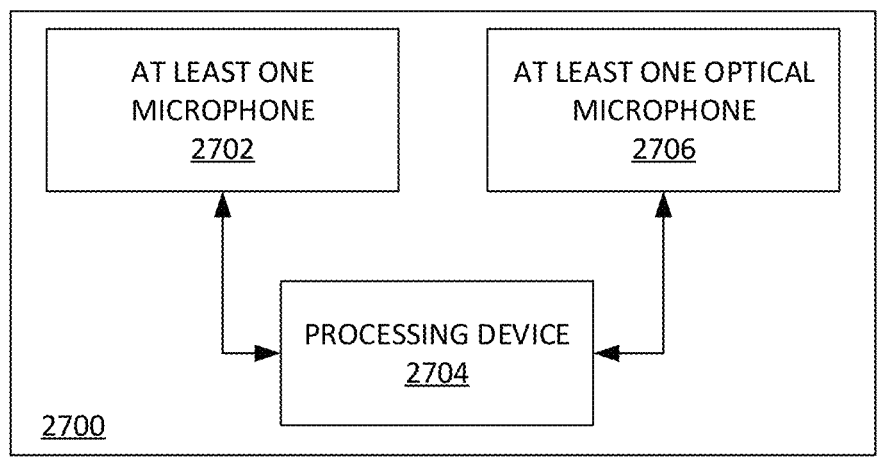
FIG. 27 is a block diagram of a system for facilitating acoustic noise management in the workstation, in accordance with some embodiments.

FIG. 27 is a block diagram of a system 2700 for facilitating acoustic noise management in the workstation, in accordance with some embodiments. Further, the workstation may include a chair. Further, the workstation may be configured to be utilized by a user. Further, the workstation may include a concentric light field near-head display disposed on the workstation proximal to a face of the user. Further, the concentric light field near-head display may be an apparatus for facilitating optical fusion of light field. Further, the apparatus may include at least two display devices, at least one bent reflector, and at least one curved reflector. Further, the concentric light field near-head display may be associated with a field of view. Further, the face of the user may be disposed of in the field of view. Further, the system 2700 may include at least one optical microphone 2706, at least one microphone 2702, and a processing device 2704.

Further, the at least one optical microphone 2706 may be disposed on the concentric light field near-head display. Further, the at least one optical microphone 2706 may be configured for generating at least one first signal based on a change of at least one light characteristic of light associated with at least one portion of the face. Further, the at least one portion of the face may be disposed of in the field of view. Further, the change of the at least one light characteristic may be based on at least one movement of the at least one portion of the face. Further, the at least one movement of the at least one portion of the face may be based on one or more user sounds produced by the user. Further, the user may produce the one or more user sounds by performing at least one action. Further, the at least one light characteristic may include an intensity, a polarization, a frequency, a wavelength, etc. Further, the at least one portion of the face may include a cheek, a chin, a lip, a nose, a forehead, etc. Further, the at least one movement may include a vibration. Further, the at least one action may include speaking.

Further, the at least one microphone 2702 may be disposed on at least one portion of the workstation proximal to a head of the user. Further, the at least one portion may include a headrest of the workstation. Further, the at least one microphone 2702 may be configured for generating at least one second signal based on one or more environment sounds associated with the workstation. Further, the one or more environment sounds may include the one or more user sounds and one or more noise.

Further, the processing device 2704 may be communicatively coupled with the at least one optical microphone 2706 and the at least one microphone 2702. Further, the processing device 2704 may be configured for analyzing the at least one second signal based on the at least one first signal. Further, the processing device 2704 may be configured for extracting the one or more user sounds from the one or more environment sounds based on the analyzing.

Further, in some embodiments, the processing device 2704 may be configured for generating at least one audio signal corresponding to the one or more user sounds based on the extracting. Further, the system 2700 may include a communication device 2708 communicatively coupled with the processing device 2704. Further, the communication device 2708 may be configured for transmitting the at least one audio signal to at least one device. Further, the at least one device may be configured for generating the one or more user sounds based on the at least one audio signal.

Figure 28:
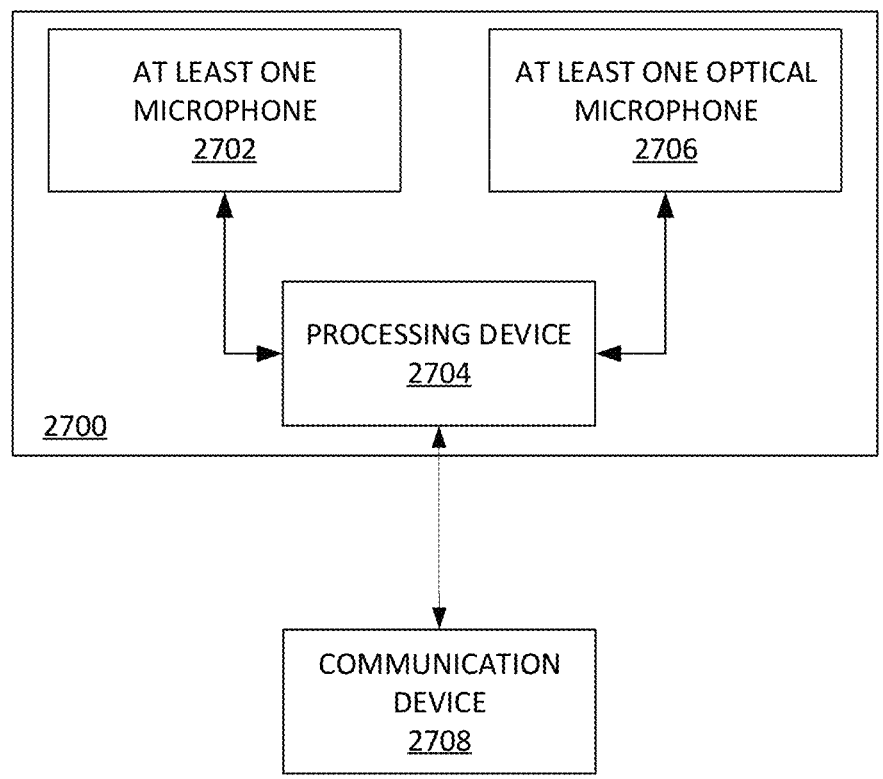
FIG. 28 is a block diagram of a system for facilitating acoustic noise management in the workstation, in accordance with some embodiments.

FIG. 28 is a block diagram of the system 2700 for facilitating acoustic noise management in the workstation, in accordance with some embodiments, which includes a two-way communication device 2708.

Figure 29:
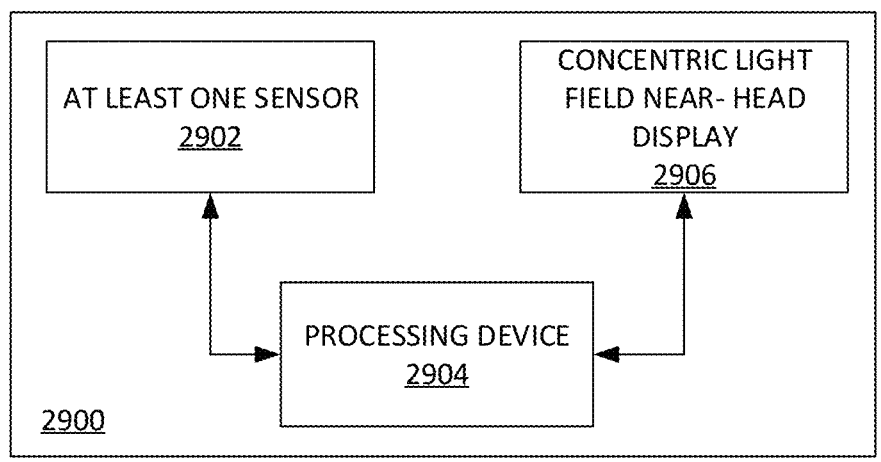
FIG. 29 is a block diagram of a system for facilitating display management in the workstation, in accordance with some embodiments.

FIG. 29 is a block diagram of a system 2900 for facilitating display management in the workstation, in accordance with some embodiments. Further, the workstation may include a chair. Further, the workstation may be configured to be utilized by a user. Further, the workstation may include at least one movement mechanism. Further, the at least one movement mechanism may be comprised in the workstation. Further, the workstation may be configured for receiving at least one interaction from the user. Further, the at least one interaction may include at least one action performed on the chair. Further, the at least one interaction may include a change in a posture of the user. Further, the at least one movement mechanism may be configured for providing at least one movement to the workstation based on the receiving of the at least one interaction. Further, the at least one movement may include a translatory movement, a rotatory movement, a tilting movement, a telescopic movement, etc. Further, the at least one movement may be at least one of the translatory movement, the rotatory movement, the tilting movement, and the telescopic movement. Further, the workstation may be configured for transitioning between at least one of a plurality of positions and a plurality of orientations based on the at least one movement. Further, the system 2900 may include at least one sensor 2902, a processing device 2904, and a concentric light field near-head display 2906.

Further, the at least one sensor 2902 may be disposed on the workstation. Further, the at least one sensor 2902 may be configured for generating sensor data based on the at least one movement of the workstation.

Further, the processing device 2904 may be communicatively coupled with the at least one sensor 2902. Further, the processing device 2904 may be configured for analyzing the sensor data. Further, the processing device 2904 may be configured for generating at least one command based on the analyzing.

Further, the concentric light field near-head display 2906 may be communicatively coupled with the processing device 2904. Further, the concentric light field near-head display 2906 may be disposed on the workstation proximal to a face of the user. Further, the concentric light field near-head display 2906 may be an apparatus for facilitating optical fusion of a light field. Further, the apparatus may include at least two display devices, at least one bent reflector, and at least one curved reflector. Further, the concentric light field near-head display 2906 may be associated with a field of view. Further, the face of the user may be disposed of in the field of view. Further, the concentric light field near-head display 2906 may be configured for displaying at least one content on the concentric light field near-head display 2906. Further, the at least one content may include at least one digital content. Further, the at least one digital content may include at least one document, at least one image, at least one audio, at least one video, etc. Further, the concentric light field near-head display 2906 may be configured for modifying the at least one content based on the at least one command.

Further, in some embodiments, the at least one content may include a plurality of contents. Further, the plurality of contents may correspond to the at least one of the plurality of positions and the plurality of orientations. Further, the modifying may include transitioning between the plurality of contents based on the at least one movement.

Figure 30:
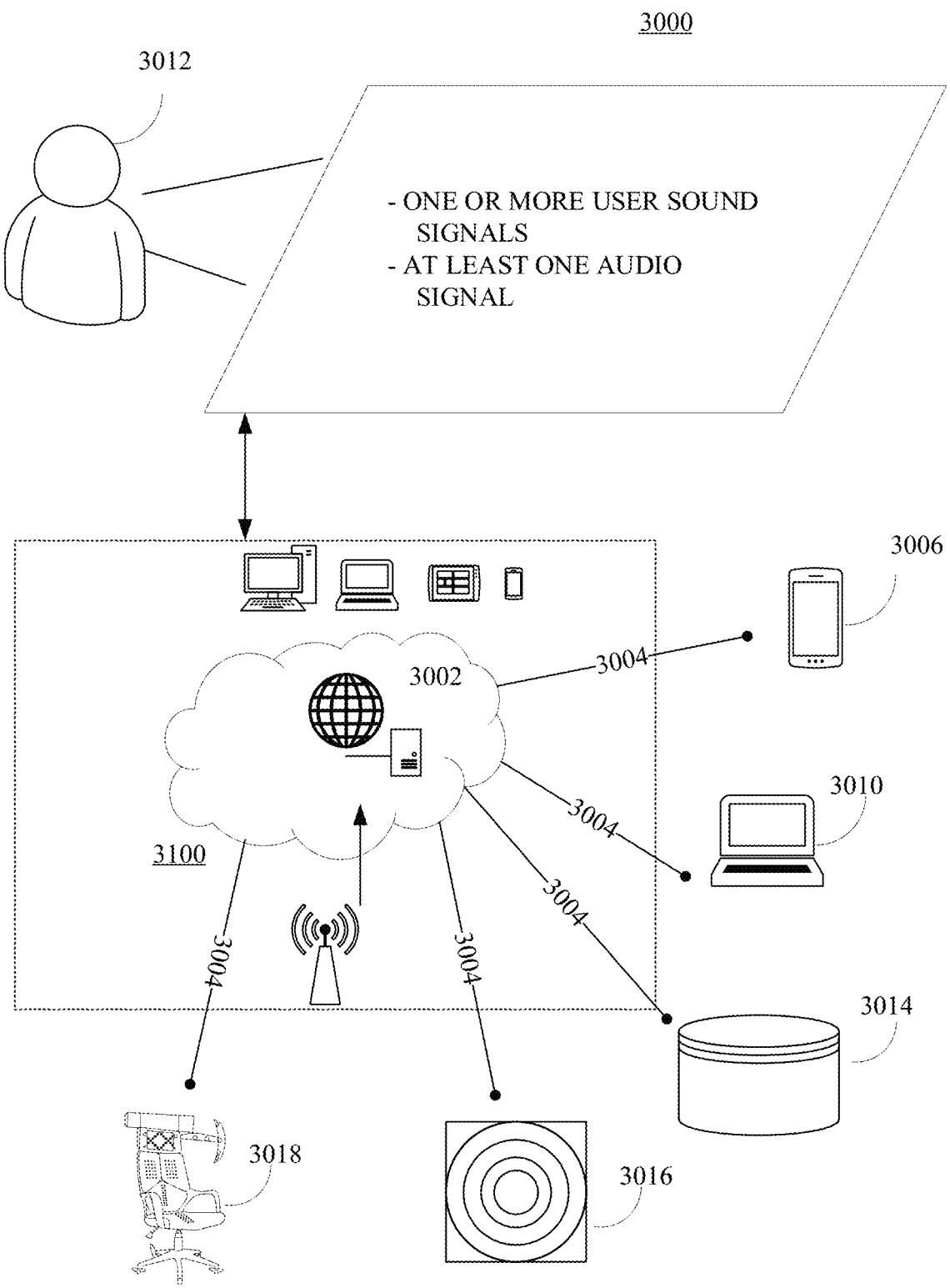
FIG. 30 is an illustration of an online platform consistent with various embodiments of the present disclosure.

FIG. 30 is an illustration of an online platform 3000 consistent with various embodiments of the present disclosure. By way of non-limiting example, the online platform 3000 for facilitating stress adaption in a workstation may be hosted on a centralized server 3002, such as, for example, a cloud computing service. The centralized server 3002 may communicate with other network entities, such as, for example, a mobile device 3006 (such as a smartphone, a laptop, a tablet computer, etc.), other electronic devices 3010 (such as desktop computers, server computers, etc.), databases 3014, sensors 3016, or an apparatus 3018 (such as a workstation 3203) over a communication network 3004, such as, but not limited to, the Internet. Further, users of the online platform 3000 may include relevant parties such as, but not limited to, end-users, administrators, service providers, service consumers and so on. Accordingly, in some instances, electronic devices operated by the one or more relevant parties may be in communication with the platform.

A user 3012, such as the one or more relevant parties, may access online platform 3000 through a web-based software application or browser. The web-based software application may be embodied as, for example, but not be limited to, a website, a web application, a desktop application, and a mobile application compatible with a computing device 3100.

Figure 31:
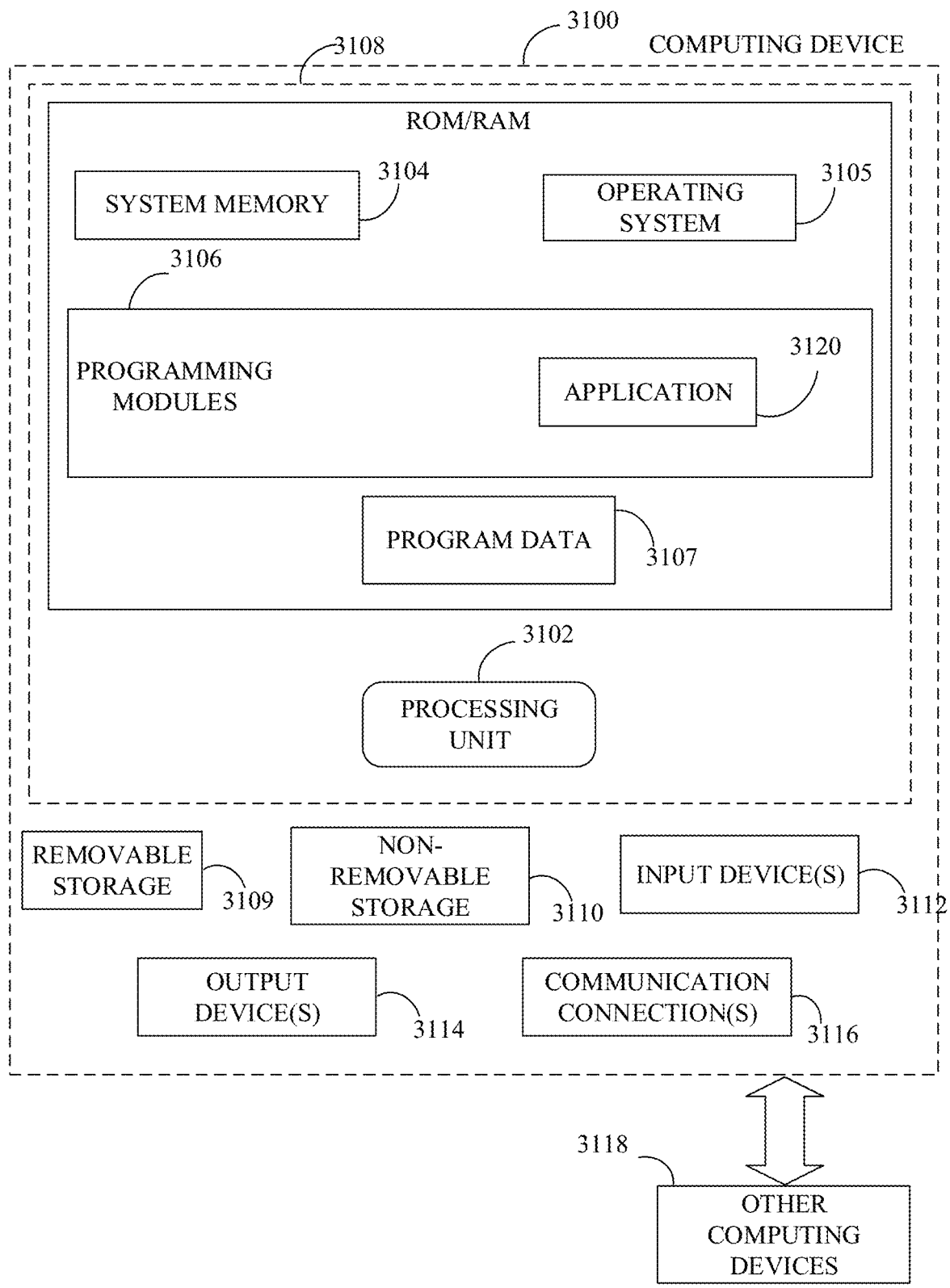
FIG. 31 is a block diagram of a computing device for implementing the methods disclosed herein, in accordance with some embodiments.

With reference to FIG. 31, a system consistent with an embodiment of the disclosure may include a computing device or cloud service, such as computing device 3100. In a basic configuration, a computing device 3100 may include at least one processing unit 3102 and a system memory 3104. System memory 3104 may be a non-transitory computer-readable storage medium. Depending on the configuration and type of computing device, system memory 3104 may comprise, but is not limited to, volatile (e.g., random-access memory (RAM)), non-volatile (e.g., read-only memory (ROM)), flash memory, or any combination. System memory 3104 may include operating system 3105, one or more programming modules 3106, and may include a program data 3107. Operating system 3105, for example, may be suitable for controlling computing device 3100's operation. In some embodiments, programming modules 3106 may include an image-processing module or a machine learning module. Furthermore, embodiments of the disclosure may be practiced in conjunction with a graphics library, other operating systems, or any other application program, and is not limited to any particular application or system. This basic configuration is illustrated in FIG. 31 by those components within a dashed line 3108.

A processor may include other types of programming modules. For example a receive image module is configured to receive images captured by a camera. A virtual image module is configured to incorporate information from the image into a virtual image; an output module is configured to instruct the virtual display system to output the virtual image; a positioning and motion tracking modules are configured to determine the geometry of an object based on sensor data or track the motion of an object; and transducer signaling and feedback modules are configured to control transducers or receive signals from the transducers; and noise suppression modules are configured to generate noise suppression signals based on environmental noise.

Computing device 3100 may have additional features or functionality. For example, computing device 3100 may also include additional data storage devices (removable and/or non-removable) such as, for example, magnetic disks, optical disks, or tape. Such additional storage is illustrated in FIG. 31 by a removable storage 3109 and a non-removable storage 3110. Computer storage media may include volatile and non-volatile, or removable and non-removable media implemented in any method or technology for storage of information, such as computer-readable instructions, data structures, program modules, or other data. System memory 3104, removable storage 3109, and non-removable storage 3110 are all computer storage media examples (i.e., memory storage.) Computer storage media may include, but are not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 3100. Any such computer storage media may be part of device 3100. Computing device 3100 may also have input device(s) 3112 such as a keyboard, a mouse, a pen, a sound input device, a touch input device, a location sensor, a camera, a biometric sensor, etc. Output device(s) 3114 such as a display, speakers, a printer, etc. may also be included. The aforementioned devices are examples, and others may be used.

Computing device 3100 may also contain a communication connection 3116 that may allow device 3100 to communicate with other computing devices 3118, such as over a network in a distributed computing environment, for example, an intranet or the Internet. Communication connection 3116 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not a limitation, communication media may include wired media such as a wired network or direct-wired connection, and wireless media such as acoustic, radio frequency (RF), infrared, and other wireless media. The term "computer readable media" as used herein may include both storage media and communication media.

As stated above, a number of program modules and data files may be stored in system memory 3104, including operating system 3105. While executing on processing unit 3102, programming modules 3106 (e.g., application 3120 such as a media player) may perform processes including, for example, one or more stages of methods, algorithms, systems, applications, servers, databases as described above. The aforementioned process is an example, and processing unit 3102 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including, but not limited to, mechanical, optical, fluidic, and quantum technologies. In addition, embodiments of the disclosure may be practiced within a general-purpose computer or in any other circuits or systems. Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, microcode, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list) include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Figure 32:
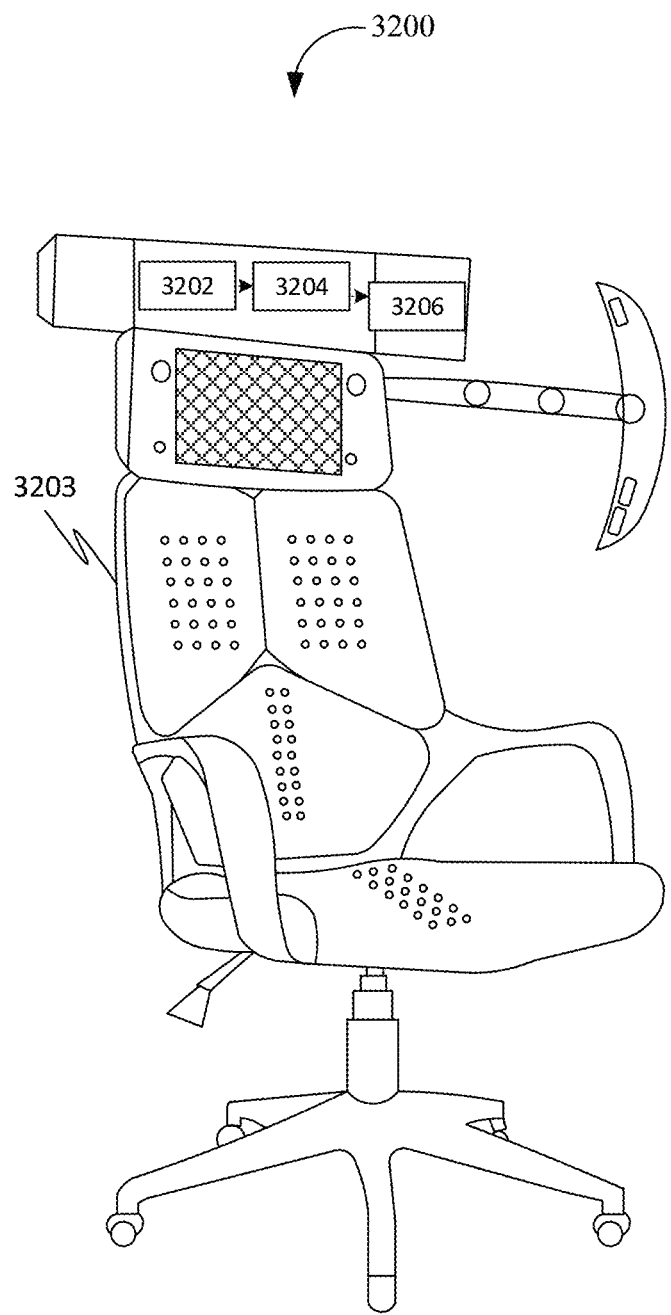
FIG. 32 is a schematic of a system for facilitating stress adaption in a workstation, in accordance with some embodiments.

FIG. 32 is a schematic of a system 3200 for facilitating stress adaption in a workstation 3203, in accordance with some embodiments. Accordingly, the system 3200 may include one or more microphones 3202 disposed on the workstation 3203. Further, the one or more microphones 3202 may be configured for generating one or more first sound signals of one or more first sounds associated with an environment of the workstation 3203. Further, the system 3200 may include a processing device 3204 communicatively coupled with the one or more microphones 3202. Further, the processing device 3204 may be configured for analyzing the one or more first sound signals. Further, the processing device 3204 may be configured for determining one or more first sound characteristics of the one or more first sounds based on the analyzing of the one or more first sound signals. Further, the one or more first sound characteristics may include a frequency, a phase, an amplitude, a spectrum, a duration, an envelope, a location, etc., of the one or more first sounds. Further, the processing device 3204 may be configured for determining one or more second sound characteristics of one or more second sounds based on the determining of the one or more first sound characteristics. Further, the one or more second sound characteristics may include a frequency, a phase, an amplitude, a spectrum, a duration, an envelope, a location, etc. of the one or more second sounds. Further, the processing device 3204 may be configured for generating one or more second sound signals for the one or more second sounds based on the determining of the one or more second sound characteristics of the one or more second sounds. Further, the system 3200 may include one or more acoustic devices 3206 disposed on the workstation 3203. Further, the one or more acoustic devices 3206 may be communicatively coupled with the processing device 3204. Further, the one or more acoustic devices 3206 may be configured for emitting the one or more second sounds based on the one or more second sound signals. Further, the one or more second sounds destructively interfere with the one or more first sounds. Further, the amplitude of the one or more second sounds may be equal to the amplitude of the one or more first sounds and the phase of the one or more second sounds may be shifted by 180 degrees in relation to the phase of the one or more first sounds.

Figure 33:
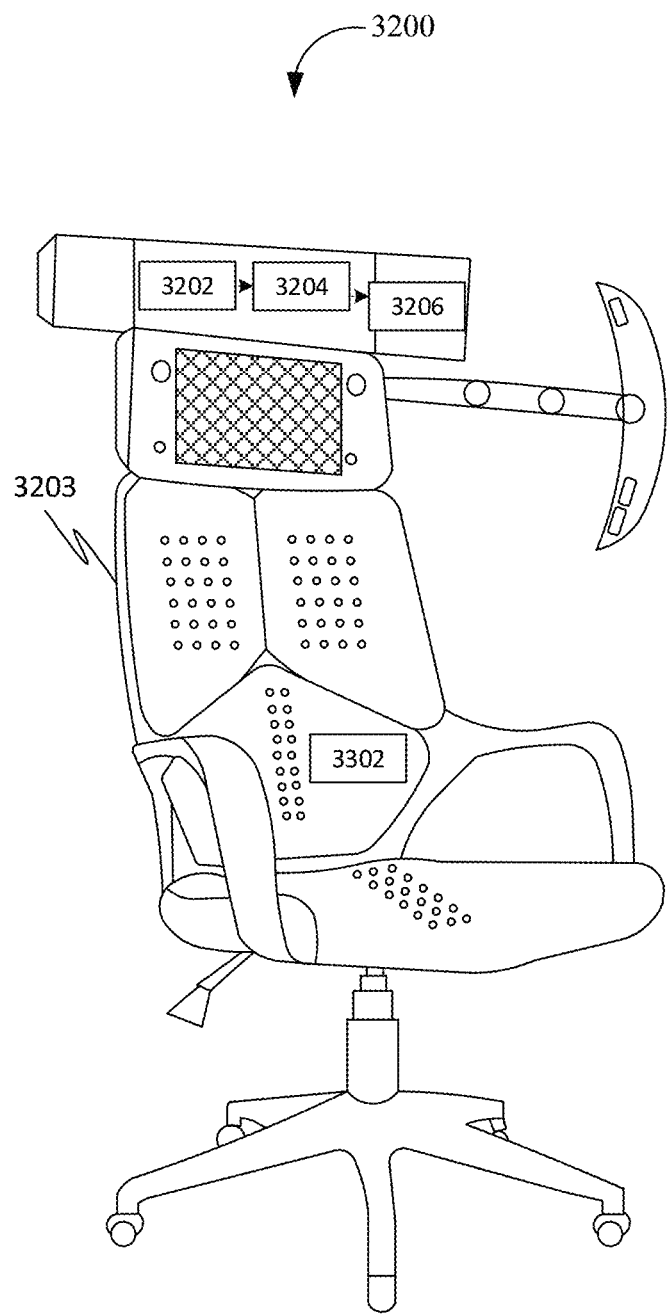
FIG. 33 is a schematic of the system for facilitating stress adaption in the workstation, in accordance with some embodiments.

In further embodiments, the system 3200 may include one or more optical microphones 3302 (as shown in FIG. 33) disposed on the workstation 3203. Further, the one or more optical microphones 3302 may be configured for generating one or more signals based on detecting a variation of one or more light characteristics of one or more light reflected from one or more surfaces of one or more body portions of a user seated in the workstation 3203. Further, the one or more light characteristics may include an intensity, a polarization, a frequency, a wavelength, etc. Further, the processing device 3204 may be communicatively coupled with the one or more optical microphones 3302. Further, the processing device 3204 may be configured for analyzing the one or more signals. Further, the processing device 3204 may be configured for identifying one or more noise sounds in the environment based on the analyzing of the one or more first sound signals and the analyzing of the one or more signals. Further, the processing device 3204 may be configured for determining one or more noise sound characteristics of the one or more noise sounds based on the identifying of the one or more noise sounds. Further, the one or more noise sound characteristics may include a frequency, a phase, an amplitude, a spectrum, a duration, an envelope, a location, etc. of the one or more noise sounds. Further, the determining of the one or more second sound characteristics of the one or more second sounds may be further based on the determining of the one or more noise sound characteristics of the one or more noise sounds. Further, the amplitude of the one or more second sounds may be equal to the amplitude of the one or more noise sounds and the phase of the one or more second sounds may be shifted by 180 degrees in relation to the phase of the one or more noise sounds.

Figure 34:
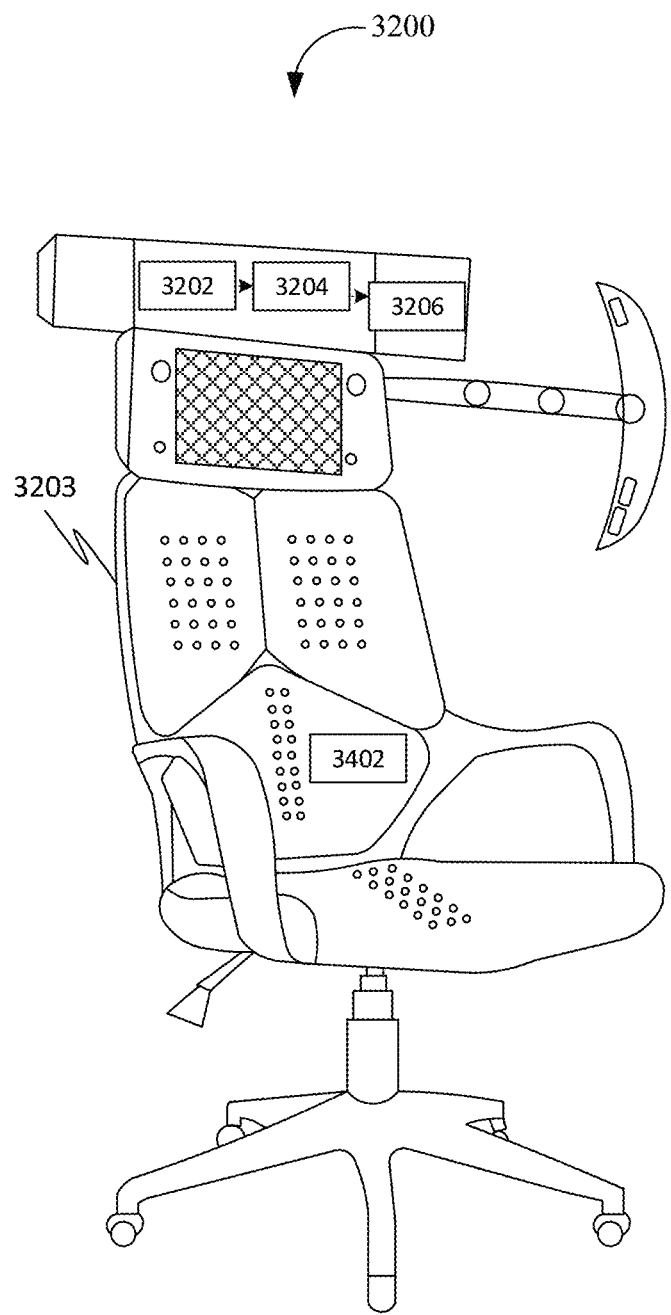
FIG. 34 is a schematic of the system for facilitating stress adaption in the workstation, in accordance with some embodiments.

Further, in some embodiments, the processing device 3204 may be configured for identifying one or more user sounds of the user in the environment based on the analyzing of the one or more first sound signals and the analyzing of the one or more signals. Further, the processing device 3204 may be configured for generating one or more user sound signals of the one or more user sounds based on the identifying of the one or more user sounds. Further, the processing device 3204 may be communicatively coupled with a communication device 3402 (as shown in FIG. 34). Further, the communication device 3402 may be disposed on the workstation 3203. Further, the communication device 3402 may be configured for transmitting the one or more user sound signals to one or more devices.

Figure 35:
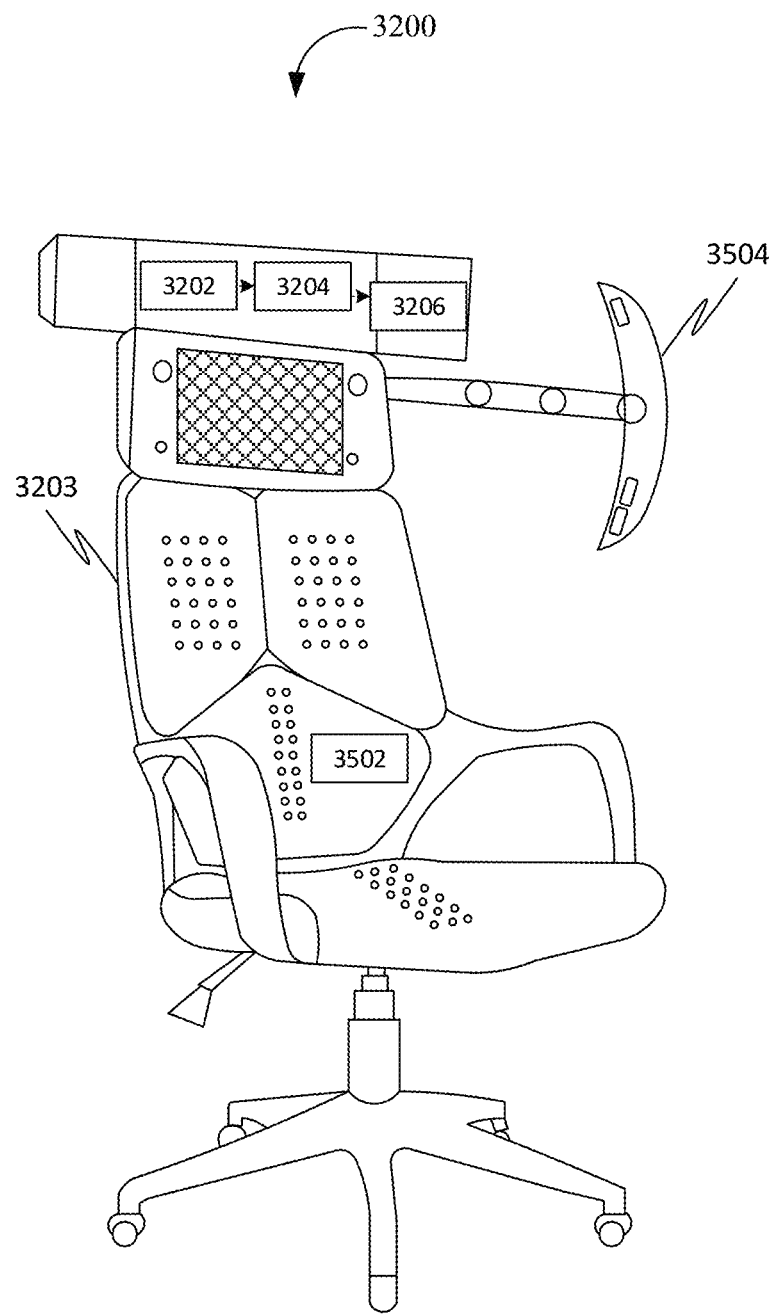
FIG. 35 is a schematic of the system for facilitating stress adaption in the workstation, in accordance with some embodiments.

In further embodiments, the system 3200 may include one or more motion sensors 3502 (as shown in FIG. 35) disposed in the workstation 3203. Further, the one or more motion sensors 3502 may be configured for generating one or more movement data based on detecting one or more movements of the workstation 3203. Further, the one or more movements may include a translatory movement, a rotatory movement, a tilting movement, etc. of the workstation 3203. Further, the processing device 3204 may be communicatively coupled with the one or more motion sensors 3502. Further, the processing device 3204 may be configured for analyzing the one or more movement data. Further, the processing device 3204 may be configured for determining one or more movement characteristics of the one or more movements of the workstation 3203 based on the analyzing of the one or more movement data. Further, the one or more movement characteristics may include a linear displacement of the workstation 3203, an angular displacement of the workstation 3203 around one or more axes of the workstation 3203, etc. Further, the processing device 3204 may be configured for generating one or more commands based on the determining of the one or more movement characteristics. Further, the system 3200 may include a concentric light field near-head display 3504 (as shown in FIG. 35) coupled to the workstation 3203. Further, the concentric light field near-head display 3504 may be communicatively coupled with the processing device 3204. Further, the concentric light field near-head display 3504 may be associated with a field of view. Further, the concentric light field near-head display 3504 may be configured for displaying one or more content on the concentric light field near-head display 3504. Further, the concentric light field near-head display 3504 may be configured for modifying the one or more content based on the one or more commands. Further, the modifying of the one or more content may include shuffling, toggling, resizing, etc.

Figure 36:
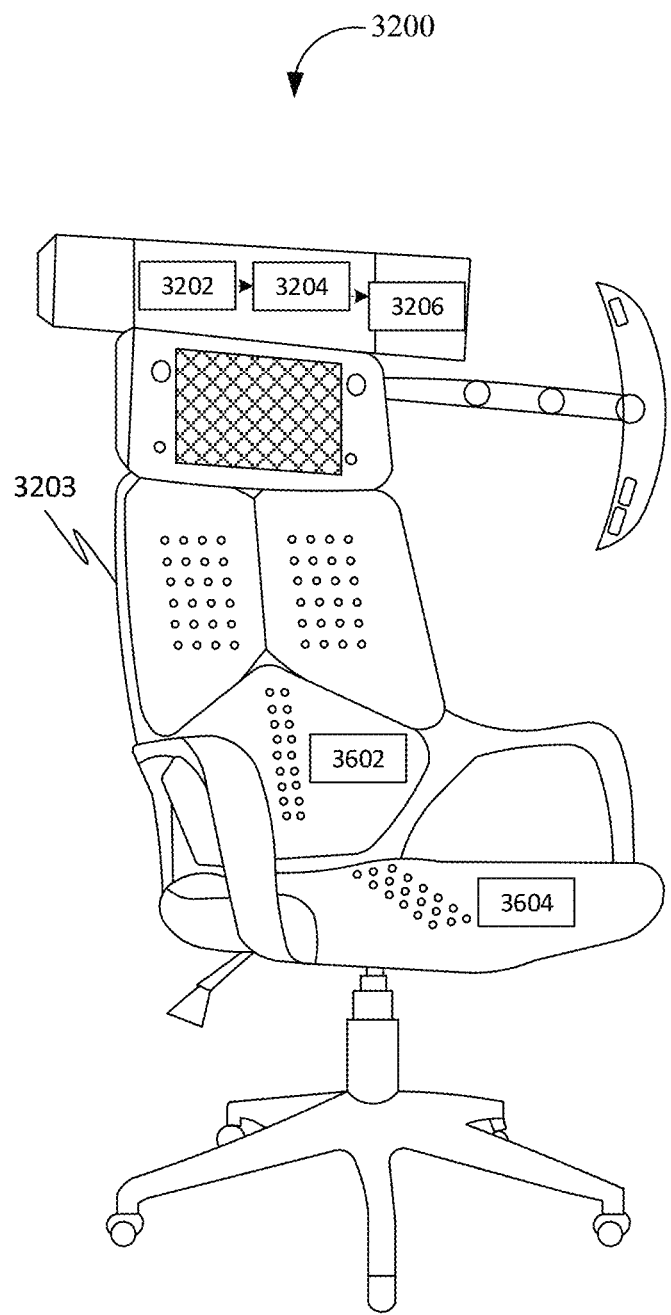
FIG. 36 is a schematic of the system for facilitating stress adaption in the workstation, in accordance with some embodiments.

In further embodiments, the system 3200 may include two or more acoustic transducers 3602 (as shown in FIG. 36) disposed on two or more areas of the workstation 3203. Further, the system 3200 may include one or more input devices 3604 (as shown in FIG. 36) disposed on the workstation 3203. Further, the one or more input devices 3604 may be configured for generating one or more input data. Further, the processing device 3204 may be communicatively coupled with the one or more input devices 3604 and the two or more acoustic transducers 3602. Further, the processing device 3204 may be configured for analyzing the one or more input data. Further, the processing device 3204 may be configured for identifying one or more areas from the two or more areas of the workstation 3203 based on the analyzing of the one or more input data. Further, the processing device 3204 may be configured for identifying one or more acoustic transducers from the two or more acoustic transducers 3602 based on the identifying of the one or more areas. Further, the one or more acoustic transducers may be disposed in the one or more areas of the workstation 3203. Further, the processing device 3204 may be configured for generating one or more commands for the one or more acoustic transducers based on the identifying of the one or more acoustic transducers. Further, the one or more acoustic transducers of the two or more acoustic transducers 3602 may be configured for delivering one or more vibrations at one or more frequencies in the one or more areas based on the one or more commands.

Figure 37:
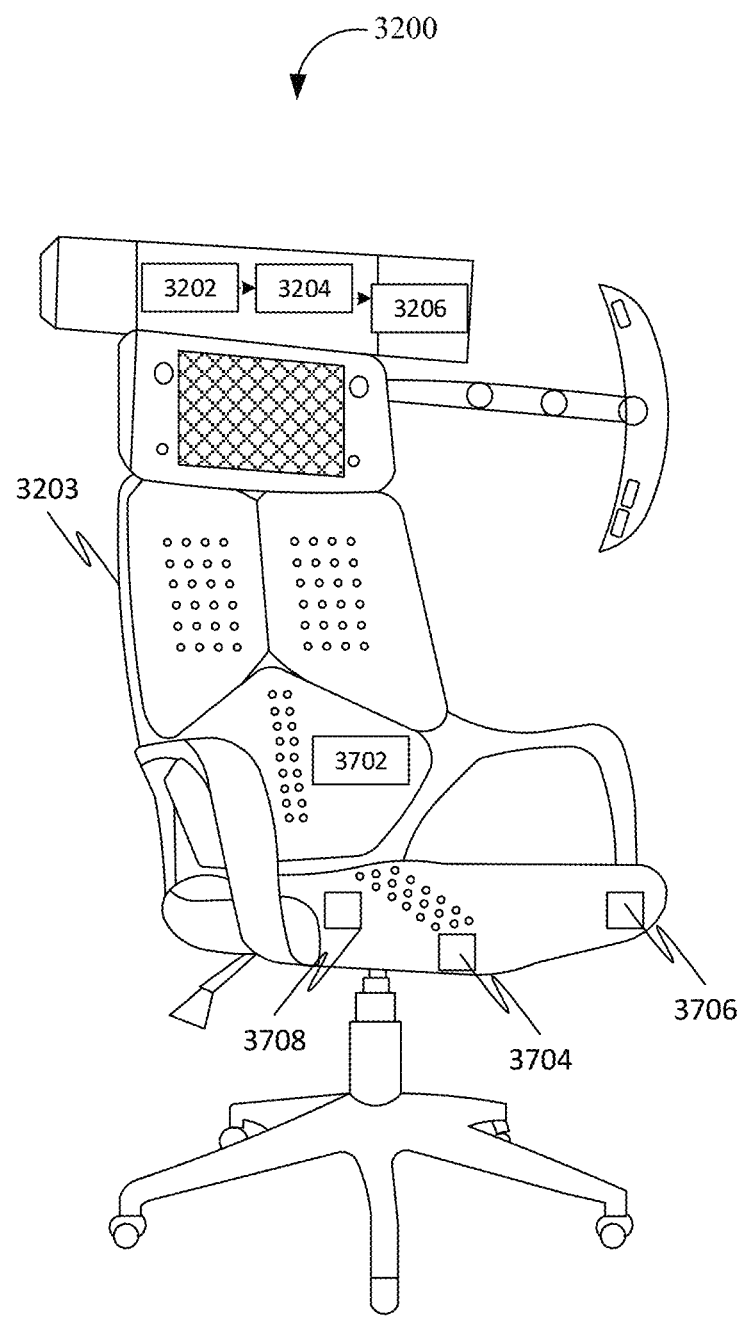
FIG. 37 is a schematic of the system for facilitating stress adaption in the workstation, in accordance with some embodiments.

In further embodiments, the system 3200 may include two or more temperature control devices 3702 (as shown in FIG. 37) disposed in the two or more areas of the workstation 3203. Further, the processing device 3204 may be communicatively coupled with the two or more temperature control devices 3702. Further, the processing device 3204 may be configured for identifying one or more temperature control devices of the two or more temperature control devices 3702 based on the identifying of the one or more areas of the workstation 3203. Further, the processing device 3204 may be configured for generating one or more first commands for the one or more temperature control devices based on the identifying of the one or more temperature control devices. Further, the one or more temperature control devices may be configured for one or more of heating and cooling the one or more areas of the workstation 3203 based on the one or more first commands.

Further, in some embodiments, the one or more input devices 3604 may include one or more pressure sensors 3704. Further, the one or more pressure sensors 3704 may be configured for generating one or more pressure data based on detecting an amount of pressure applied to the two or more areas of the workstation 3203. Further, the one or more input data may include the one or more pressure data. Further, the analyzing of the one or more input data may include analyzing the one or more pressure data. Further, the identifying of the one or more areas may be based on the analyzing of the one or more pressure data.

Further, in some embodiments, the one or more input devices 3604 may include one or more workstation configuration sensors 3706. Further, the one or more workstation configuration sensors 3706 may be configured for generating one or more workstation configuration data based on detecting one or more durations of one or more of a relative position and a relative orientation of one or more first portions of the workstation 3203 in relation to one or more second portions of the workstation 3203. Further, the one or more input data may include the one or more workstation configuration data. Further, the analyzing of the one or more input data may include analyzing the one or more workstation configuration data. Further, the identifying of the one or more areas may be further based on the analyzing of the one or more workstation configuration data.

Further, in some embodiments, the one or more input devices 3604 may include one or more timers 3708. Further, the one or more timers 3708 may be configured for generating one or more timer events after one or more timer durations. Further, the one or more input data may include the one or more timer events. Further, the analyzing of the one or more input data may include analyzing the one or more timer events. Further, the identifying of the one or more areas may be based on the analyzing of the one or more timer events.

Further, in some embodiments, the one or more input devices 3604 may be configured for receiving one or more user inputs. Further, the one or more user inputs may include one or more indications of the one or more areas. Further, the generating of the one or more input data may be based on the receiving of the one or more user inputs.

Figure 38:
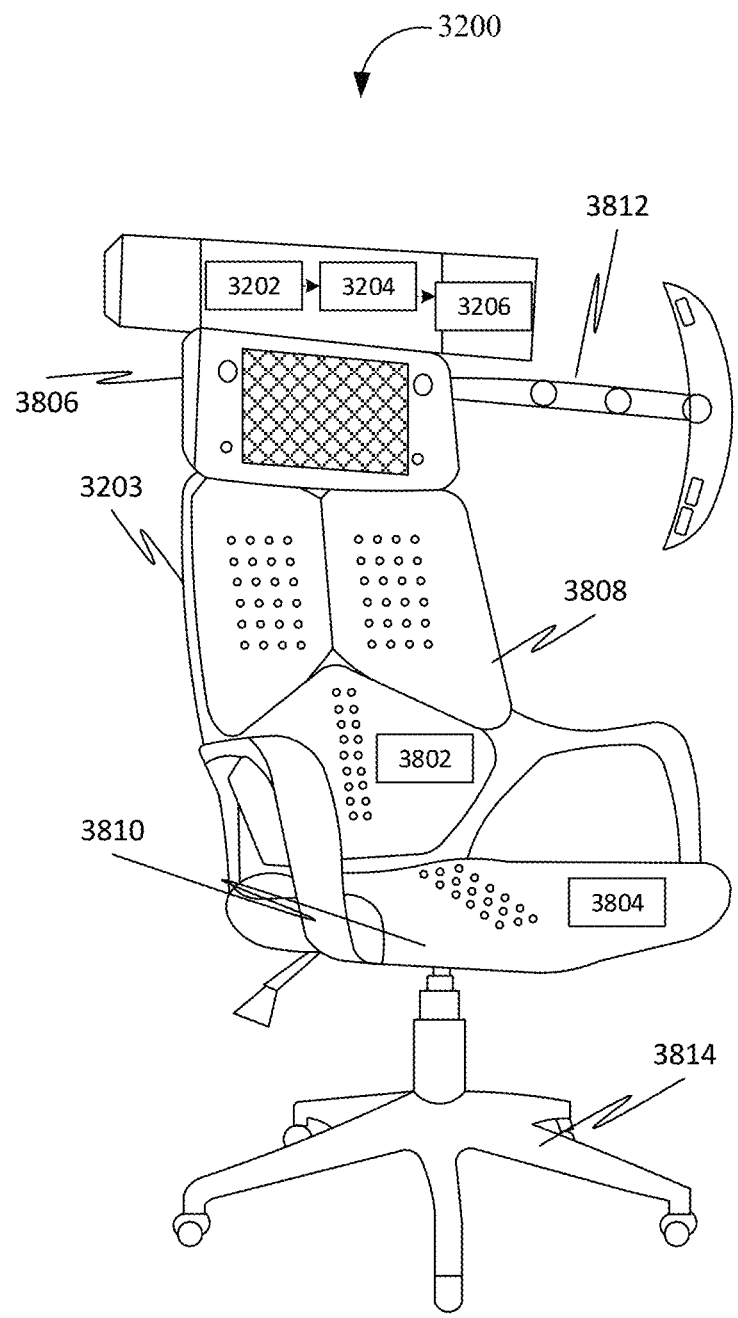
FIG. 38 is a schematic of the system for facilitating stress adaption in the workstation, in accordance with some embodiments.

In further embodiments, the system 3200 may include one or more first input devices 3802 (as shown in FIG. 38) disposed on the workstation 3203. Further, the one or more first input devices 3802 may be configured for generating one or more first input data. Further, the one or more first input data may include one or more regions in the space for one or more third sounds. Further, the one or more acoustic devices 3206 may include two or more acoustic devices. Further, the two or more acoustic devices are disposed on the workstation 3203 in two or more locations of the workstation 3203. Further, the system 3200 may include one or more sensors 3804 (as shown in FIG. 38) disposed in the workstation 3203. Further, the one or more sensors 3804 may be communicatively coupled with the one or more first input devices 3802. Further, the one or more sensors 3804 may be configured for detecting a distance between the two or more acoustic devices and the one or more regions in the space based on the one or more first input data. Further, the one or more sensors 3804 may be configured for generating one or more sensor data based on the detecting of the distance between the two or more acoustic devices and the one or more regions in the space. Further, the processing device 3204 may be communicatively coupled with the one or more sensors 3804. Further, the processing device 3204 may be configured for analyzing the one or more sensor data. Further, the processing device 3204 may be configured for determining a time delay for each acoustic device of the two or more acoustic devices for emitting the one or more third sounds based on the analyzing of the one or more sensor data. Further, the processing device 3204 may be configured for generating two or more acoustic device commands for the two or more acoustic devices based on the determining of the time delay. Further, each acoustic device of the two or more acoustic devices may be configured for emitting the one or more third sounds with the time delay corresponding to each acoustic device of the two or more acoustic devices based on the two or more acoustic device commands. Further, the one or more third sounds constructively interfere in the one or more regions in the space based on the emitting.

Further, in some embodiments, the workstation 3203 may include a headrest 3806, a seatback 3808, a seat 3810, a display chassis 3812, and a wheelbase 3814. Further, one or more of the one or more microphones 3202 and the one or more acoustic devices 3206 may be integrated into the headrest 3806.

Further, in some embodiments, the workstation 3203 may include one or more acoustic melamine materials. Further, the one or more acoustic melamine materials may be integrated into one or more of the headrest 3806, the seatback 3808, and the seat 3810. Further, the one or more acoustic melamine materials reduce the one or more first sounds.

Figure 39:
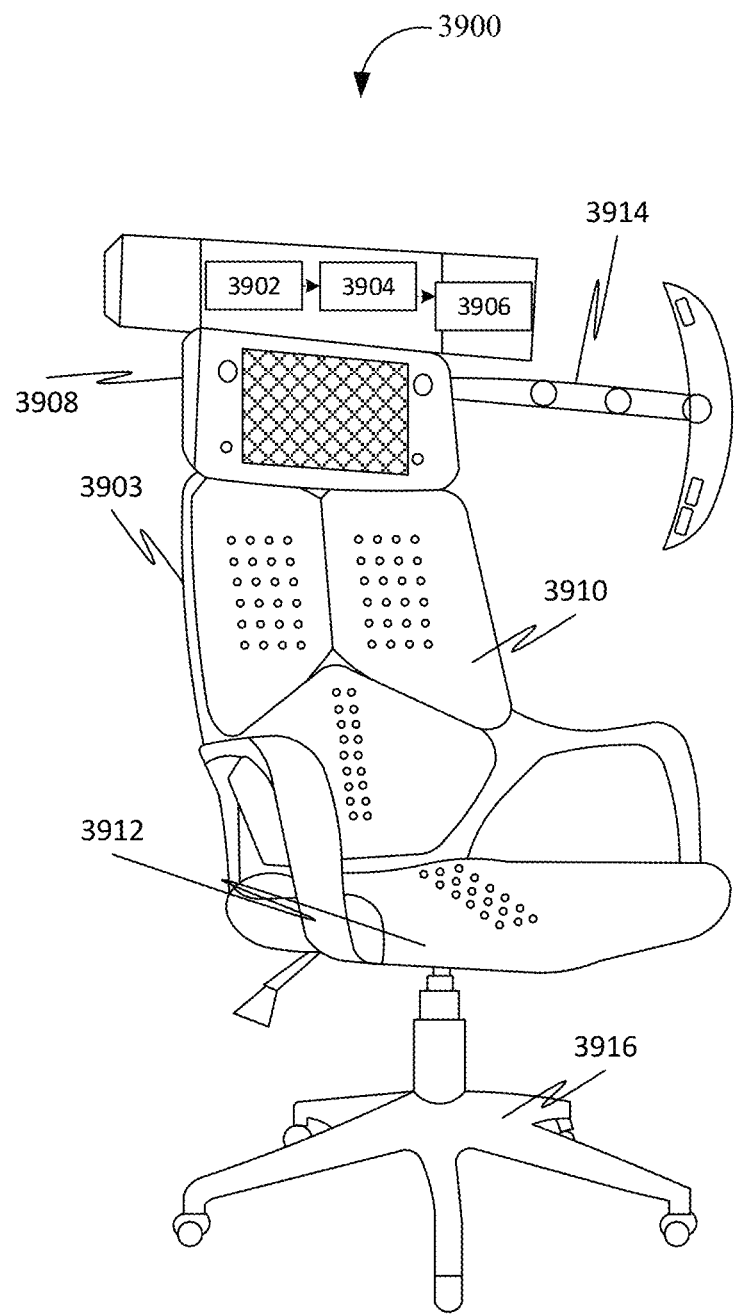
FIG. 39 is a schematic of a system for facilitating stress adaption in a workstation, in accordance with some embodiments.

FIG. 33 is a schematic of the system 3200 for facilitating stress adaption in the workstation 3203, in accordance with some embodiments FIG. 34 is a schematic of the system 3200 for facilitating stress adaption in the workstation 3203, in accordance with some embodiments FIG. 35 is a schematic of the system 3200 for facilitating stress adaption in the workstation 3203, in accordance with some embodiments FIG. 36 is a schematic of the system 3200 for facilitating stress adaption in the workstation 3203, in accordance with some embodiments FIG. 37 is a schematic of the system 3200 for facilitating stress adaption in the workstation 3203, in accordance with some embodiments FIG. 38 is a schematic of the system 3200 for facilitating stress adaption in the workstation 3203, in accordance with some embodiments FIG. 39 is a schematic of a system 3900 for facilitating stress adaption in a workstation 3903, in accordance with some embodiments. Accordingly, the system 3900 may include one or more microphones 3902 disposed on the workstation 3903. Further, the one or more microphones 3902 may be configured for generating one or more first sound signals of one or more first sounds associated with an environment of the workstation 3903. Further, the system 3900 may include a processing device 3904 communicatively coupled with the one or more microphones 3902. Further, the processing device 3904 may be configured for analyzing the one or more first sound signals. Further, the processing device 3904 may be configured for determining one or more first sound characteristics of the one or more first sounds based on the analyzing of the one or more first sound signals. Further, the processing device 3904 may be configured for determining one or more second sound characteristics of one or more second sounds based on the determining of the one or more first sound characteristics. Further, the processing device 3904 may be configured for generating one or more second sound signals for the one or more second sounds based on the determining of the one or more second sound characteristics of the one or more second sounds. Further, the system 3900 may include one or more acoustic devices 3906 disposed on the workstation 3903. Further, the one or more acoustic devices 3906 may be communicatively coupled with the processing device 3904. Further, the one or more acoustic devices 3906 may be configured for emitting the one or more second sounds based on the one or more second sound signals. Further, the one or more second sounds destructively interfere with the one or more first sounds. Further, the system 3900 may include the workstation 3903 that may include a headrest 3908, a seatback 3910, a seat 3912, a display chassis 3914, and a wheelbase 3916. Further, one or more of the one or more microphones 3902 and the one or more acoustic devices 3906 may be integrated into the headrest 3908.

Figure 40:
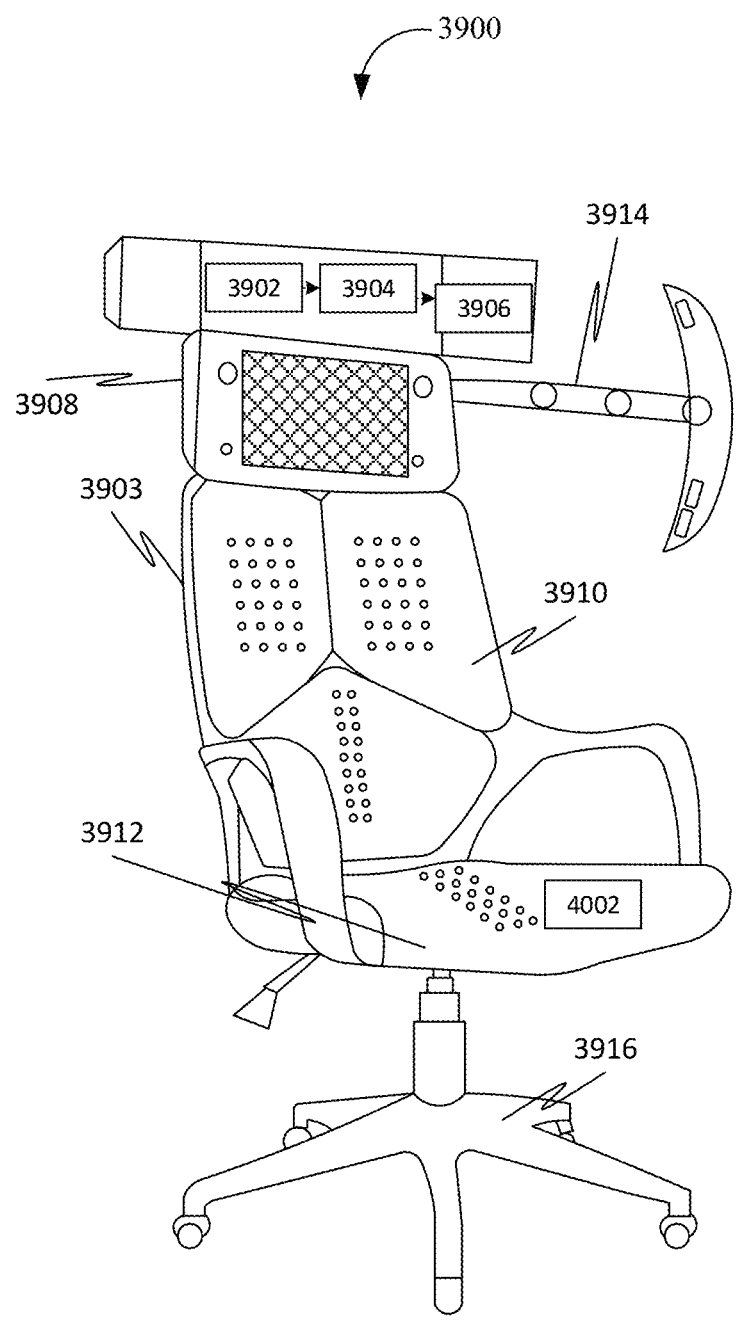
FIG. 40 is a schematic of the system for facilitating stress adaption in the workstation, in accordance with some embodiments.

In further embodiments, the system 3900 may include one or more optical microphones 4002 (as shown in FIG. 40) disposed on the workstation 3903. Further, the one or more optical microphones 4002 may be configured for generating one or more signals based on detecting a variation of one or more light characteristics of one or more light reflected from one or more surfaces of one or more body portions of a user seated in the workstation 3903. Further, the processing device 3904 may be communicatively coupled with the one or more optical microphones 4002. Further, the processing device 3904 may be configured for analyzing the one or more signals. Further, the processing device 3904 may be configured for identifying one or more noise sounds in the environment based on the analyzing of the one or more first sound signals and the analyzing of the one or more signals. Further, the processing device 3904 may be configured for determining one or more noise sound characteristics of the one or more noise sounds based on the identifying of the one or more noise sounds. Further, the determining of the one or more second sound characteristics of the one or more second sounds may be further based on the determining of the one or more noise sound characteristics of the one or more noise sounds.

Figure 41:
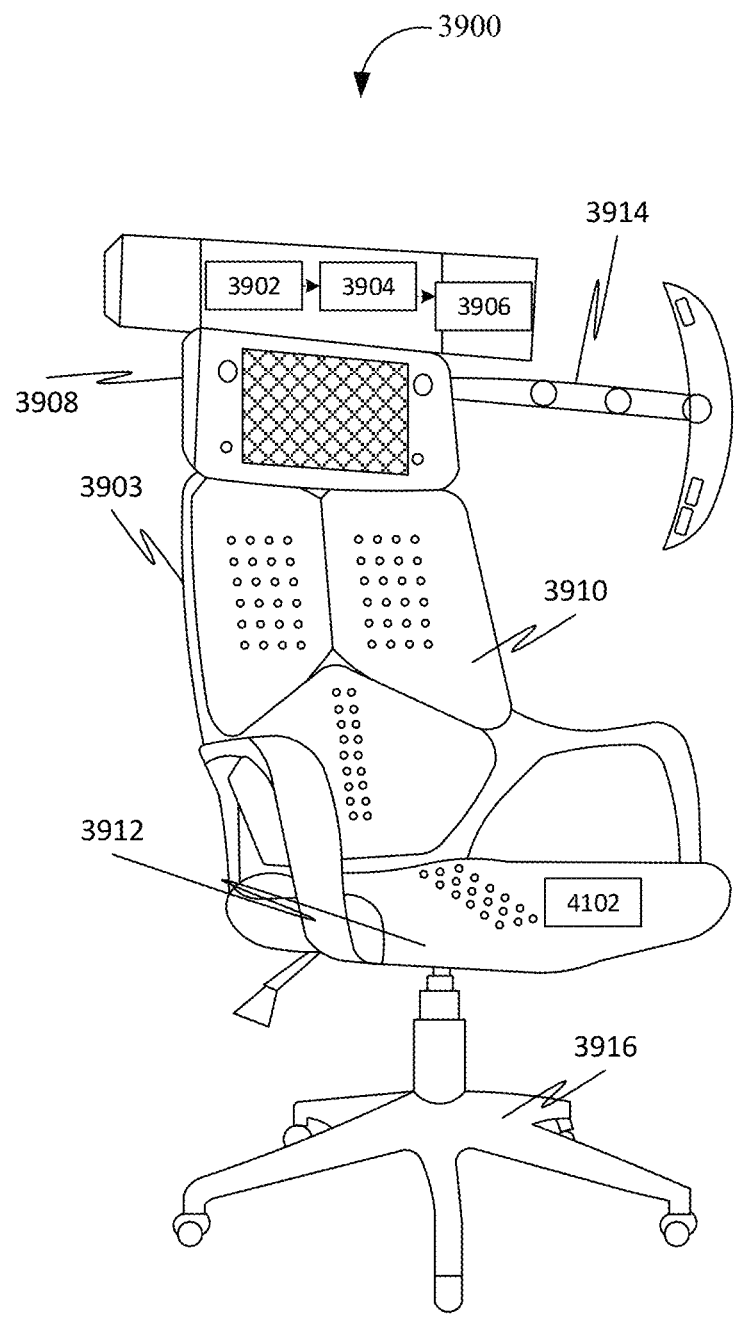
FIG. 41 is a schematic of the system for facilitating stress adaption in the workstation, in accordance with some embodiments.

Further, in some embodiments, the processing device 3904 may be configured for identifying one or more user sounds of the user in the environment based on the analyzing of the one or more first sound signals and the analyzing of the one or more signals. Further, the processing device 3904 may be configured for generating one or more user sound signals of the one or more user sounds based on the identifying of the one or more user sounds. Further, the processing device 3904 may be communicatively coupled with a communication device 4102 (as shown in FIG. 41). Further, the communication device 4102 may be disposed on the workstation 3903. Further, the communication device 4102 may be configured for transmitting the one or more user sound signals to one or more devices.

Figure 42:
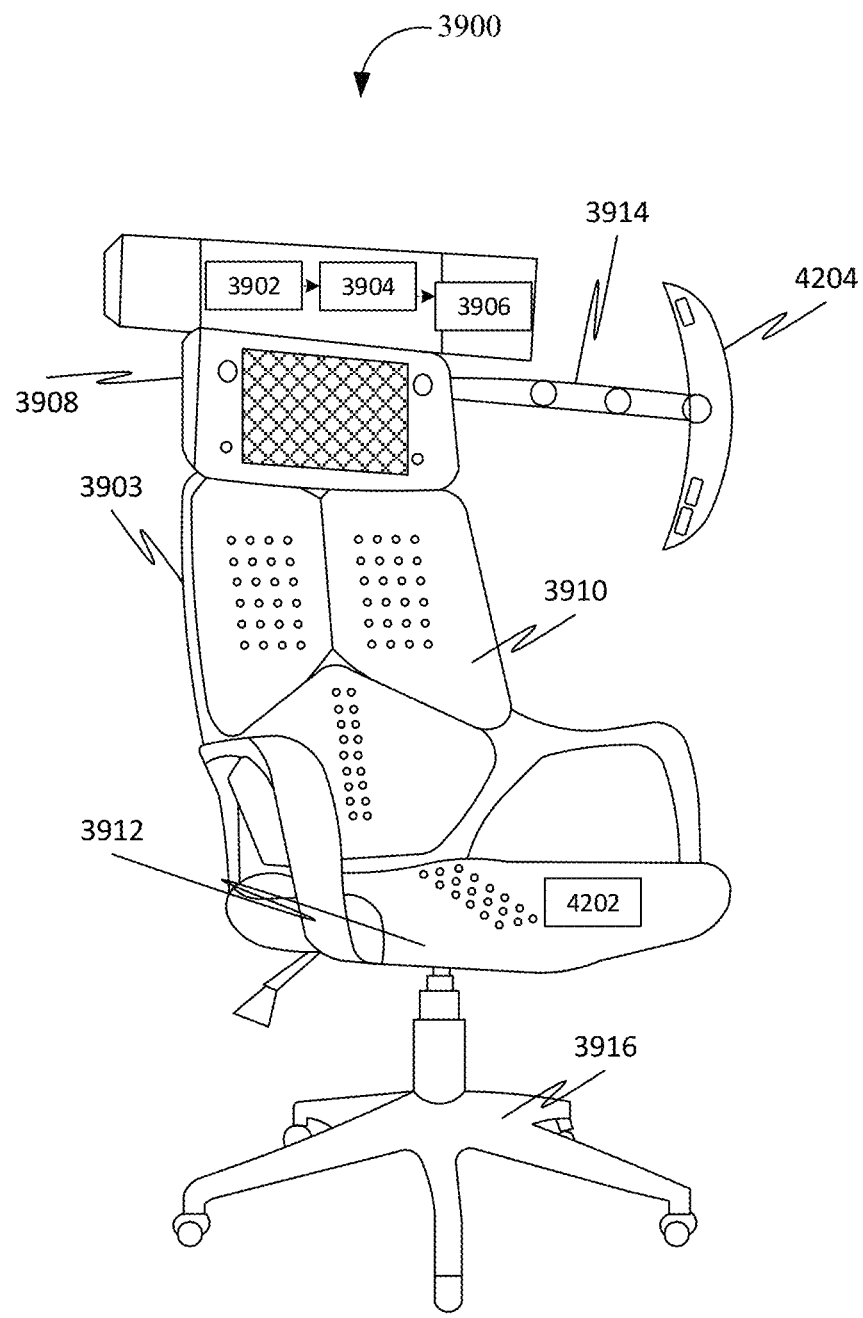
FIG. 42 is a schematic of the system for facilitating stress adaption in the workstation, in accordance with some embodiments.

In further embodiments, the system 3900 may include one or more motion sensors 4202 (as shown in FIG. 42) disposed in the workstation 3903. Further, the one or more motion sensors 4202 may be configured for generating one or more movement data based on detecting one or more movements of the workstation 3903. Further, the processing device 3904 may be communicatively coupled with the one or more motion sensors 4202. Further, the processing device 3904 may be configured for analyzing the one or more movement data. Further, the processing device 3904 may be configured for determining one or more movement characteristics of the one or more movements of the workstation 3903 based on the analyzing of the one or more movement data. Further, the processing device 3904 may be configured for generating one or more commands based on the determining of the one or more movement characteristics. Further, the system 3900 may include a concentric light field near-head display 4204 (as shown in FIG. 42) coupled to the workstation 3903. Further, the concentric light field near-head display 4204 may be communicatively coupled with the processing device 3904. Further, the concentric light field near-head display 4204 may be associated with a field of view. Further, the concentric light field near-head display 4204 may be configured for displaying one or more content on the concentric light field near-head display 4204. Further, the concentric light field near-head display 4204 may be configured for modifying the one or more content based on the one or more commands.

Figure 43:
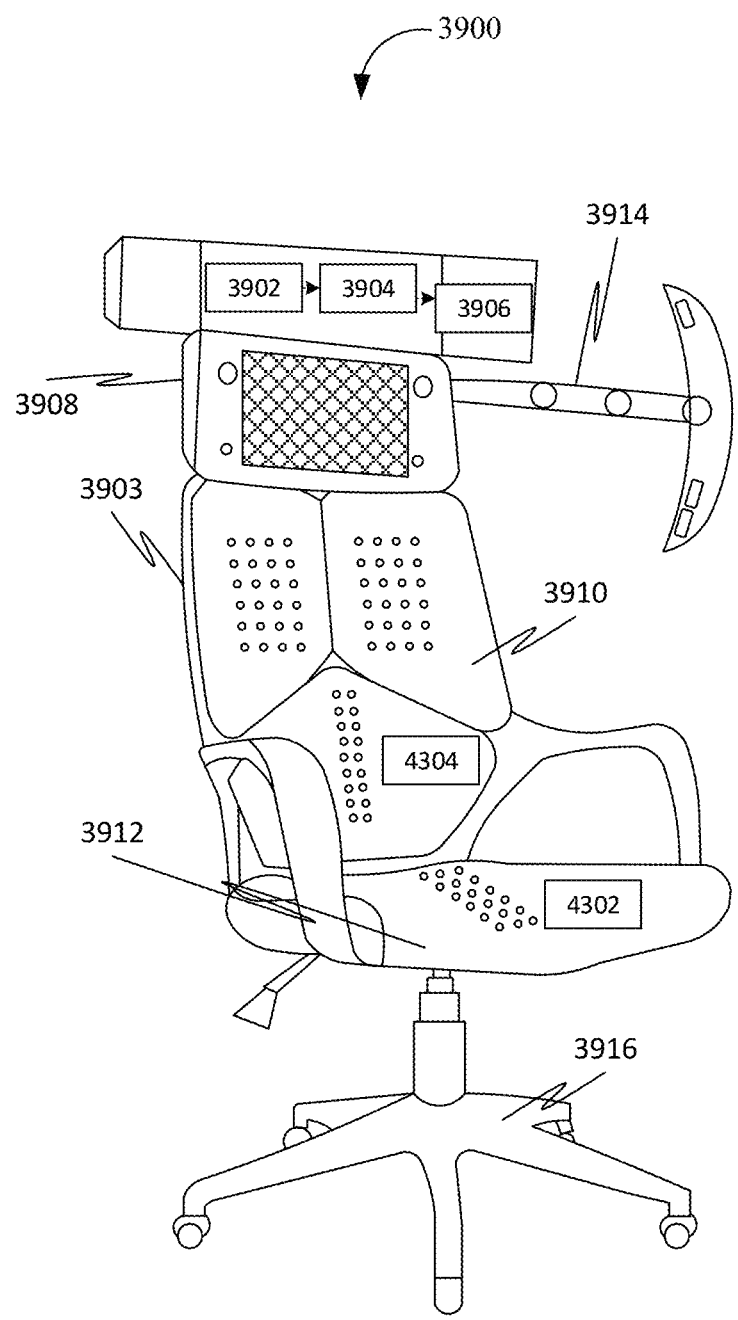
FIG. 43 is a schematic of the system for facilitating stress adaption in the workstation, in accordance with some embodiments.

In further embodiments, the system 3900 may include two or more acoustic transducers 4302 (as shown in FIG. 43) disposed on two or more areas of the workstation 3903. Further, the system 3900 may include one or more input devices 4304 (as shown in FIG. 43) disposed on the workstation 3903. Further, the one or more input devices 4304 may be configured for generating one or more input data. Further, the processing device 3904 may be communicatively coupled with the one or more input devices 4304 and the two or more acoustic transducers 4302. Further, the processing device 3904 may be configured for analyzing the one or more input data. Further, the processing device 3904 may be configured for identifying one or more areas from the two or more areas of the workstation 3903 based on the analyzing of the one or more input data. Further, the processing device 3904 may be configured for identifying one or more acoustic transducers from the two or more acoustic transducers 4302 based on the identifying of the one or more areas. Further, the one or more acoustic transducers may be disposed in the one or more areas of the workstation 3903. Further, the processing device 3904 may be configured for generating one or more commands for the one or more acoustic transducers based on the identifying of the one or more acoustic transducers. Further, the one or more acoustic transducers of the two or more acoustic transducers 4302 may be configured for delivering one or more vibrations at one or more frequencies in the one or more areas based on the one or more commands.

Figure 44:
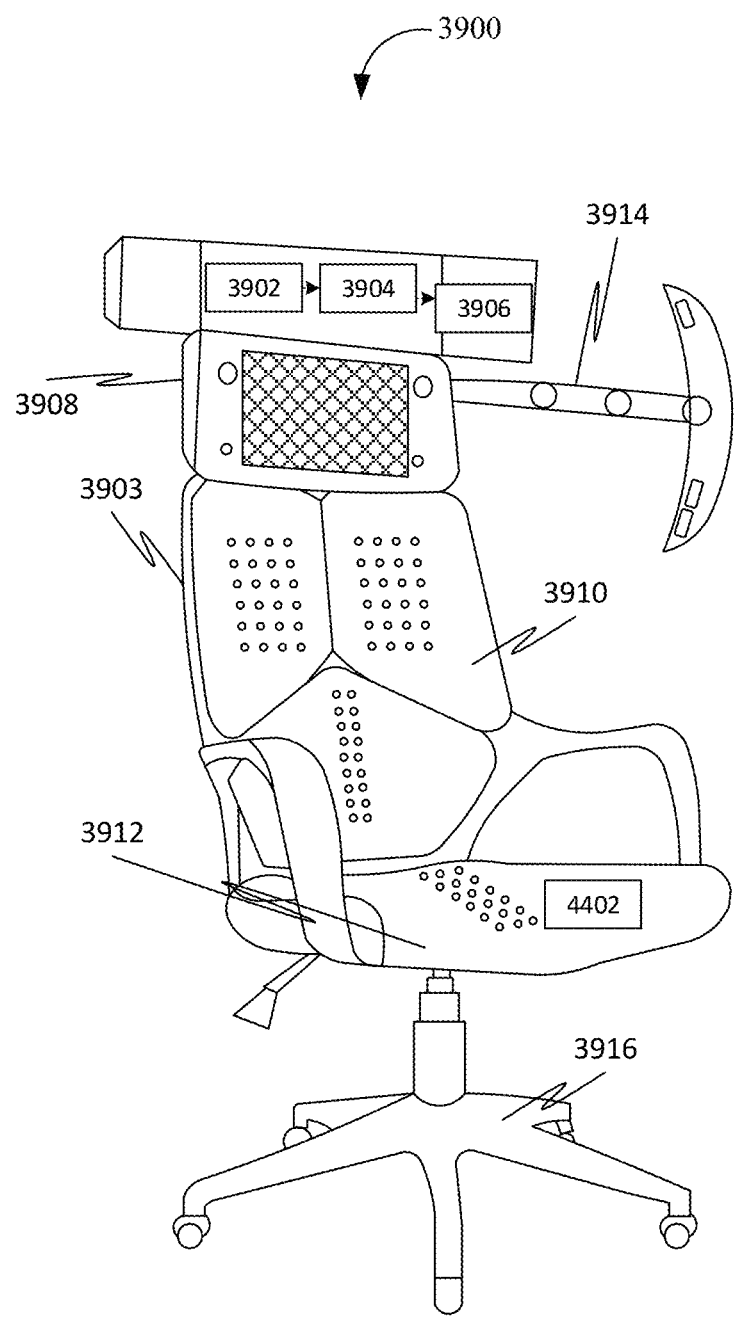
FIG. 44 is a schematic of the system for facilitating stress adaption in the workstation, in accordance with some embodiments.

In further embodiments, the system 3900 may include two or more temperature control devices 4402 (as shown in FIG. 44) disposed in the two or more areas of the workstation 3903. Further, the processing device 3904 may be communicatively coupled with the two or more temperature control devices 4402. Further, the processing device 3904 may be configured for identifying one or more temperature control devices of the two or more temperature control devices 4402 based on the identifying of the one or more areas of the workstation 3903. Further, the processing device 3904 may be configured for generating one or more first commands for the one or more temperature control devices based on the identifying of the one or more temperature control devices. Further, the one or more temperature control devices may be configured for one or more of heating and cooling the one or more areas of the workstation 3903 based on the one or more first commands.

Further, in some embodiments, the one or more input devices 4304 may include one or more pressure sensors. Further, the one or more pressure sensors may be configured for generating one or more pressure data based on detecting an amount of pressure applied to the two or more areas of the workstation 3903. Further, the one or more input data may include the one or more pressure data. Further, the analyzing of the one or more input data may include analyzing the one or more pressure data. Further, the identifying of the one or more areas may be further based on the analyzing of the one or more pressure data.

FIG. 40 is a schematic of the system 3900 for facilitating stress adaption in the workstation 3903, in accordance with some embodiments.

FIG. 41 is a schematic of the system 3900 for facilitating stress adaption in the workstation 3903, in accordance with some embodiments.

FIG. 42 is a schematic of the system 3900 for facilitating stress adaption in the workstation 3903, in accordance with some embodiments.

FIG. 43 is a schematic of the system 3900 for facilitating stress adaption in the workstation 3903, in accordance with some embodiments.

FIG. 44 is a schematic of the system 3900 for facilitating stress adaption in the workstation 3903, in accordance with some embodiments.

FIG. 45A shows a virtual experience station with a display system and various transducers and sensors. In some embodiments, a virtual experience station is used for work or telework applications, entertainment, or health purposes. "Health purposes" or "health treatments" include relaxation techniques, stress mitigation, massage techniques, and any feature to improve a user's physical or mental well-being. A user 22 is disposed at the workstation and can be positioned by a kinematic rig. In the embodiment illustrated in FIG. 45A the kinematic rig is a chair 4500 in which user 22 is seated. However, the kinematic rig may be any suitable structure for facilitating position or supporting the body of user 22 within the virtual experience station. In some other embodiments, the kinematic rig may be a stool, a bed, a mechanical exoskeleton, another form of seating equipment, a support for standing, a support for lying down, or any other suitable equipment for positioning and supporting the body of user 22. Chair 4500 may have various mechanical or electrical adjustments to configure the position for the user. For example, the chair can produce a reclining position, a semi-reclined position, or an upright position, and it can adjust the height and angle through a swivel base.

A mechanical or robotic arm 4, which can have articulated or telescoping joints controlled by the user or the user's motion, can connect chair 4500 to display system 1. In some embodiments, robotic arm 4 is adjusted automatically. In some embodiments, display system 1 is a concentric light field virtual display system (as shown in FIG. 45A) that produces a virtual image 4502 at a position different from the position of display system 1, itself. The concentric light field virtual display system may be used to produce stereoscopic images, monocular depth images, or both. Stereoscopic and monocular depth images may include depth cues to facilitate user 22 having a better understanding of the physical and/or virtual environment. or In some embodiments, the display is a standard display system that produces 2D images or 2D video. In some embodiments, the concentric light field virtual display system is a generic virtual display system. The terms "display" and "display system" are used interchangeably throughout this disclosure.

The display system can include regions to support various transducer arrays that are used for health treatment or for audio/visual interfacing applications. In this disclosure, a "transducer array" is a set consisting of at least one element that can emit or detect a specific type of energy or signal. For example, the signal can be a mechanical wave, such as acoustic or ultrasound, or an electromagnetic wave of any frequency. In some embodiments, there may be no display system, and the virtual experience station has other various rigs to support the transducer arrays. In those embodiments that include a display system, the display system can have embedded in the bezel various transducer arrays, including a camera, camera system, or camera arrays 4504, ultrasound arrays 4505, speaker arrays, visible light arrays, or infrared (IR) or radio frequency (RF) arrays 4506. In some embodiments, the ultrasound array is configured as a high-frequency contactless massager such that the phased-array creates a focal point on the surface of the skin and moves that focal point across the surface of the skin, or it is configured as a carrier for audio signals that are directed to the user. In both cases, the ultrasound array can act as a dynamic phased array, in which the signals emitted by them are delayed relative to each other in a pre-computed way to produce localized regions of strong field intensity. The pre-computed signaling can be produced automatically, through user feedback or motion, or by any other means. In some embodiments, the ultrasound focal point can move across the skin and follow its 3D geometries, with the geometrical information fed as input from a depth camera that captures those 3D geometries. In some embodiments, multiple focal points can be programmed to emulate a sense of human touch or to provide hand massage. In some embodiments, the IR illumination on the face or skin can be modulated by the ultrasound to provide high precision movement capturing mechanisms.

A camera system 4504 comprises at least one camera and can provide a panoramic view of a user, for example, for teleconferencing. In some embodiments, a camera system comprises a plurality of cameras. The panoramic view can be used for three-dimensional reconstruction of the user. Further, the multiple cameras can capture various perspectives of the user 22, the chair 4500, or the surrounding environment for three-dimensional imaging or display applications or for processing techniques such as eye tracking, head tracking, landmark tracking, volumetric sectioning, avatar creation, background blurring, simultaneous localization and mapping (SLAM) based on the user or chair orientation or position, or eye gaze correction. Generally, the geometry of a chair, kinematic rig, person, or other object is a term that includes both the position and the orientation of each item. Cameras can also face outward, away from the specific user, for video see-through applications, in which the display system produces images that include information of the environment behind the display. For example, a camera may capture a scene behind the virtual display which is then incorporated, at least in part, into the virtual image, thereby creating a see-through effect. Similarly, cameras can capture information about the user's hands or fingers for a video see through-effect in which hand or finger tracking is used to allow the user to interact with virtual objects 4503 as part of the virtual images. The camera system can also capture information about other physical objects 3112, such as pen, paper, keyboard, or mouse to display as virtual interactive objects in virtual-reality or screen-sharing modalities. In some embodiments, the camera system is used for overlaying information on control gears of a simulation rig, configured for flight or vehicle simulation applications. In these embodiments, the virtual display is a video-see through display or is transparent or at least partially transparent (e.g., from the perspective of user 22). In some embodiments, the display system is integrated into kinematic gym gear, therapy gear, or medical gear, to help with an immersive exercising environment. In some embodiments, the ultrasonic array is used to mitigate skin humidity, sweat, or temperature or blood circulation for a better experience in exercise, therapeutic, or medical contexts.

Volume sectioning is a technique where a plurality of images of a scene are captured by a respective plurality of cameras, or by a single camera moved to different positions sequentially. Cameras are usually calibrated to minimize distortion. The different images are then compared using software to create a depth map, volume map, or a three-dimensional reconstruction of a scene. For example, two cameras may each capture an image of a scene for stereo photography. The depth information can then be used to segment objects that are located, for example, in the background of a scene, and a blurring algorithm may be used to blur those objects in the resulting image, as may be used in a shared virtual environment.

In some embodiments, the cameras of the camera system are conventional cameras. In some embodiments, they are depth cameras and capture information about depth or sense gestures and poses. They can be of any type. In this disclosure, a "depth camera," "depth sensor," or "RBGD camera" is an imaging device that records the distance between the camera and the distance to an object point. It can be actively illuminated or passively illuminated, and it can comprise multiple cameras to use, e.g., stereo, information. light detection and ranging (LIDAR) and time-of-flight cameras are examples of an active depth camera. A depth camera can also use optical coherence tomography sensing (i.e., autocorrelation). It can use IR illumination to extract depth from structure or shading. Depth cameras can incorporate gesture recognition or facial recognition features. Depth can also be estimated from conventional cameras or a plurality of conventional cameras through, for example, stereo imaging. The camera array or camera system can comprise any of these cameras.

The camera or camera system may capture information about the environment, the kinematic rig, or a user and incorporate that information for display on the virtual display system. In some embodiments, a plurality of users are each using a display system, the display systems each having a communications interface to communicate through a network such as, for example, the internet, a LAN network, or a daisy-chained system. The image captured by the camera of one of the display systems can then be sent to a second display system, such that the second display system can incorporate that image into its display content. This configuration would be useful for telework, teleconferencing, web conferencing, online teaching, or collaborative or multi-player gaming. In some embodiments, a communications interface is used to transfer a data packet about the image. The data packet may define the image itself, a portion of the image, properties of the image, image metadata, or any type of information about the image.

FIG. 45B is a close-up view of the display system 1 in FIG. 45A. The various transducer arrays can be embedded into portions of the display system's enclosure. They can be placed in the bezel or edges, for example. They can also be embedded in a mesh structure and added on to existing displays. IR transducers 4506 can project dynamic patterns on the user or on objects of interest and the reflected light can be used for three-dimensional facial or feature reconstruction, tracking monitoring, or security features. IR illuminators can be used for photometric stereo applications, or for light therapy applications. Ultrasound transducers 4505 or audio transducers can be used for sound production, noise cancellation, audio holography, or any combination of these applications. In the case of ultrasound transducers, the ultrasound frequency can be used as a carrier wave for audio signals. Ultrasound transducers can also be used for massage therapy to reduce eye muscle fatigue or face muscle fatigue. In some embodiments, the camera array 4504 localizes the user's ears to dynamically change the audio or ultrasound signal. In some embodiments, the IR or ultrasound transducer arrays can be used for facial treatments, such as contactless massagers, light therapy, or temperature therapy. The transducer arrays can work in concert with each other or with other arrays or elements, such as audio 2 or microphone arrays 3. In some embodiments, the information captured by the transducer arrays can be transmitted to other displays in teleconferencing applications.

FIGS. 46A through 46D illustrate various configurations of the virtual experience station, involving the transducer and camera arrays, that were discussed in FIGS. 45A and 45B. FIG. 46A depicts a user 22 in a chair 4500 that has an articulated, mechanical arm 4 connected to a display system 1. The display system can produce virtual images 4502. A camera system 4504 can capture information about the user, chair, or environment. In some embodiments, the camera is positioned to capture information about a physical scene 4507 behind the display system and then projects that information on at least one of the images of the display system to produce video see-through applications. Transducer arrays 4505, 4506 can also be embedded into the various parts of the chair.

In some embodiments, as shown in FIG. 46B, the camera system 4504 can capture information about eye gaze and eye tracking information of a user 22 and use that information as feedback for the content produced by the display system 1. For example, in some embodiments, the virtual depths of the virtual images are adjusted to different focal planes 4508, or the positions of the virtual images are shifted to accommodate a user's eye behavior. The information can be used to impact images viewed by other individuals in, for example, teleconferencing applications.

FIG. 46C illustrates an example embodiment that uses IR or near-IR (NIR) illumination. NIR illumination is the portion of the IR electromagnetic spectrum that is nearest to the visible spectrum. The IR electromagnetic spectrum also includes mid-IR and far-IR regimes. An IR or NIR transducer array 4506 can produce projection illumination onto a user 22 for dynamic lighting applications. The arrays can be coupled to the display system 1. Such an embodiment can be used for tracking the user, the chair, or the environment. In some embodiments, the IR or NIR transducer arrays can be configured as optical microphones that sense acoustic vibrations. The transducer arrays can work in concert with a camera or camera arrays 4504 to impact images produced by the display system.

FIG. 46D uses an ultrasound transducer array 4505 for localized audio. The array can be built into the display system 1. The camera system 4504 tracks the head and ears of a user 22, and the information is fed into the ultrasound array to produce localized audio or ultrasound signals at a user's ear by dynamically adjusting the relative phase delays of each of the transducer signals, so that the audio signal produced by the display system is localized near the user's ears, and that other individuals in the environment do not hear the audio signal. The system can also capture environmental noise for noise cancellation effects.

Figure 47A:
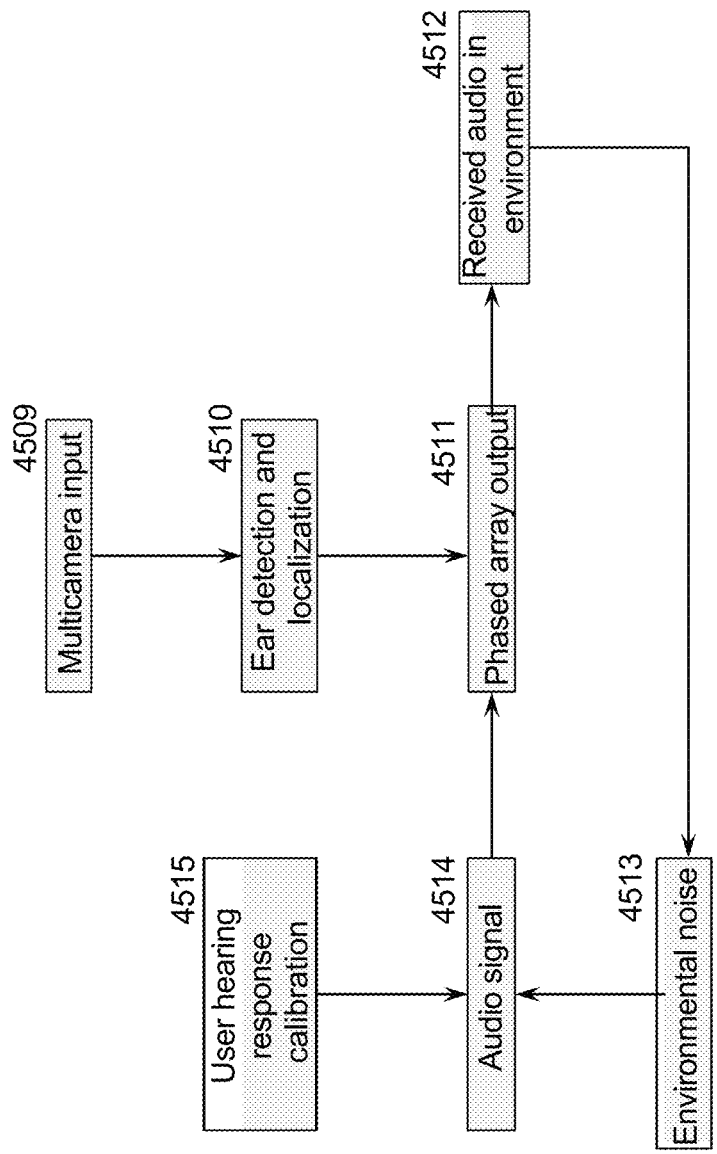
FIG. 47A is a diagram to describe a holographic or phased-array ultrasound audio system for the virtual experience station.

The processing pipeline for ultrasound phased array can operate as shown in the block diagram of FIG. 47A. In some embodiments, this pipeline is integrated with the block diagram of FIG. 24. The camera system, or multicamera system 4509, records visual information about the user and sends that into a localization algorithm 4510 to reconstruct the positions of the left and right ears. The position information is sent to an algorithm that controls the phase-array output 4511. The signals produced by the transducers are then sent to environment 4512, which includes a user. Information about environment noise 4513 is detected by ultrasound, audio, or optical microphones, and the information is incorporated into audio signal 4514, which is compensated to cancel that noise. In some embodiments, the user's hearing response 4515 may be used to calibrate the system. For example, the aural transfer function of the user can be incorporated to optimize the signal produced by the transducer array.

The ultrasound transducer array can act as a beam forming mechanism for localized audio, audio holography, or acoustic fields. For example, denote the positions of the left and the right ear are located as $r_L$ and $r_R$, respectively. The ultrasound transducer array is configured to produce a signal $f(r)$ that is approximately zero unless $r=r_R$ or $r=r_L$. The term "approximately" means to within a precision on the order of the size of the ear or ear canal. Each source transducer produces a localized wave, such as a spherical wave. The $n^{th}$ source can produce a spherical wave $A_n \exp(i(kr_n+\alpha_n))$, where $A_n$ is the amplitude of the wave, k is the wavenumber (rad/m), $r_n$ is the distance between the source and the point of observation, $\alpha_n$ is a phase constant, and "exp" is the exponential function. The total field is the sum of each spherical wave:

$$f(r)=\Sum_{n=1}^{N} A_n e^{i(kr_n+\alpha_n)} \quad (9)$$

Processing software seeks to minimize the difference between $f(r)$ and the ideal waveform $f_{ideal}(r)$ that exactly replicates a desired signal:

$$\operatorname{argmin}_{\{\alpha\}}\{||f_{ideal}(r)|^2-|f(x)|^2|\}. \quad (10)$$

Although both the amplitude and the phase offset can be modified, the phase is a more sensitive parameter and can be adjusted by introducing relative delays. If the phase differences form a geometric sequence, then the matrix corresponding to the optimization problem may be characterized as a Vandermonde matrix. Various cost functions can be included in the optimization problem. For example, prior constraints can be incorporated into the minimization.

Figure 47C:
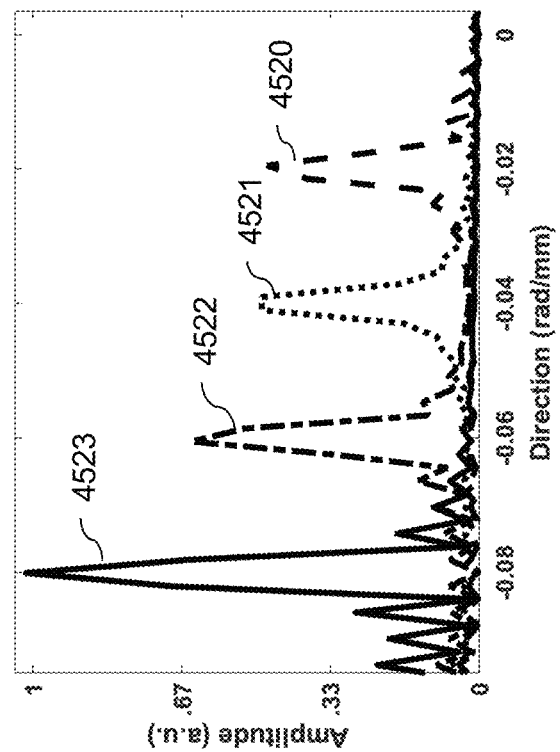
FIG. 47B and FIG. 47C are numerical simulations of an ultrasound audio holographic or phased-array system.
Figure 47B:
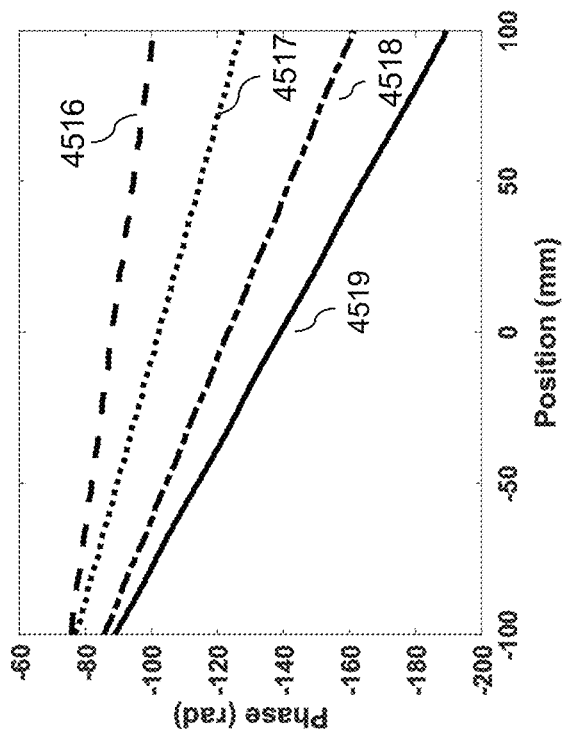

A numerical simulation of this method, using linear phase delays is shown in FIG. 47B. In this case, a linear phase offset of a one-dimensional array of 100 transducers is introduced. The phase $\alpha_n$ is proportional to the position $x_n$ of the transducer along the x-axis: $\alpha_n=Mx_n$ for some proportionality constant M. By increasing the proportionality constant M, the slope of the resulting plane wave changes. The tilt of the wavefront is shallowest 4516 for the smallest proportionality constant. The tilt increases to a slightly less steep slope 4517 for a bigger proportionality constant. The tilt increases further 4518 for a bigger proportionality constant. The tilt is largest 4518 for the biggest proportionality constant.

In some embodiments the resulting audio information is based on the virtual environment that a user is viewing. For example, a virtual image may be perceived as far away, based on monocular or binocular depth cues, and a sound effect due to that image will be perceived as low in volume. In contrast, a virtual image that is perceived as being closer may be associated with a sound effect is perceived as louder or more directional, i.e., as being closer to left ear than to the right ear.

If the ears are located in the far field, this tilt corresponds to a shift of the location of field maxima, as shown in FIG. 47C. The field energy is localized to regions that depend on the phase tilt. The smallest shift 4520 corresponds to the smallest phase tilt. The next shift 4521 corresponds to the next larger phase tilt. The next shift 4522 corresponds to the next phase tilt, and the largest shift 4523 corresponds to the steepest phase tilt.

Shown in FIGS. 48A through 48C are examples of applications of the camera arrays for virtual environments, such as virtual reality and teleconferencing applications, based on the virtual experience station of FIG. 45A. In FIG. 48A, each camera in the camera system 4504 captures information about a user 22 from a different perspective 4524. The information is processed for volumetric or three-dimensional reconstruction of a user. Information about facial expression, gestures, hand or eye position, and posture is recovered and used to render an avatar image 4525 of the user for virtual-reality applications with the display system 1. The camera system can perform three-dimensional reconstruction of a user or a part of a user. In some embodiments, these reconstructions are used to amplify user movements to control the virtual objects or to interact with the virtual content. In some embodiments, a predictive algorithm such as trained network for 3D hand models may be used to predict the user's intent based on smaller micro gestures.

In the embodiment shown in FIG. 48B, the display system 1 can show a virtual image 4502. The virtual image can be farther from the user or closer to the user. In some embodiments, the closer virtual images are produced using retroreflective elements, retroreflective elements, or phase conjugating elements. In some embodiments, camera system 4504 acts as a depth or gesture sensor and can allow the user 22 to interact with the virtual images. Augmented-reality annotations can also be mapped onto virtual images for a user to interact with.

Depicted in FIG. 48C is an embodiment in which the cameras in the camera system 4504 capture different perspectives 4524 and consequently capture three-dimensional information about the user's environment, such as background items 4526. The environmental information can be used for better blurring 4527 of the user's background for teleconferencing video images 4502 with the display system 1. In some embodiments, multiple users' faces can be detected, and the display system can maintain focus for those faces while blurring the mutual background.

Figure 49A:
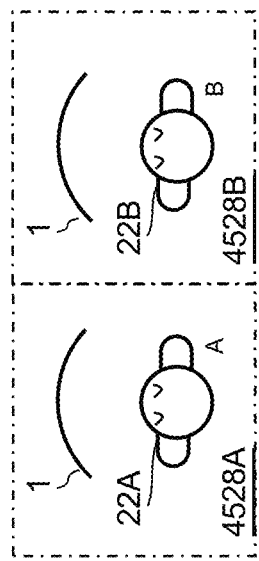
FIGS. 49A through 49G depict various virtual-reality applications based on the tracking and spatial localization and mapping capabilities of the virtual experience station.
Figure 49B:
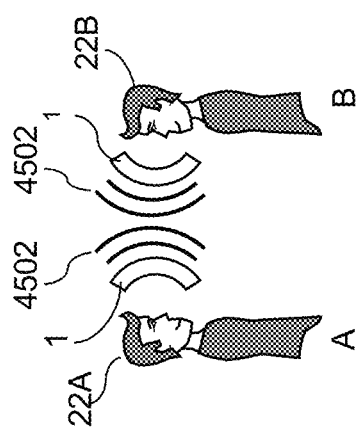

FIGS. 49A through 49F depict various interactive features that use eye, head, or gaze tracking. The camera or camera array discussed above can track users' eyes, faces, and heads to use as eye gaze correction. In this way multiple users can interact virtually through the virtual display. Shown in FIG. 49A are two users; user A 22A is in a first room or environment 4528A, and user B 22B is in a second room or environment 4528B. These environments can be in physically distinct spaces, or they can be in different orientations in the same space. The eye gaze correction system detects where each user is looking, and the information is sent to the rendering pipelines of the display systems 1. The result is a 2D or 3D virtual environment, such as virtual office or virtual arena or field shown in FIG. 49B, in which user A 22A and user B 22B both appear to be making eye contact with each other as they look through their respective display systems 1 at virtual images of each other 4502.

Figure 49C:
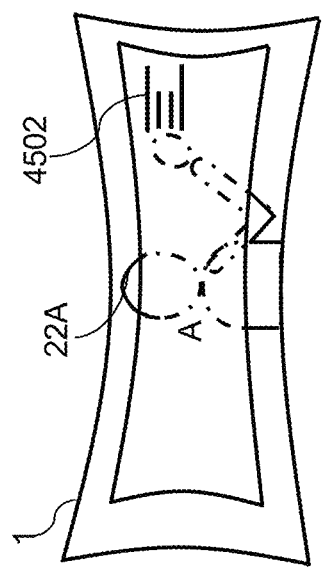

In some cases, a shared virtual environment may include a shared workspace, such as a shared document or whiteboard can be used with similar features. This example is shown in FIG. 49C, which depicts the view of user A 22A from the perspective of user B from FIG. 49B. In this example embodiment, user A is sharing a workspace and interacting with the workspace's virtual images 4502, such that user A appears to be facing user B through user B's display system 1 and they can interactively write on the whiteboard or paper. In some embodiments, the camera system captures the hand and the desk space and multiplexes that information at the same location or at a desired depth layer to mimic a shared space between the calling entities.

Figure 49D:
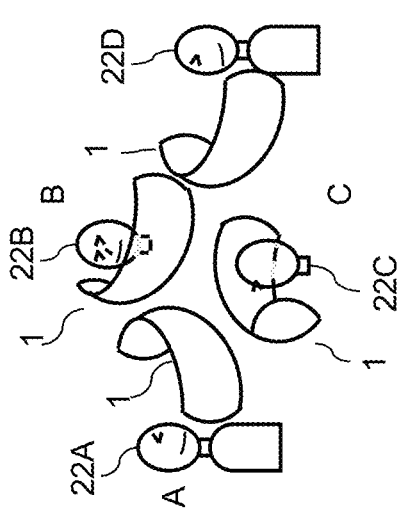
Figure 49E:
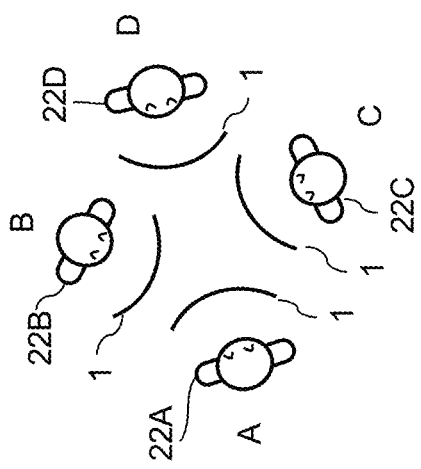

Similarly, some embodiments are implemented with more than two users, as depicted in FIG. 49D, which illustrates the effective use of tracking, such that the virtual images produced by each user's display system make the virtual environment appear more realistic for each user. For example, the camera system and tracking methods can be used such that it appears as if user B 22B, user C 22C, and user D 22D are making eye contact with user A 22A through each of their respective display systems 1. FIG. 49E is an overhead view of this virtual environment. In some embodiments, the camera system provides a spatial localization and mapping capability such that if the user moves his/her head or swivels a chair, that movement will impact the content accordingly to further simulate presence in the virtual world.

Figure 49F:
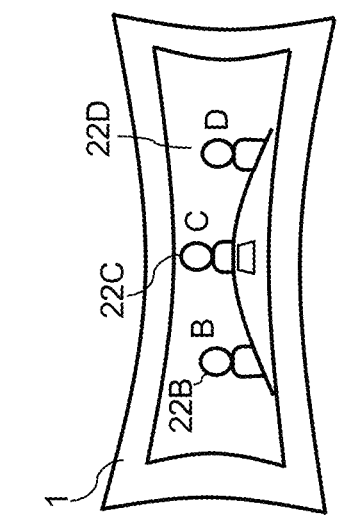

FIG. 49F illustrates an example virtual image as seen by user A through a display system 1, in which user A sees users B 22B, C 22C, and D 22D making eye contact or facing each other in a virtual environment, configured as in FIG. 49D.

Generally a "virtual environment" is a collection of display content or virtual images, that may be able to interact with each other. The display content may have as its source camera images or computationally rendered images, such as computer graphics. The virtual environment can be a virtual reality environment, in which all the content is virtual display content; it can be an augmented or mixed reality environment, in which virtual images are super-imposed a physical environment; or in can be a conventional image content from a display panel like an LCD panel. In some embodiments, the virtual environment comprises only one virtual image. Virtual environments may be used by a single user in the kinematic rig, or they may be shared or displayed by a plurality of display systems that are in communication with each other through, for example, the internet, or any type of wired or wireless network. A "shared virtual environments" is a virtual environment that may be used for any collaborative activity, including telework applications, teleconferencing, web conferencing, online teaching, or collaborative or multi-player gaming. In a shared virtual environment, different users may view the display content from different perspectives.

Figure 49G:
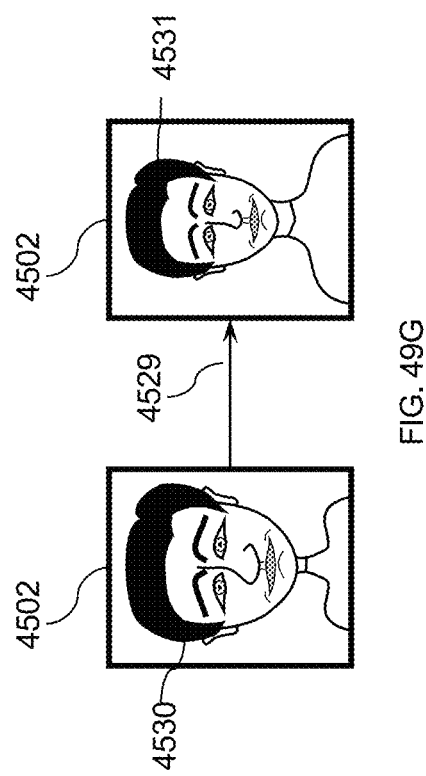

As shown in FIG. 49G, in these embodiments, the camera system can use depth information about a user for depth-based remapping. Depth remapping is an example of projection remapping, or remapping. This can be used in virtual displays, or in conventional display applications. Information about a user's distance to the camera system and to the display system can be processed through a software pipeline 4529 to render a virtual image 4531 of the user that maintains the correct physical or geometric proportions of the user compared to an uncompensated or distorted image 4530. For example, projection remapping may involve calibrating a camera for distortion, using isomorphisms such as homography to map features from the physical environment to the images recorded by a camera, or implementing a neural radiance field (NeRF) for generating 3D scenes from a set of 2D images. In this way, multiple users can interact more personally and more realistically through their images 4502. Projection remapping may be used for correcting depth errors, projecting images from perspectives different the that captured by a camera, or building a composite image from a set of individual images. This application can be used for virtual reality systems or for conventional display systems. In some embodiments, artistic features or cosmetic blemishes can also be corrected.

Figure 50E:
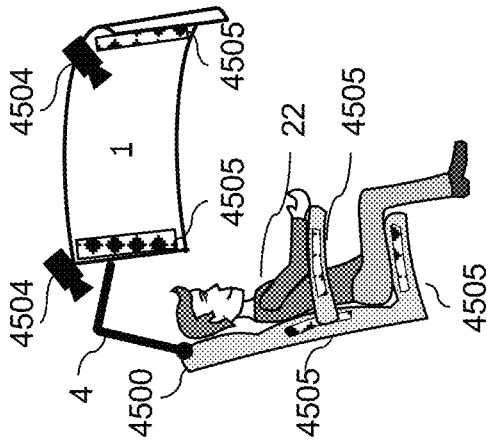
FIGS. 50A through 50E depict various configurations of transducer arrangements for use in health treatments.
Figure 50B:
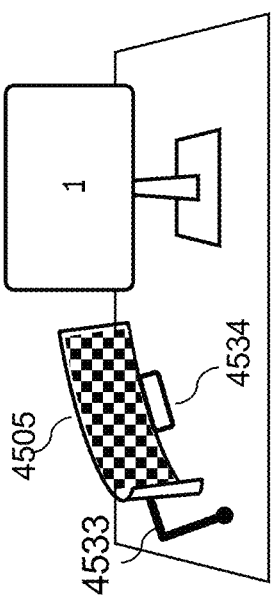
Figure 50D:
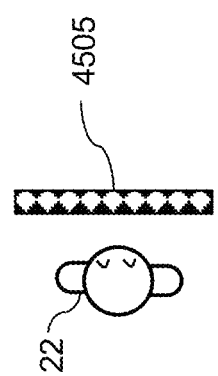
Figure 50A:
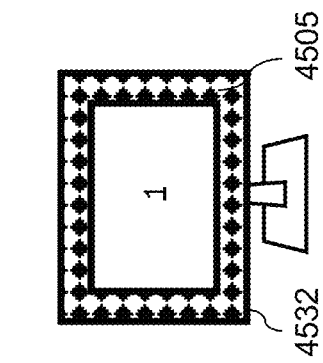

Shown in FIGS. 50A through 50G are various configurations of the transducers described in FIGS. 45A and 45B, configured for use as health treatments, such as contactless massagers or heaters, or IR or NIR light therapy. FIG. 50A shows, from a user's perspective, the display system 1 and transducer arrays, such as ultrasound arrays 4505, that were discussed in FIG. 45A. The transducer array can alternatively be IR or NIR, UV, or visible-light transducer arrays. Here, the transducers are built into a bezel around the display system. In some embodiments, the transducers are built into a mesh 4532 that is placed over a standalone monitor, such that they therefore convert the standalone monitor into a virtual experience station embodiment that has the transducers already built into it. The transducer array that is embedded into a mesh is portable and may be used in different setups or systems. The display system 1 can be a virtual display or a conventional display.

In such embodiments, the ultrasound transducer array is modulated to direct ultrasound energy to various portions of a user's face or body. The localization of the massaging feature is on the order of the wavelength of the ultrasound wave. Ultrasound frequencies are approximately 20 kHz, and the wavelength is approximately 2 cm or 1 cm. approximately above. The ultrasound wave can penetrate to a depth different that audible acoustic waves. In some embodiments, the acoustic field is combined with a localized ultrasound field to create a holographic sound experience. This holographic acoustic field is then matched to the content being shown on the screen. For example, in a game or video when a fly passes by the character's ear and sits on his ear, the user first feels the sound coming from a far distance, then hears the localized sound next to the ear (the sound of fly's wings very close to the ear), and then feels a gentle touch on the hear from the ultrasound focal point. In another example, when an explosion happens in a game, the user first hears the explosion but then simultaneously feels an impact on his/her skin via the ultrasound phased array. In some embodiments, the holographic sound system is synchronized with the game engine to use the visual 3D geometry to emulate the needed acoustic field. In some embodiments, the acoustic field is created by a predictive algorithm that is trained using a combination of data from game engines and acoustic wave propagation physics.

Figure 50C:
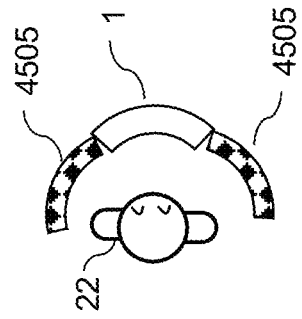

FIG. 50B depicts a standalone transducer array 4505 next to a display system 1. In this case, the array is configured as a contactless face massager. The array can be connected to or rest on a desk via an articulated arm 4533, and the array position and orientation can be manipulated with a handle 4534. The transducer array can alternatively be IR or NIR, UV, or visible light arrays. The standalone transducer array can be flat or curved. Similarly, there can be a plurality of standalone transducer arrays. In FIG. 50C, for example, the display system 1 is disposed between two transducer arrays. The array can be an ultrasound array 4505 The transducer array can alternatively be IR or NIR, UV, or visible light arrays. In some embodiments, the array is located at the edges of a 2D or virtual display, or it is an accessory bar that sits below the screen.

In some embodiments, as shown in FIG. 50D there need not be a display system at all, and the transducer array can act as a contactless massager, temperature, humidity therapy device, or light treatment device as a standalone feature. It can be an ultrasound array 4505. The transducer array can alternatively be IR or NIR, UV, or visible light arrays.

FIG. 50E depicts the transducer arrays 4505 used for health treatments built into both the display system 1 and the virtual experience station itself. The arrays can also be distributed in the bezel of the display system. They can also be disposed within the chair back, headrest, arm rest, or seat of the chair. In some embodiments, it is mounted on top of the bed; the bed or chair can be in a cabin of any vehicle or airplane or in any room setting. The chair 4500, articulated or robotic arm 4, and camera array 4504 can all be configured to communicate with the transducer arrays to provide optimal signaling based on orientation and position of the user 22.

FIGS. 51A through 51E depict various configurations of the station from FIGS. 45A and 45B. As shown in FIG. 51A, the workstation can be configured such that the chair 4500 reclines to various angles. The workstation can include leg rests 4535 that are disposed at adjustable angles. Physical objects, such as a keyboard or trackpad, can be integrated into an arm as a work panel 4536 of the workstation. The workstation can also have a built-in visor 4537, which can act as either a display system for the user, or a facial treatment, or both. It can be mounted to a head-covering 4538, and the visor and head-covering can have moveable parts to optimize use. In all embodiments involving a chair, the motion and orientation of the chair can be influenced by feedback about the user's posture, health, or focus, which can be captured through sensor arrays that are electrically coupled to the workstation.

Shown in FIG. 51B is an example embodiment in which the workstation can be a standing station with a display system 1 and without a chair. In some embodiments, transducer arrays 4505 and pressure sensors are built into the floor 4539 to impact the legs or feet of the user 22. The transducer arrays can also be built into the rigs that supports the display system.

FIG. 51C depicts a chair workstation in which passive noise cancellation panels 12 or acoustic foam 24 are built into the various components of the chair 4500 for better noise cancellation effects in the audio or acoustic signal heard by a user 22. The panels can comprise, for example, melamine foam, composite multilayer melamine foam structure, acoustic metamaterial structure-based paneling, as described in FIG. 6.

Shown in FIG. 51D is a similar embodiment, in which the sensors or transducer arrays 4505 are disposed inside the chair 4500 used by a user 22. Each set of transducers can provide a different function, or they can all provide the same function.

In all these embodiments, the transducers can be controlled by user input, local timers, remote control, or any other means.

Shown in FIG. 51E is an example tandem workstation, in which two users 22 are physically near to each other. Users A and B each have their own workstation and display system 1, but there can be a shared space 4540 in which virtual images are rendered based on the relative orientation and position of user A 22A and user B 22B. These two users can interact with other users in other environments through the tandem virtual display system.

FIG. 51F shows an example integration of the virtual display system 1 into the ceiling of the cabin for a vehicle, airplane, or a room, such that the virtual display shows a virtual image 4502 that is recessed into the depth of the ceiling 4541 and tilted at an angle that is visible to a user 22. In some embodiments, the user sits in a chair 4500. The display system has a mirrored or half-mirrored segment 4543 with a hidden camera 4504 behind the mirrored or half-mirrored surface 4542, such that the user 22 sees virtual objects 4503 at the same depth of the reflection 4542 of his/her hand and can interact with those virtual objects in the depth of the mirror without having to touch the screen. In this way, the display system, mirrored or half-mirrored surface, and camera together form an interactive virtual mirror display. In some embodiments, the hidden camera is a depth camera feeding depth information to a half-mirrored section of the virtual screen. In some embodiments, passive noise cancellation panels 12 or acoustic foam 24 are built into the various components. In some embodiments are integrated other transducer arrays, such as ultrasound, IR, RF, visible-light, UV, microphone, or camera arrays.

FIG. 51G shows an example integration of a similar system as in FIG. 51F, configured for use with a bed 4544. The display system is connected by a hinge 4545 hinged to a wall or a flat surface behind the head of the user, where the mount base 4546 goes under the mattress to mechanically support the weight of the display. The hinge lets the display system fold up against or align with the wall or flat surface. In this embodiment, like the embodiment in FIG. 51F, along with a tilted and recessed virtual image 4502, the user sees his/her own hands' reflections 4543 in the half-mirrored section and can interact with the virtual content or virtual objects 4503 without having to hold up the hand. The user can rest a hand on his/her body because the depth of the virtual images matches the depth of the reflection of the hand. The user can interact with the virtual objects naturally in the half-mirrored section while seeing the content hovering behind the aperture of the virtual display. The display then can fold back to be vertically integrated into the wall. In some embodiments, passive noise cancellation panels 12 or acoustic foam 24 are built into the various components. In some embodiments are integrated other transducer arrays, such as ultrasound, IR, RF, visible-light, UV, microphone, or camera arrays.

In all bed and chair embodiments in FIGS. 51A through 51G, the chair can have transducer arrays and other interfaces to reduce stress, improve immersion, or provide medical use cases.

Although the present disclosure has been explained in relation to its preferred embodiment, it is to be understood that many other possible modifications and variations can be made without departing from the spirit and scope of the disclosure. In the specification the term "or" is generally used is the sense of "logical or" but it should also be understood to disclose another embodiment where "or" is read as the "logical exclusive or." In the claims "or" is used in the "logical or" sense unless the "logical exclusive or" sense is expressly stated.

What is claimed is:

1. A virtual experience station comprising:
   a virtual display system;
   a kinematic rig to position or support a body of a user;
   a camera system positioned to capture an image about the kinematic rig or the user and coupled to the virtual display system;

a plurality of ultrasound transducers to produce a spatially profiled audio field; and a processor, operably connected to the camera system and the virtual display system, to incorporate information from the image into a virtual image,
  direct the virtual display system to output the virtual image as at least a part of a virtual environment,
  determine, based at least in part from the image, positions of a left ear and a right ear of the user, and
  control the plurality of ultrasound transducers to produce a first localized audio signal about the left ear and a second localized audio signal about the right ear.

2. The virtual experience station of claim 1, wherein the virtual image is among a plurality of virtual images and the processor is further to instruct the virtual display system to output the plurality of virtual images at a respective plurality of virtual depths.

3. The virtual experience station of claim 1, wherein the virtual display is to provide both monocular and stereoscopic depth cues.

4. The virtual experience station of claim 1, wherein the virtual experience station is for use as a collaborative activity, wherein a data packet based on the image is communicated to a display system that is in communication with the virtual experience station.

5. The virtual experience station of claim 4, wherein
the camera system is to capture a plurality of images, the image being among the plurality of images, and each of the plurality of images capturing a different perspective of the user, and
the processor is to receive the plurality of images and to generate the virtual image at least in part by remapping the perspectives of the user from the plurality of images to remove image distortion.

6. The virtual experience station of claim 4, wherein
the camera system is to capture a plurality of images, the image being among the plurality of images, and each of the plurality of images capturing a different perspective of the user, and
the processor is to receive the plurality of images and to generate the virtual image at least in part from the plurality of images by using a volume sectioning algorithm to blur a background of the user.

7. The virtual experience station of claim 1, wherein
the camera system includes at least one camera to capture the image,
the at least one camera is positioned to capture a scene behind the virtual display system in the image, and
the processor is further to incorporate at least a portion of the scene from the image into to the virtual image to create a see-through effect.

8. The virtual experience station of claim 1, wherein the virtual display system has a transparent or partially transparent portion, for a see-through effect.

9. The virtual experience station of claim 1, wherein
the image is among a sequence of images that the camera system is to capture sequentially,
the processor is to operate on each of the images in the sequence, thereby producing and outputting a sequence of virtual images, and
the processor is further to track a movement of a physical object over the sequence of images and move a virtual object in the sequence of virtual images based on the movement of the physical object.

10. The virtual experience station of claim 9, wherein the physical object tracked by the processor is a body part of the user.

11. The virtual experience station of claim 10, wherein the body part is a hand of the user, and the processor is to move the virtual object based on the movement of the hand of the user.

12. The virtual experience station of claim 10, wherein the body part is an eye of the user, the virtual object is a virtual eye of the user, and the processor is to adjust a gaze of the virtual eye of the user in the virtual image based at least in part on the movement of the eye of the user.

13. The virtual experience station of claim 9, wherein the virtual objects form part of a shared workspace in the virtual environment.

14. The virtual experience station of claim 9, wherein the physical object tracked by the processor is a geometry of the kinematic rig.

15. The virtual experience station of claim 1, further comprising a plurality of infrared transducers to output a dynamic pattern of infrared light onto a face of the user and to sense reflected infrared information, wherein
  the processor is further to receive the infrared information, and to generate a projection mapping or a facial reconstruction of the user based at least in part on the dynamic pattern and sensed infrared information.

16. The virtual experience station of claim 15, wherein the infrared transducers are embedded in the virtual display system.

17. The virtual experience station of claim 1 wherein the plurality of ultrasound transducers capture a property of an environmental noise and the processor is further to generate at least one noise suppression signal based on the environmental noise, the noise suppression signal for suppressing the environmental noise perceived by the user.

18. The virtual experience station of claim 1, wherein the plurality of ultrasonic transducers are embedded in a portion of the virtual display system.

19. The virtual experience station of claim 1, wherein the plurality of ultrasound transducers are a first plurality of ultrasound transducers, and the virtual experience station further comprises a second plurality of ultrasound transducers, wherein the second plurality of ultrasound transducers are to provide a spatial profile haptic feedback or a tactile sensation to the user, the spatial profile based on a position of the user.

20. A feedback-enhanced rig comprising:
  a kinematic rig for supporting a user within an operational region;
  a plurality of transducers to receive a feedback signal generated by the user, and at least one of said transducers to emit a stimulating signal into the operational region; and
  a feedback-loop processing module operably coupled to the plurality of transducers to receive the feedback signal and adjust the stimulating signal based on the feedback signal.

21. The feedback-enhanced rig of claim 20, wherein the transducers are ultrasound transducers and the stimulating signal acts as a non-contact massager for a body part of the user.

22. The feedback-enhanced rig of claim 20, wherein the transducers are infrared transducers and the stimulating signal provides light therapy treatment for a body part of the user.

23. The feedback-enhanced rig of claim 20, further comprising illuminators to direct ultraviolet or white-light to a portion of the operational region to provide a facial treatment.

24. The feedback-enhanced rig of claim 20, further comprising a display system.

25. The feedback-enhanced rig of claim 24, wherein the at least one of the plurality of transducers is embedded in the display system.

26. A virtual experience station comprising:
- a virtual display system;
- a kinematic rig for positioning in an operational region a body of a user, and for positioning a line of sight of the user in a viewing range of the virtual display system;
- a plurality of transducers positioned to couple to the operational region, the plurality of transducers to measuring information about the user and to emit energy that impacts a body part of the user; and
- a plurality of isolating components positioned about the operational region to suppress acoustic noise entering the operational region.

27. The virtual experience station of claim 26, wherein the plurality of transducers are ultrasound transducers that are for a massaging application.

28. The virtual experience station of claim 26, wherein the kinematic rig is a chair.

29. The virtual experience station of claim 26, wherein the plurality of isolating components comprise at least of one of acoustic absorbent materials and active noise cancelling devices.

30. The virtual experience station of claim 26, wherein the virtual display system is integrated into a structure above the operational region, and an image produced by the display is tilted relative to a surface of the display system.

31. The virtual experience station of claim 26, wherein the kinematic rig is a seat inside a cabin of a vehicle.

32. The virtual experience station of claim 31, wherein the virtual display system is integrated into a structure above the operational region, and an image produced by the display is tilted relative to a surface of the display system.

33. The virtual experience station of claim 26, further comprising
- a motion tracking module to track a position of a hand of the user, wherein
- the virtual display system further comprises a reflective portion oriented to reflect at least a portion of the operational region into the line of site, and
- the virtual display system is further to output a virtual image comprising a virtual object at a position determined by the position of the hand of the user.

34. A virtual experience station comprising:
- a virtual display system;
- a kinematic rig to position or support a body of a user;
- a camera system coupled to the virtual display system and positioned to capture a plurality of images, a first image being among the plurality of images, and each of the plurality of images capturing a different perspective of the user; and
- a processor, operably connected to the camera system and the virtual display system, to
  - receive the plurality of images,
  - generate a virtual image at least in part from the plurality of images by using a volume sectioning algorithm to blur a background of the user, and
  - direct the virtual display system to output the virtual image as at least a part of a virtual environment, wherein
- the virtual experience station is configured for use as a collaborative activity,
- a data packet based on the first image is communicated to a display system that is in communication with the virtual experience station.

35. The virtual experience station of claim 34, wherein the camera system includes at least one camera to capture the first image, the at least one camera is positioned to capture a scene beyond the virtual display system in the image.

* * * * *